(12) United States Patent
Berthiaume et al.

(10) Patent No.: US 11,788,145 B2
(45) Date of Patent: Oct. 17, 2023

(54) EPIGENEIIC SILENCING OF NMT2

(71) Applicant: PACYLEX PHARMACEUTICALS INC., Calgary (CA)

(72) Inventors: Luc G. Berthiaume, Edmonton (CA); Erwan Beauchamp, Edmonton (CA)

(73) Assignee: PACYLEX PHARMACEUTICALS INC., Calgary (CA)

( * ) Notice: Subject to any disclaimer, the term of this patent is extended or adjusted under 35 U.S.C. 154(b) by 75 days.

(21) Appl. No.: 15/745,578

(22) PCT Filed: Jul. 18, 2016

(86) PCT No.: PCT/CA2016/050846
§ 371 (c)(1),
(2) Date: Jan. 17, 2018

(87) PCT Pub. No.: WO2017/011907
PCT Pub. Date: Jan. 26, 2017

(65) Prior Publication Data
US 2018/0208990 A1    Jul. 26, 2018

Related U.S. Application Data

(60) Provisional application No. 62/194,109, filed on Jul. 17, 2015.

(51) Int. Cl.
| | | |
|---|---|---|
| C12Q 1/68 | (2018.01) | |
| C12Q 1/6886 | (2018.01) | |
| A61K 31/496 | (2006.01) | |
| A61K 31/704 | (2006.01) | |
| A61K 31/713 | (2006.01) | |
| A61K 31/7105 | (2006.01) | |
| A61K 45/06 | (2006.01) | |
| A61P 35/00 | (2006.01) | |
| A61K 38/00 | (2006.01) | |

(52) U.S. Cl.
CPC .......... *C12Q 1/6886* (2013.01); *A61K 31/496* (2013.01); *A61K 31/704* (2013.01); *A61K 31/713* (2013.01); *A61K 31/7105* (2013.01); *A61K 45/06* (2013.01); *A61P 35/00* (2018.01); *A61K 38/00* (2013.01); *C12Q 2600/106* (2013.01); *C12Q 2600/136* (2013.01); *C12Q 2600/154* (2013.01)

(58) Field of Classification Search
None
See application file for complete search history.

(56) References Cited

U.S. PATENT DOCUMENTS

| | | |
|---|---|---|
| 5,164,414 A | 11/1992 | Vincent et al. |
| 7,449,464 B2 | 11/2008 | Martin et al. |
| 7,662,818 B2 | 2/2010 | Martin et al. |
| 7,981,889 B2 | 7/2011 | Barr Martin et al. |
| 2003/0180292 A1 | 9/2003 | Hanna et al. |
| 2005/0227919 A1 | 10/2005 | Ashworth et al. |
| 2006/0142231 A1 | 6/2006 | Ashworth et al. |
| 2007/0179160 A1 | 8/2007 | Helleday |
| 2010/0068731 A1 | 3/2010 | Sharma et al. |
| 2011/0312921 A1 | 12/2011 | Brand et al. |
| 2019/0000838 A1 | 1/2019 | Berthiaume et al. |

FOREIGN PATENT DOCUMENTS

| | | |
|---|---|---|
| AU | 2004220321 B2 | 2/2010 |
| AU | 2010202197 A1 | 6/2010 |
| BR | PI0408284 A | 3/2006 |
| BR | PI0417056 A | 2/2007 |
| BR | 112014001430 A2 | 2/2017 |
| CA | 2547077 A1 | 6/2005 |
| CA | 2670837 A1 | 6/2008 |
| CA | 2517629 C | 7/2011 |
| CN | 101631466 A | 1/2010 |
| CN | 1788000 B | 7/2010 |
| CN | 1905864 B | 4/2011 |
| CN | 102107008 A | 6/2011 |
| CO | 5650256 A2 | 6/2006 |
| DK | 1633724 T3 | 8/2011 |
| EC | SP056094 A | 3/2006 |
| EP | 1684736 A1 | 8/2006 |
| EP | 2305221 A1 | 4/2011 |
| EP | 1633724 B1 | 5/2011 |
| ES | 2364140 T3 | 8/2011 |
| IS | 8052 A | 9/2005 |
| JP | H04210916 A | 8/1992 |
| JP | 2007516241 A | 6/2007 |
| JP | 4027406 B2 | 12/2007 |
| JP | 2016506362 A | 3/2016 |

(Continued)

OTHER PUBLICATIONS

Moore et al; Neuropsychopharmacology Reviewes, 2013, vol. 38, pp. 23-28.*
Suzuki and Bird, Nature Reviews Genetics, vol. 9, 2008, pp. 465-476.*
Falkenberg et al., "Histone deacetylases and their inhibitors in cancer, neurological diseases and immune disorders," Nature Reviews Drug Discovery. 13 (9):673-691 (2014) (20 pages).
Frearson et al., "N-Myristoyltransferase inhibitors as new leads to treat sleeping sickness," Available in PMC Oct. 1, 2010, published in final edited form as: Nature. 464(7289): 728-732 (2010) (16 pages).

(Continued)

*Primary Examiner* — Jehanne S Sitton
(74) *Attorney, Agent, or Firm* — Clark & Elbing LLP

(57) ABSTRACT

The finding that multiple cancers lack one of two NMTs, while stromal and normal tissues do not, enables the treatment of NMT2-deficient cancer cells with an NMT inhibitor. It is shown herein that NMT2 expression is reduced or eliminated in certain cancers, and in one example lymphomas, via an epigenetic mechanism(s). Reduction or elimination of NMT2 expression renders the cancer sensitive inhibitors of NMT.

8 Claims, 20 Drawing Sheets

Specification includes a Sequence Listing.

(56) References Cited

FOREIGN PATENT DOCUMENTS

| WO | WO-2004/080976 A1 | 9/2004 |
|---|---|---|
| WO | WO-2005012305 A2 | 2/2005 |
| WO | WO-2005012524 A1 | 2/2005 |
| WO | WO-2005053662 A1 | 6/2005 |
| WO | WO-2005/076843 A2 | 8/2005 |
| WO | WO-2006014729 A2 | 2/2006 |
| WO | WO-2006086043 A2 | 8/2006 |
| WO | WO-2008076965 A1 | 6/2008 |
| WO | WO-2010026365 A1 | 3/2010 |
| WO | WO-2013/013302 A1 | 1/2013 |
| WO | WO-2013013302 A1 | 1/2013 |
| WO | WO-2014/067002 A1 | 5/2014 |

OTHER PUBLICATIONS

International Search Report and Written Opinion for International Patent Application No. PCT/CA2016/050846, dated Sep. 14, 2016 (15 pages).
International Preliminary Report on Patentability for International Patent Application No. PCT/CA2016/050846, dated Jan. 23, 2018 (9 pages).
Kuang et al., "Genome-wide identification of aberrantly methylated promoter associated CpG islands in acute lymphocytic leukemia," Leukemia. 22(8):1529-1538 (2008).
Lane et al., "Histone deacetylase inhibitors in cancer therapy," Journal of Clinical Oncology. 27(32):5459-5468 (2009) (10 pages).
Communication pursuant to Article 94(3) for European Patent Application No. 16826961.1, dated Dec. 4, 2019 (5 pages).
Office Action for Japanese Application No. 2018-502095, dated Jul. 6, 2020 (9 pages).
Extended European Search Report for European Patent Application No. 16826961.1, dated Dec. 5, 2018 (7 pages).
Selvakumar et al., "N-myristoyltransferase 2 Expression in Human Colon Cancer: Cross-Talk Between the Calpain and Caspase System," FEBS Lett. 580(8):2021-6 (2016).
Beauchamp et al., "Targeting N-Myristolation for Therapy of B-cell Lymphomas," Nat Commun. 11(1):5348 (2020) (46 pages).
Wright et al., "Validation of N-myristoyltransferase as an antimalarial drug target using an integrated chemical biology approach," Nat Chem. 6(2):112-121 (2014) (22 pages).
Goncalves et al., "Discovery of Plasmodium vivax N-Myristoyltransferase Inhibitors: Screening, Synthesis, and Structural Characterization of their Binding Mode," J Med Chem. 55(7):3578-82 (2012) (13 pages).
Rackham et al., "Discovery of Novel and Ligand-Efficient Inhibitors of Plasmodium falciparum and Plasmodium vivax N?Myristoyltransferase," J Med Chem., 56(1):371-375 (2013).
Aitken et al., "Identification of the NH2-Terminal Blocking Group of Calcineurin B as Myristic Acid," FEBS Letters, Dec. 1982, vol. 150 (2), pp. 314-318.
Alizadeh et al., "Distinct Types of Diffuse Large B-Cell Lymphoma Identified by Gene Expression Profiling," Nature, Feb. 2000, vol. 403 (6769), pp. 503-511.
Alland et al., "Dual Myristylation and Palmitylation of Src Family Member P59fyn Affects Subcellular Localization," Journal of Biological Chemistry, Jun. 1994, vol. 269 (24), pp. 16701-16705.
Armah et al., "S-Myristoylation of a Glycosylphosphatidylinositol-Specific Phospholipase C in Trypanosoma Brucei," The Journal of Biological Chemistry, Feb. 1999, vol. 274 (9), pp. 5931-5938.
Ashworth et al., "A Synthetic Lethal Therapeutic Approach: Poly(ADP) Ribose Polymerase Inhibitors for the Treatment of cancers Deficient in DNA Double-Strand Break Repair," Journal of Clinical Oncology, Aug. 2008, vol. 26 (22), pp. 3785-3790.
Australian Patent Application No. 2018202839, First Examination Report dated Mar. 29, 2019.
Australian Patent Application No. 2012286542, Office Action dated Apr. 5, 2018.
Australian Patent Application No. 2018203395, Examination Report dated Apr. 22, 2020.
Australian Patent Application No. 2012286542, Office Action dated Apr. 27, 2017.
Australian Patent Application No. 2013337569, Examination Report dated May 16, 2017.
Australian Patent Application No. AU2013337569, Examination Report dated May 2, 2019.
Barneda-Zahonero et al., "Histone Deacetylases and Cancer," Molecular Oncology, Dec. 2012, vol. 6 (6), pp. 579-589.
Barretina et al., "The Cancer Cell Line Encyclopedia Enables Predictive Modelling of Anticancer Drug Sensitivity," Nature, Mar. 2012, vol. 483 (7391), pp. 603-607.
Bereshchenko et al., "Acetylation Inactivates the Transcriptional Repressor BCL6," Nature Genetics, Dec. 2002, vol. 32 (4), pp. 606-613.
Berndt et al., "Targeting Protein Prenylation for Cancer Therapy," Nature Reviews Cancer, Oct. 2011, vol. 11 (11), pp. 775-791.
Berthiaume et al., "Synthesis and Use of Iodo-Fatty Acid Analogs," Methods in Enzymology, 1995, vol. 250, pp. 454-466.
Beveridge et al., "Economic Impact of Disease Progression in Follicular Non-Hodgkin Lymphoma," Leukemia and Lymphoma, Nov. 2011, vol. 52 (11), pp. 2117-2123.
Bhandarkar et al., "Tris (Dibenzylideneacetone) Dipalladium, a N-Myristoyltransferase-1 Inhibitor, is Effective Against Melanoma Growth in Vitro and in Vivo," Clinical Cancer Research, Sep. 2008, vol. 14 (18), pp. 5743-5748, XP055142988. Retrieved from Internet:[https://clincancerres.aacrjournals.org/content/clincanres/14/18/5743.short].
Bhatnagar et al., "Isothermal Titration Calorimetric Studies of Saccharomyces cerevisiae Myristoyl-CoA Protein N-Vlyristoyltransfera. Determinants of Binding Energy and Catalytic Discrimination among ACYL-CoA and Peptide Ligands," Journal of Biological Chemistry, Apr. 1994, vol. 269 (15), pp. 11045-11053.
Bhatnagar et al., "The Structure of Myristoyl-CoA Protein N-Myristoyltransferase," Biochimica Et Biophysica Acta, Nov. 1999, vol. 1441 (2-3), pp. 162-172.
Bhatnagar et al., "Structure of N-Myristoyltransferase With Bound Myristoylcoa and Peptide Substrate Analogs," Nature Structural Biology, Dec. 1998, vol. 5 (12), pp. 1091-1097.
Boisson et al., "Unexpected Protein Families Including Cell Defense Components Feature in the N-Myristoylome of a Higher Eukaryote," Journal of Biological Chemistry, Oct. 2003, vol. 278 (44), pp. 43418-43429.
Bokoch, "Biology of the p21-Activated Kinases," Annual Review of Biochemistry, 2003, vol. 72, pp. 743-781.
Bologna et al., "N-Terminal Myristoylation Predictions by Ensembles of Neural Networks," Proteomics, Jun. 2004, vol. 4 (6), pp. 1626-1632.
Bosch, "Is Endemic Burkitt's Lymphoma an Alliance Between Three Infections and a Tumour Promoter?," The Lancet Oncology, Dec. 2004, vol. 5 (12), pp. 738-746.
Boutin et al., "Myristoylation," Cell Signal, Jan. 1997, vol. 9 (1), pp. 15-35.
Bowyer et al., "N-Myristoyltransferase: a Prospective Drug Target for Protozoan Parasites," ChemMedChem, Mar. 2008, vol. 3 (3), pp. 402-408.
Brady et al., "Epstein-Barr Virus and Burkitt Lymphoma," Journal of Clinical Pathology, Dec. 2007, vol. 60 (12), pp. 1397-1402.
Brannigan et al., "N-Myristoyltransferase from Leishmania donovani: Structural and Functional Characterisation of a Potential Drug Target for Visceral Leishmaniasis," Journal of Molecular Biology, Mar. 2010, vol. 396 (4), pp. 985-999.
Bratton et al., "Apoptotic Death Sensor: an Organelle's Alter Ego?," Trends in Pharmacological Sciences, Jun. 2001, vol. 22 (6), pp. 306-315.
Brazil Patent Application No. 1120150096077, Office Action dated Aug. 30, 2019.
Brazilian Patent Application No. 112014001430-2, Office Action dated May 5, 2020.

(56) References Cited

OTHER PUBLICATIONS

Bryant et al., "Myristoylation-Dependent Replication and Assembly of Human Immunodeficiency Virus," Proceedings of the National Academy of Sciences of the United States of America, Jan. 1990, vol. 87 (2), pp. 523-527.
Bryant et al., "Specific Killing of BRCA2-deficient Tumours With Inhibitors of Poly(ADP-'ribose) Polymerase," Nature, Apr. 2005, vol. 434 (7035), pp. 913-917.
Buglino et al., "Hhat Is a Palmitoylacyltransferase with Specificity for N-Palmitoylation of Sonic Hedgeho," Journal of Biological Chemistry, Aug. 2008, vol. 283 (32), pp. 22076-22088.
Buglino et al., "Palmitoylation of Hedgehog Proteins," Vitamins and Hormones, 2012, vol. 88, pp. 229-252.
Burkitt, "A Sarcoma Involving the Jaws in African Children," British Journal of Surgery, Nov. 1958, vol. 46 (197), pp. 218-223.
Buss et al., "Direct Identification of Palmitic Acid as the Lipid Attached to p21ras," Molecular and Cellular Biology, Jan. 1986, vol. 6 (1), pp. 116-122.
Buss et al., "Myristic Acid Is Attached to the Transforming Protein of Rous Sarcoma Virus During or Immediately After Synthesis and Is Present in Both Soluble and Membrane-Bound Forms of the Protein," Molecular and Cellular Biology, Dec. 1984, vol. 4 (12), pp. 2697-2704.
Cabanillas, "Non-hodgkin's Lymphoma: the Old and the New," Clinical Lymphoma, Myeloma and Leukemia, Jun. 2011, vol. 11 (Suppl 1), pp. S87-S90.
Canadian Patent Application No. 2,842,443, Office Action dated May 9, 2018.
Canadian Patent Application No. 2,842,443, Office Action dated Nov. 15, 2019.
Canadian Patent Application No. 2,890,113, Office Action dated Oct. 10, 2019.
Canadian Cancer Society's Steering Committee on Cancer Statistics. Canadian Cancer Statistics 2011. Toronto, ON: Canadian Cancer Society, May 2011, 135 pages.
Canadian Patent Application No. 2,842,443, Office Action dated Jan. 28, 2019.
Canadian Patent Application No. 2,842,443, Office Action dated Jan. 22, 2021.
Canadian Patent Application No. 2,890,113, Office Action dated Jan. 26, 2021.
Carr et al., "N-tetradecanoyl Is the NH2-terminal Blocking Group of the Catalytic Subunit of Cyclic AMP-dependent Protein Kinase From Bovine Cardiac Muscle," Proceedings of the National Academy of Sciences of the United States of America, Oct. 1982, vol. 79 (20), pp. 6128-6131.
Charron et al., "Robust Fluorescent Detection of Protein Fatty-Acylation With Chemical Reporters," Journal of the American Chemical Society, Apr. 2009, vol. 131 (13), pp. 4967-4975.
Chen et al., "Regulation of G Proteins by Covalent Modification," Oncogene, Mar. 2001, vol. 20 (13), pp. 1643-1652.
Chen et al., "The Regulation of Autophagy-Unanswered Questions," Journal of Cell Science, Jan. 2011, vol. 124 (Pt 2), pp. 161-170.
Chinese Patent Application No. 201280046437.8, Office Action dated May 22, 2018.
Chinese Patent Application No. 201910841567.4, Office Action dated Sep. 30, 2019.
Chinese Patent Application No. 201910130300.4, Office Action dated Dec. 2, 2020.
Chinese Patent Application No. 201280046437.8, First Office Action dated Feb. 28, 2015.
Chinese Patent Application No. 201280046437.8, Second Office Action dated Jan. 8, 2016.
Chinese Patent Application No. 201280046437.8, Third Office Action dated Sep. 9, 2016.
Chinese Patent Application No. 201380056950.X, Office Action dated Nov. 3, 2017.
Chinese Patent Application No. 201910841567.4, Office Action dated Jun. 29, 2021.
Chinese Patent Application No. CN 201380056950.X, Office Action dated May 5, 2016.
Chinese Patent Application No. CN 201380056950.X, Office Action dated May 22, 2019.
Chinese Patent Application No. CN 201380056950.X, Second Office Action dated Feb. 27, 2017.
Chinese Patent Application No. CN2012846437, Office Action dated Jun. 12, 2017.
Choi et al., "N-Myristoylated c-Abl Tyrosine Kinase Localizes to the Endoplasmic Reticulum upon Binding to an 41losteric Inhibitor," The Journal of Biological Chemistry, Oct. 2009, vol. 284 (42), pp. 29005-29014.
Chou et al., "Quantitative Analysis of Dose-Effect Relationships: the Combined Effects of Multiple Drugs or Enzyme Inhibitors," Advances in Enzyme Regulation, 1984, vol. 22, pp. 27-55.
Cohen, "Caspases: The Executioners of Apoptosis," Biochemical Journal, Aug. 1997, vol. 326 ( Pt 1), pp. 1-16.
Cordeddu et al., "Mutation of SHOC2 Promotes Aberrant Protein N-Myristoylation and Causes Noonan-Like Syndrome with Loose Anagen Hair," Nature Genetics, Sep. 2009, vol. 41 (9), pp. 1022-1026.
Cordo et al., "Myristic Acid Analogs are Inhibitors of Junin Virus Replication," Microbes and Infection, Jul. 1999, vol. 1 (8), pp. 609-614.
Cory et al., "Use of an Aqueous Soluble Tetrazolium/Formazan Assay for Cell Growth Assays in Culture," Cancer Communication, Jul. 1991, vol. 3 (7), pp. 207-212.
Crawford et al., "Conservation of Caspase Substrates Across Metazoans Suggests Hierarchical Importance of Signaling Pathways Over Specific Targets and Cleavage Site Motifs in Apoptosis," Cell Death & Differentiation, Dec. 2012, vol. 19 (12), pp. 2040-2048.
Cross et al., "A Short Sequence in the p60src N Terminus Is Required for p60src Myristylation and Membrane Association and for Cell Transformation," Molecular and Cellular Biology, Sep. 1984, vol. 4 {9), pp. 1834-1842.
Dang et al., "c-Myc Target Genes Involved in Cell Growth, Apoptosis, and Metabolism," Molecular and Cellular Biology, Jan. 1999, vol. 19 (1), pp. 1-11.
Das et al., "Inhibition of Protein N-Myristoylation: A Therapeutic Protocol in Developing Anticancer Agents," Current Cancer Drug Targets, Apr. 2012, 12(6): 1-12.
Dave et al., "Molecular Diagnosis of Burkitt's Lymphoma," The New England Journal of Medicine, Jun. 2006, vol. 354 {23), pp. 2431-2442.
Dawson et al., "Cancer Epigenetics: from Mechanism to Therapy," Cell, Jul. 2012, vol. 150 {1), pp. 12-27.
De La Puent A et al., Tris DBA Palladium Overcomes Hypoxia Mediated Drug Resistance in Multiple Myeloma. Leuk Lymphoma, Jul. 2016, vol. 57 (7), pp. 1677-1686.
Deichaite et al., "In Vitro Synthesis of pp60v-src: Myristylation in a Cell-Free System," Molecular and Cellular Biology, Oct. 1988, vol. 8 (10), pp. 4295-4301.
Dekker et al., "Small-Molecule Inhibition of APT1 Affects Ras Localization and Signaling," Nature Chemical Biology, Jun. 2010, vol. 6 (6), pp. 449-456.
Devadas et al., "Design and Synthesis of Novel Imidazole-Substituted Dipeptide Amides as Potent and Selective nhibitors of Candida albicans MyristoylCoA:Protein N-Myristoyltransferase and Identification of Related Tripeptide Inhibitors with Mechanism-Based Antifungal Activity," Journal of Medicinal Chemistry, Aug. 1997, vol. 40 (16), pp. 2609-2625.
Devadas et al., "Substrate Specificity of *Saccharomyces cerevisiae* Myristoyi-CoA:Protein N-Myristoyltransferase. Analysis of Fatty Acid Analogs Containing Carbonyl Groups, Nitrogen Heteroatoms, and Nitrogen Heterocycles in an I Vitro Enzyme Assay and Subsequent Identification of Inhibitors of Human Immunodeficiency Virus I Replication," The Journal of Biological Chemistry, Apr. 1992, vol. 267 (11), pp. 7224-7239.
Disease Information. The Leukemia and Lymphoma Society, Search Disease Information. Accessed on Apr. 11, 2016 (1 page) [online]. Retrieved from the Internet: URL::http://www.lls.org.

(56) References Cited

OTHER PUBLICATIONS

Dix et al., "Global Mapping of the Topography and Magnitude of Proteolytic Events in Biological Systems," Cell, Aug. 2008, vol. 134 (4), pp. 679-691.
Draper et al., "Palmitoyl Acyltransferase Assays and Inhibitors ," Molecular Membrane Biology, Jan. 2009, vol. 26 (1), pp. 5-13.
Ducker et al., "Two N-Myristoyltransferase Isozymes Play Unique Roles in Protein Myristoylation, Proliferation, and Apoptosis," Molecular Cancer Research, Aug. 2005, vol. 3 (8), pp. 463-476. Retrieved from Internet:[http://mcr.aacrjournals.org/cgi/pmidlookup?view=long&pmid=16123142].
Duronio et al., "Disruption of the Yeast N-myristoyl Transferase Gene Causes Recessive Lethality," Science, Feb. 1989, vol. 243 (4892), pp. 796-800.
Duronio et al., "Mutations of Human Myristoyl-coa:protein N-Myristoyltransferase Cause Temperature-sensitive Myristic Acid Auxotrophy in *Saccharomyces cerevisiae*," Proceedings of the National Academy of Sciences of the United States of America, May 1992, vol. 89 (9), pp. 4129-4133.
Dyda et al., "GCN5-Related N-Acetyltransferases: A Structural Overview," Annual Review of Biophysics and Biomolecular Structure, 2000, vol. 29, pp. 81-103.
Eisenhaber et al., "Prediction of Lipid Posttranslational Modifications and Localization Signals From Protein Sequences: Dig-pi, NMT and PTS1," Nucleic Acids Research, Jul. 2003, vol. 31 (13), pp. 3631-3634.
Enari et al., "A Caspase-Activated Dnase That Degrades DNA During Apoptosis, and Its Inhibitor ICAD," Nature, Jan. 1998, vol. 391 (6662), pp. 43-50.
European Patent Application No. 12817041.2, Office Action dated Dec. 20, 2017.
European Patent Application No. 13852049.9, Office Action dated Nov. 20, 2018.
European Patent Application No. 12817041, Extended European Search Report dated Dec. 12, 2014.
European Patent Application No. 12817041, Supplementary European Search Report dated Feb. 26, 2015.
European Patent Application No. 13852049, Extended European Search Report dated Jun. 28, 2016.
European Patent Application No. 13852049, Partial European Search Report dated Feb. 25, 2016.
European Patent Application No. 13852049.9, Communication pursuant to Article 94(3) EPC dated Oct. 6, 2017.
European Patent Application No. 16826961.1, Communication pursuant to Article 94(3) EPC dated Feb. 23, 2021.
European Patent Application No. 20213908.5, Extended European Search Report dated Jun. 9, 2021.
Fadeel et al., "Apoptosis: a Basic Biological Phenomenon With Wide-Ranging Implications in Human Disease," Journal of Internal Medicine, Dec. 2005, vol. 258 (6), pp. 479-517.
Farazi et al., "The Biology and Enzymology of Protein N-Myristoylation," The Journal of Biological Chemistry, Oct. 2001, vol. 276 (43), pp. 39501-39504.
Farmer et al., "Targeting the Dna Repair Defect in Brea Mutant Cells as a Therapeutic Strategy," Nature, Apr. 2005, vol. 434 (7035), pp. 917-921.
FDA, Guidance for Industry and FDA Staff: Interpretation of the Term "Chemical Action" in the Definition of Device Under Section 201 (h) of the Federal Food, Drug, and Cosmetic Act. Accessed online at https://www.fda.gov/downloads/RegulatoryInformation/Guidances/UCM259068.pdf. Jun. 2011, 9 pages.
FDA, Information for Consumers (Biosimilars). Accessed online at https://www.fda.gov/Drugs/DevelopmentApprovaiProcess/HowDrugsareDevelopedandApproved/ApprovaiApplications/TherapeuticBiologicApplications/Biosimilars/ucm241718.html. page last updated Aug. 27, 2015, 5 pages.
Feinberg et al., "The History of Cancer Epigenetics," Nature Reviews Cancer, Feb. 2004, vol. 4(2), pp. 143-153.
Felsted et al., "Protein N-Myristoylation as a Chemotherapeutic Target for Cancer," Journal of the National Cancer Institute, Nov. 1995, vol. 87 (211), pp. 1571-1573.
Ferrara et al., "Cost-effectiveness Analysis of the Addition of Rituximab to CHOP in Young Patients With Good-prognosis Diffuse Large-B-cell Lymphoma," Clinical Drug Investigation, 2008, vol. 28(1), pp. 55-65.
Fong et al., "Inhibition of Poly(ADP-Ribose) Polymerase in Tumors From BRCA Mutation Carriers," The New England Journal of Medicine, Jul. 2009, vol. 361 (2), pp. 123-134.
Foon et al., "Novel Therapies for Aggressive B-cell Lymphoma," Advances in Hematology, 2012, vol. 2012, pp. 22.
Frottin et al., "The Proteomics of N-terminal Methionine Cleavage," Molecular Cellular Proteomics, Dec. 2006, vol. 5 (12), pp. 2336-2349.
Gamper et al., "Gene Expression Profile of Bladder Tissue of Patients with Ulcerative Interstitial Cystitis,"BMC Genomics, Apr. 28, 2009, vol. 10 (199), pp. 1-17.
Gatto et al., "The Germinal Center Reaction," The Journal of Allergy and Clinical Immunology, Nov. 2010, vol. 126 (5), pp. 898-907, quiz 908-9.
Giang et al., "A Second Mammalian N-Myristoyltransferase," The Journal of Biological Chemistry, Mar. 1998, vol. 273 (12), pp. 6595-6598.
Glover et al., "Human N-Myristoyltransferase Amino-terminal Domain Involved in Targeting the Enzyme to the Ribosomal Subcellular Fraction," The Journal of Biological Chemistry, Nov. 1997, vol. 272 (45), pp. 28680-28689.
Goncalves et al., "A Fluorescence-Based Assay for N-Myristoyltransferase Activity," Analytical Biochemistry, Feb. 2012, vol. 421 (1), pp. 342-344.
Griffin et al., "A Study of Rituximab and Ifosfamide, Carboplatin, and Etoposide Chemotherapy in Children with Recurrent/Refractory B-cell (CD20+) Non-Hodgkin Lymphoma and Mature B-Cell Acute Lymphoblastic Leukemia: A Report from the Children's Oncology Group," Pediatric Blood & Cancer, Feb. 2009, vol. 52 (2), pp. 177-181.
Gisselbrecht et al., "Salvage Regimens with Autologous Transplantation for Relapsed Large B-Cell Lymphoma in the Rituximab Era," Journal of Clinical Oncology, Sep. 2010, vol. 28 (27), pp. 4184-4190.
Gui et al., "Histone Deacetylase (HDAC) Inhibitor Activation of p21WAF1 Involves Changes in Promoter Associated Proteins, Including HDAC1," Proceedings of the National Academy of Sciences of the United States of America, Feb. 2004, vol. 101 (5), pp. 1241-1246.
Gutkowska et al., "Structure, Regulation and Cellular Functions of Rab Geranylgeranyl Transferase and Is Cellular Partner Rab Escort Protein," Molecular Membrane Biology, Nov. 2012, vol. 29 (7), pp. 243-256.
Hancock et al., "All Ras Proteins are Polyisoprenylated but Only Some are Palmitoylated," Cell, Jun. 1989, vol. 57 (7), pp. 1167-1177.
Hang et al., "Exploring Protein Lipidation With Chemical Biology," Chemical Reviews, Oct. 2011, vol. 111(10), pp. 6341-6358.
Hantschel et al., "A Myristoyl/Phosphotyrosine Switch Regulates c-Abl," Cell, Mar. 2003, vol. 112(6), pp. 845-857.
Harper et al., "Inhibition of Varicella-Zoster Virus Replication by an Inhibitor of Protein Myristoylation," The Journal of General Virology, Jun. 1993, vol. 74 (Pt 6), pp. 1181-1184.
Hedo et al., "Myristyl and Palmityl Acylation of the Insulin Receptor," The Journal of Biological Chemistry, Jan. 1987, vol. 262 (3), pp. 954-957.
Hobeika et al., "Testing Gene Function Early in the B Cell Lineage in Mb1-cre Mice.," Proceedings of the National Academy of Sciences of the United States of America, Sep. 2006, vol. 103 (37), pp. 13789-13794.
Hu et al., "Myristoylated Naked2 Antagonizes Wnt-beta-catenin Activity by Degrading Dishevelled-1 at the Plasma Membrane," The Journal of Biological Chemistry, Apr. 2010, vol. 285 (18), pp. 13561-13568.

(56) References Cited

OTHER PUBLICATIONS

Hummel et al., "A Biologic Definition of Burkitt's Lymphoma From Transcriptional and Genomic Profiling," The New England Journal of Medicine, Jun. 2006, vol. 354 (23), pp. 2419-2430.
Inoue et al., "Ordering of Caspases in Cells Undergoing Apoptosis by the Intrinsic Pathway," Cell Death and Differentiation, 2009, vol. 16 (7), pp. 1053-1061.
International Patent Application No. PCT/CA2012/000696, International Search Report dated Nov. 7, 2012.
International Patent Application No. PCT/CA2013/050821, International Search Report dated Feb. 5, 2014.
Israel Patent Application No. 230575, Office Action dated May 23, 2018.
Israel Patent Application No. 230575, Office Action dated Jan. 8, 2020.
Israel Patent Application No. 230575, Office Action dated Apr. 25, 2021.
Israel Patent Application No. IL230575, Office Action dated Dec. 11, 2016.
Israeli Patent Application No. 238481, Office Action dated Nov. 6, 2017.
Japanese Patent Application No. 2014-520475, Notice of Allowance dated Dec. 4, 2017.
Iversen et al., "Cell Kinetics of African Cases of Burkitt Lymphoma. A Preliminary Report," European Journal of Cancer, Jun. 1972, vol. 8 (3), pp. 305-308.
Jackson et al., "N-Terminal Mutations Activate the Leukemogenic Potential of the Myristoylated form of c-abl," The EMBO Journal, Feb. 1989, vol. 8 (2), pp. 449-456.
Jaffe, "The 2008 WHO Classification of Lymphomas: Implications for Clinical Practice and Translational Research," Hematology-American Society of Hematology Education Program, 2009, pp. 523-531.
Jakobi., "Subcellular Targeting Regulates the Function of Caspase-Activated Protein Kinases in Apoptosis," Drug Resistance Updates, Feb. 2004, vol. 7 (1), pp. 11-17.
Japanese Patent Application No. 2014-520475, Office Action dated May 9, 2016.
Japanese Patent Application No. 2015-0538225, Office Action dated Jul. 10, 2017.
Japanese Patent Application No. 2015-0538225, Office Action dated May 21, 2018.
Japanese Patent Application No. 2018-502095, Office Action dated Jun. 21, 2021.
Juo et al., "Essential Requirement for Caspase-8/FLICE in the Initiation of the Fas-Induced Apoptotic Cascade," Current Biology, Sep. 1998, vol. 8 (18), pp. 1001-1008.
Kaelin., "The Concept of Synthetic Lethality in the Context of Anticancer Therapy," Nature Reviews Cancer, Sep. 2005, vol. 5 (9), pp. 689-698.
Kagawa et al., "Deficiency of Caspase-3 in MCF7 Cells Blocks Bax-mediated Nuclear Fragmentation but not Cell Death," Clinical Cancer Research, May 2001, vol. 7 (5), pp. 1474-1480.
Kamps et al., "Mutation of NH2-Terminal Glycine of p60src Prevents Both Myristoylation and Morphological Transformation," Proceedings of the National Academy of Sciences, Jul. 1985, vol. 82(14), pp. 4625-4628.
Kasahara et al., "Rapid Trafficking of C-Src, a Non-Palmitoylated Src-Family Kinase, Between the Plasma Membrane and Late Endosomes/Lysosomes," Experimental Cell Research, Jul. 2007, vol. 313 (12), pp. 2651-2666.
Kay et al., "Tris (Dibenzylideneacetone) Dipalladium a Small-Molecule Palladium Complex Is Effective in the Induction of Apoptosis for B-Chronic Lymphocytic Leukemia B-Cells," Blood, Dec. 2011, vol. 118, pp. 2851. [retrieved on Feb. 17, 2016] Retrieved from Internet:[https://ash.confex.com/ash/2011/webprogram/Paper37660.html], XP055250861.
Kelly et al., "Burkitt Lymphoma: Revisiting the Pathogenesis of a Virus-Associated Malignancy," Hematology American Society of Hematology Education Program, 2007, vol. 1, pp. 277-284.
Kenkre et al., "Burkitt Lymphoma/Leukemia: Improving Prognosis," Clinical Lymphoma, Myeloma & Leukemia Supplement, 2009, vol. 9 Suppl 3, pp. 3231-3238.
Kim et al., "Src Kinases as Therapeutic Targets for Cancer," Nature Reviews Clinical Oncology, Oct. 2009, vol. 6 (10), pp. 587-595.
King et al., "Demonstration of Multiple Forms of Bovine Brain Myristoyl Coa:Protein N-Myristoyl Transferase," Molecular and Cellular Biochemistry, Jul. 1992, vol. 113 (1), pp. 77-81.
King et al., "Identification, Purification and Characterization of a Membrane-Associated N-Myristoyltransferase Inhibitor Protein from Bovine Brain," Biochemical Journal, Apr. 1993, vol. 291 (Pt2), pp. 635-639.
King et al., "N-Myristoyl Transferase Assay Using Phosphocellulose Paper Binding," Analytical Biochemistry, Dec. 1991, vol. 199 (2), pp. 149-153.
Kishore et al., "The Substrate Specificity of *Saccharomyces cereuisiae* Myristoyl-CoA: Protein N-Myristoyltransferase. Analysis of Myristic Acid Analogs Containing Oxygen, Sulfur, Double Bonds, Triple Bonds, and/or an Aromatic Residue," The Journal of Biological Chemistry, May 1991, vol. 266 (14), pp. 8835-8855.
Kojima et al., "Ghrelin is a Growth-Hormone-Releasing Acylated Peptide from Stomach," Nature, Dec. 1999, vol. 402 (6762), pp. 656-660.
Kon et al., "Chaperone-Mediated Autophagy in Health and Disease," FEBS Letters, Apr. 2010, vol. 584(7), pp. 1399-1404.
Korean Patent Application No. 10-2014-7004635, Office Action dated Oct. 16, 2018.
Korean Patent Application No. 10-2015-7014547, Office Action dated Feb. 22, 2021.
Korean Patent Application No. 10-2014-7004635, Office Action dated Sep. 6, 2019.
Korean Patent Application No. 10-2015-7014547, Office Action dated Mar. 6, 2020.
Korean Patent Application No. 10-2014-7004635, Office Action dated May 27, 2019.
Korycka et al., "Human DHHC Proteins: A Spotlight on the Hidden Player of Palmitoylation," The European Journal of Cell Biology, Feb. 2012, vol. 91 (2), pp. 107-117.
Kostiuk et al., "Identification of Palmitoylated Mitochondrial Proteins Using a Bio-orthogonal Azido-palmitate Analogue," FASEB Journal, Mar. 2008, vol. 22 (3), pp. 721-732.
Kovalchuk et al., "Burkitt Lymphoma in the Mouse," The Journal of Experimental Medicine, Oct. 2000, vol. 192 (8), pp. 1183-1190.
Kumar et al., "The Potential Use of N-Myristoyltransferase as a Biomarker in the Early Diagnosis of Colon Cancer," Cancers (Basel), Mar. 2011, vol. 3 (1), pp. 1372-1382.
Kuppers, "Mechanisms of B-cell Lymphoma Pathogenesis," Nature Reviews Cancer, Apr. 2005, vol. 5 (4), pp. 251-262.
Laemmli, "Cleavage of Structural Proteins During the Assembly of the Head of Bacteriophage T4," Nature, Aug. 1970, vol. 227 (5259), pp. 680-685.
Leatherbarrow, "Grafit User's Guide (Version 6)," Erithacus Software Ltd., Horley, United Kingdom. 2009, pp. 1-294.
Lee, "A Capacitance-Based Method for Experimental Determination of Metallurgical Channel Length of Submicron LDD MOSFET's," IEEE Transactions on Electron Devices, Mar. 1994, vol. 41 (3), pp. 403-412.
Lee et al., "Costs Associated with Diffuse Large B-Cell Lymphoma Patient Treatment in a Canadian Integrated Cancer are Center," Value Health, Mar.-Apr. 2008, vol. 11 (2), pp. 221-230.
Lee et al., "Prognosis of Chronic Lymphocytic Leukemia: a Multivariate Regression Analysis of 325 Untreated Patients," Blood, Mar. 1987, vol. 69 (3), pp. 929-936.
Lenz et al., "Aggressive Lymphomas," The New England Journal of Medicine, Apr. 2010, vol. 362(15), pp. 1417-1429.
Leuenroth et al., "The Loss of Mcl-1 Expression in Human Polymorphonuclear Leukocytes Promotes Apoptosis," Journal of Leukocyte Biology, Jul. 2000, vol. 68 (1), pp. 158-166.
Liang et al., "Mass Spectrometric Analysis of GAP-43/neuromodulin Reveals the Presence of a Variety of Fatty Acylated Species," The Journal of Biological Chemistry, Sep. 2002, vol. 277 (36), pp. 33032-33040.

(56) References Cited

OTHER PUBLICATIONS

Liang et al., "The N-Terminal SH4 Region of the Src Family Kinase Fyn Is Modified by Methylation and Heterogeneous Fatty Acylation: Role in Membrane Targeting, Cell Adhesion, and Spreading," The Journal of Biological Chemistry, Feb. 2004, vol. 279 (9), pp. 8133-8139.

Lim et al, (Abstract) P004:Understanding the roles of NMT1 and NMT2 cancers. Accessed online at https://www.biochemistry.org/Portals/O/Conferences/Abstracts/SA164/SA164P004.pdf on Mar. 10, 2017, 1 page.

Lin et al., "Protein Lysine Acylation and Cysteine Succination by Intermediates of Energy Metabolism," ACS Chemical Biology, Jun. 2012, vol. 7 (6), pp. 947-960.

Liston et al., "The Inhibitors of Apoptosis: There is More to Life Than Bcl2," Oncogene, Nov. 2003, vol. 22 (53), pp. 8568-8580.

Liu et al., "Targeting the Protein Prenyltransferases Efficiently Reduces Tumor Development in Mice With K-RAS-Induced Lung Cancer," Proceedings of the National Academy of Sciences of the United States of America, Apr. 2010, vol. 107 (14), pp. 6471-6476.

Lobo et al., "Identification of a Ras Palmitoyltransferase in *Saccharomyces cerevisiae*," The Journal of Biological Chemistry, Oct. 2002, vol. 277 (43), pp. 41268-41273.

Lodge et al., "Comparison of Myristoyl-CoA Protein N-Myristoyltransferases from Three Pathogenic Fungi: Cryptococcus Neoformans," The Journal of Biological Chemistry, Jan. 1994, vol. 269 (4), pp. 2996-3009.

Lodge et al., "Targeted Gene Replacement Demonstrates That Myristoyl-CoA: Protein N-myristoyltransferase is Essential for Viability of Cryptococcus Neoformans," Proceedings of the National Academy of Sciences of the United States of America, Dec. 1994, vol. 91 (25), pp. 12008-12012.

Love et al., "The Genetic Landscape of Mutations in Burkitt Lymphoma," Nature Genetics, Dec. 2012, vol. 44 (12), pp. 1321-1325.

Lu et al., "Expression of N-myristoyltransferase in Human Brain Tumors," Neurochemical Research, Jan. 2005, vol. 30 (1), pp. 9-13. Retrieved from Internet:[http:https://www.ncbi.nlm.nih.gov/pubmed?term=((%22Neurochemical%20research%22%5BJournal%5D)%20AND%20lu%5BAuthor%5D)%20AND%20myristoyltransferase%5BTitle%2FAbstract%5D].

Luciano et al., "Phosphorylation of Bim-el by Erk1/2 on Serine 69 Promotes Its Degradation via the Proteasome Pathway and Regulates Its Proapoptotic Function," Oncogene, Oct. 2003, vol. 22 (43), pp. 6785-6793.

Lueg et al., "N-myristoyltransferase Inhibition Is Synthetic Lethal in MYC-Deregulated Cancers," BioRxiv, Mar. 20, 2021,25 pages, Retrieved from [URL:https://doi.org/10.1101/2021.03.20.436222].

Mackey et al., "N-Myristoyltransferase Proteins in Breast Cancer: Prognostic Relevance and Validation as a New Drug Target," Breast Cancer Research and Treatment, Jan. 2021, 7 pages.

Magee et al., "Fatty Acylation and Prenylation of Proteins: What's Hot in Fat," Current Opinion in Cell Biology, Apr. 2005, vol. 17 (2), pp. 190-196.

Magnuson et al., "Increased N-Myristoyltransferase Activity Observed in Rat and Human Colonic Tumors," Journal of the National Cancer Institute, Nov. 1995, vol. 87 (21), pp. 1630-1635.

Mahrus et al., "Global Sequencing of Proteolytic Cleavage Sites in Apoptosis by Specific Labeling of Protein N Termini," Cell, Sep. 2008, vol. 134 (5), pp. 866-876.

Mann et al., "Novel Lipid Modifications of Secreted Protein Signals," Annual Review of Biochemistry, 2004, vol. 73, pp. 891-923.

Martin et al., "Large-Scale Profiling of Protein Palmitoylation in Mammalian Cells," Nature Methods, Feb. 2009, vol. 6 (2), pp. 135-138.

Martin et al., "Post-Translational Myristoylation: Fat Matters in Cellular Life and Death," Biochimie, Jan. 2011, vol. 93 (1), pp. 18-31.

Martin et al., "Rapid Detection, Discovery, and Identification of Post-translationally Myristoylated Proteins During Apoptosis Using a Bio-orthogonal Azidomyristate Analog," FASEB Journal, Mar. 2008, vol. 22 (3), pp. 797-806.

Martin et al., "Tandem Reporter Assay for Myristoylated Proteins Post-translationally (TRAMPP) Identifies Novel Substrates for Post-Translational Myristoylation: PKCK, a Case Study," FASEB Journal, Jan. 2012, vol. 26 (1), pp. 13-28.

Massadi et al., "Ghrelin Acylation and Metabolic Control," Peptides, Nov. 2011, vol. 32 (11), pp. 2301-2308.

Matheson et al., "The Conservation of Amino Acids in the N-Terminal Position of Ribosomal and Cytosol Proteins from *Escherichia coli*, Bacillus Stearothermophilus, and Halobacterium Cutirubrum," Canadian Journal of Biochemistry, Dec. 1975, vol. 53 (12), pp. 1323-1327.

Maurer-Stroh et al., "N-Terminal N-Myristoylation of Proteins: Prediction of Substrate Proteins from Amino Acid Sequence," Journal of Molecular Biology, Apr. 2002, vol. 317 (4), pp. 541-557.

Maurer-Stroh et al., "N-Terminal N-Myristoylation of Proteins: Refinement of the Sequence Motif and its Taxon- Specific Differences," Journal of Molecular Biology, Apr. 2002, vol. 317 (4), pp. 523-540.

Maurer-Stroh et al., "Refinement and Prediction of Protein Prenylation Motifs," Genome Biology, 2005, vol. 6 (6), pp. R55.

Mayor et al., "Sorting GPI-Anchored Proteins," Sorting GPI-Anchored Proteins, Feb. 2004, vol. 5(2), pp. 110-120.

McCabe et al., "Functional Roles for Fatty Acylated Amino-terminal Domains in Subcellular Localization," Molecular Biology of the Cell, Nov. 1999, vol. 10 (11), pp. 3771-3786.

McCabe et al., "N-Terminal Protein Acylation Confers Localization to Cholesterol, Sphingolipid-enriched Membranes But Not to Lipid Rafts/Caveolae," Molecular Biology of the Cell, Nov. 2001, vol. 12(11), pp. 3601-3617.

McIlhinney et al., "Characterization and Cellular Localization of Human Myristoyl-Coa: Protein N-Myristoyltransferase," Biochemical Society Transactions, Aug. 1995, vol. 23 (3), pp. 549-553.

McIlhinney et al., "Immunocytochemical Characterization and Subcellular Localization of Human Vlyristoyl-CoA: Protein N-Myristoyltransferase in HeLa Cells.," Experimental Cell Research, Mar. 1996, vol. 223 (2), pp. 348-356.

McIlhinney et al., "Purification and Partial Sequencing of Myristoyl-CoA: Protein N-Myristoyltransferase from Bovine Drain," Biochemical Journal, Mar. 1993, vol. 290 (Pt 2), pp. 405-410.

McLaughlin et al., "The Myristoyl-Electrostatic Switch: A Modulator of Reversible Protein-Membrane Nteractions," Trends in Biochemical Sciences, Jul. 1995, vol. 20 (7), pp. 272-276.

McTaggart, "Isoprenylated Proteins," Cellular and Molecular Life Sciences, Feb. 2006, vol. 63 (3), pp. 255-267.

Merck Manual, 18th Edition, Japanese Edition, Nikkei BP, Apr. 25, 2007, pp. 1177-1186.

Mexican Patent Application No. MX/a/2015/005441, Office Action dated Dec. 7, 2018.

Mexican Patent Application No. MX/a/2014/000661, Office Action dated Aug. 7, 2018.

Mexican Patent Application No. 20140000661, Office Action dated Mar. 8, 2017.

Mexican Patent Application No. MX/a/2014/000661, Office Action dated Nov. 6, 2017.

Miles et al., "Risk Factors and Treatment of Childhood and Adolescent Burkitt Lymphoma/Leukaemia," British Journal of Haematology, Mar. 2012, vol. 156 (6), pp. 730-743.

Mishkind, "Morbid Myristoylation," Trends in Cell Biology, May 2001, vol. 11 (5), pp. 191.

Mitchell et al., "Protein Palmitoylation by a Family of Dhhc Protein S-Acyltransferases," Journal of Lipid Research, Jun. 2006, vol. 47 (6), pp. 1118-1127.

Moffitt et al., "From Sentencing to Execution—The Processes of Apoptosis," The Journal of Pharmacy and Pharmacology, May 2010, vol. 62 (5), pp. 547-562.

Molyneux et al., "Burkitt's Lymphoma," Lancet (London, England), Mar. 2012, vol. 379 (9822), pp. 1234-1244.

(56) References Cited

OTHER PUBLICATIONS

Morgan et al., "Modulation of Anthracycline-Induced Cytotoxicity by Targeting the Prenylated Proteome in Myeloid Leukemia Cells," Journal of Molecular Medicine (Berlin, Germany), Feb. 2012, vol. 90 (2), pp. 149-161.
Nagata, "Apoptotic DNA Fragmentation," Experimental Cell Research, Apr. 2000, vol. 256 (1), pp. 12-18.
New Zealand Patent Application No. 707090, Examination Report dated Mar. 20, 2018.
New Zealand Patent Application No. 707090, Office Action dated Nov. 13, 2018.
New Zealand Patent Application No. 737605, Examination Report dated Apr. 12, 2018.
New Zealand Patent Application No. 620167, First Examination Report dated Nov. 24, 2014.
New Zealand Patent Application No. 720441, First Examination Report dated May 25, 2016.
Nimchuk et al., "Eukaryotic Fatty Acylation Drives Plasma Membrane Targeting and Enhances Function of Several Type III Effector Proteins From Pseudomonas Syringae," Cell, May 2000, vol. 101 (4), pp. 353-363.
Novelli et al., "Protein Farnesylation and Disease," Journal of Inherited Metabolic Disease, Sep. 2012, vol. 35 (5), pp. 917-926.
Ntwasa et al., "*Drosophila* Embryos Lacking N-myristoyltransferase Have Multiple Developmental Defects," Experimental Cell Research, Jan. 2001, vol. 262 (2), pp. 134-144.
Ntwasa et al., "Sequence and Expression of *Drosophila* Myristoyl-CoA: Protein N-Myristoyl Transferase: Evidence for Proteolytic Processing and Membrane Localisation," Journal of Cell Science, Jan. 1997, vol. 110 (Pt 2), pp. 149-156.
Ohno et al., "Intracellular Localization and Tissue-Specific Distribution of Human and Yeast DHHC Cysteine-Rich Domain-Containing Proteins," Biochimica et Biophysica Acta, Apr. 2006, vol. 1761 (4), pp. 474-483.
Olsson et al., "Caspases and Cancer," Cell Death and Differentiation, Sep. 2011, vol. 18 (9), pp. 1441-1449.
Paige et al., "Metabolic Activation of 2-Substituted Derivatives of Myristic Acid To Form Potent Inhibitors of Myristoyl CoA:Protein N-Myristoyltransferase," Biochemistry, Nov. 1990, vol. 29 (46), pp. 10566-10573.
Panethymitaki et al., "Characterization and Selective Inhibition of Myristoyl-CoA:protein N-myristoyltransferase From Trypanosoma Brucei and Leishmania Major," The Biochemical Journal, Jun. 2006, vol. 396 (2), pp. 277-285.
Parekh et al., "Therapeutic Targeting of the BCL6 Oncogene for Diffuse Large B-cell Lymphomas," Leukemia and Lymphoma, May 2008, vol. 49 (5), pp. 874-882.
Patwardhan et al., "Myristoylation and Membrane Binding Regulate c-Src Stability and Kinase Activity," Molecular and Cellular Biology, Sep. 2010, vol. 30 (17), pp. 4094-4107.
Paulick et al., "The Glycosylphosphatidylinositol Anchor: A Complex Membrane-Anchoring Structure for Proteins," Biochemistry, Jul. 2008, vol. 47 (27), pp. 6991-7000.
Pegram et al., "Rational Combinations of Trastuzumab With Chemotherapeutic Drugs Used in the Treatment of Breast Cancer," Journal of the National Cancer Institute, May 2004, vol. 96 (10), pp. 739-749.
Peitzsch et al., "Binding of Acylated Peptides and Fatty Acids to Phospholipid Vesicles: Pertinence to Myristoylated Proteins," Biochemistry, Oct. 1993, vol. 32 (39), pp. 10436-10443.
Perinpanayagam et al., "Regulation of Co- And Post-Translational Myristoylation of Proteins During Apoptosis: Interplay of N-Myristoyltransferases and Caspases," The FASEB Journal, Feb. 2013, vol. 27 (2), pp. 811-821.
Perkins et al., "Burkitt Lymphoma in Adults," Hematology American Society of Hematology Education Program, 2008, pp. 341-348.
Peseckis et al., "Fatty Acyl Transfer by Human N-Myristyl Transferase Is Dependent Upon Conserved Cysteine and Histidine Residues," The Journal of Biological Chemistry, Dec. 1994, vol. 269 (49), pp. 30888-30892.
Peseckis et al., "Iodinated Fatty Acids as Probes for Myristate Processing and Function. Incorporation into pp60v-src.1," The Journal of Biological Chemistry, Mar. 1993, vol. 268 (7), pp. 5107-5114.
Phan et al., "The BCL6 Proto-Oncogene Suppresses P53 Expression in Germinal-Centre B Cells," Nature, Dec. 2004, vol. 432 (7017), pp. 635-639.
Podell, "Predicting N-Terminal Myristoylation Sites in Plant Proteins," BMC Genomics. Jun. 2004, 17 (51): 37.
Porter et al., "Cholesterol Modification of Hedgehog Signaling Proteins in Animal Development," Science, Oct. 1996, vol. 274 (5285), pp. 255-259.
Prasad et al., "N-Myristoyltransferase: A Novel Target," Mini-Reviews in Medicinal Chemistry, Feb. 2008, vol. 8 (2), pp. 142-149.
Price et al., "Myristoyl-CoAProtein N-Myristoyltransferase, an Essential Enzyme and Potential Drug Target in Kinetoplastid Parasites," The Journal of Biological Chemistry, Feb. 2003, vol. 278 (9), pp. 7206-7214.
Puente et al.,"Tris DBA Palladium Overcomes Hypoxia Mediated Drug Resistance in Multiple Myeloma, "Journal of Blood, 2015, p. 2978.
Rajala et al., "Increased Expression of N-Myristoyltransferase in Gallbladder Carcinomas," Cancer, May 2000, vol. 88 (9), pp. 1992-1999.
Raju et al., "Molecular Cloning and Biochemical Characterization of Bovine Spleen Myristoyl CoA:Protein N- Vlyristoyltransferase," Archives Biochemistry Biophysics, Dec. 1997, vol. 348(1), pp. 134-142.
Raju et al., "N-Myristoyltransferase Overexpression in Human Colorectal Adenocarcinomas," Experimental Cell Research, Aug. 1997, vol. 235 (1), pp. 145-154.
Raju et al., "Preparation and Assay of Myristoyl-CoAProtein N-Myristoyltransferase," Methods in Molecular Biology, 1999, vol. 116, pp. 193-211.
Rasti et al., "Circulating Epstein-Barr Virus in Children Living in Malaria-Endemic Areas," Scandinavian Journal of Immunology, May 2005, vol. 61 (5), pp. 461-465.
Resh, "Fatty Acylation of Proteins: New Insights into Membrane Targeting of Myristoylated and Palmitoylated Proteins," Biochimica et Biophysica Acta, Aug. 1999, vol. 1451 (1), pp. 1-16.
Resh, "Myristylation and Palmitylation of Src Family Members: The Fats of the Matter," Cell, Feb. 1994, vol. 76 (3), pp. 411-413.
Resh, "Palmitoylation of Ligands, Receptors, and Intracellular Signaling Molecules," Science's STKE : Signal Transduction Knowledge Environment, Oct. 2006, vol. 2006 (359), pp. re14.
Resh, "Trafficking and Signaling by Fatty-Acylated and Prenylated Proteins," Nature Chemical Biology, Nov. 2006, vol. 2 (11), pp. 584-590.
Richter-Larrea et al., "Reversion of Epigenetically Mediated BIM Silencing Overcomes Chemoresistance in Burkitt Lymphoma," Blood, Oct. 2010, vol. 116 (14), pp. 2531-2542.
Rioux et al., "Identification and Characterization of Recombinant and Native Rat Myristoyl-coa: Protein N-Myristoyltransferases," Molecular and Cellular Biochemistry, Jun. 2006, vol. 286 (1-2), pp. 161-170.
Rocks et al., "An Acylation Cycle Regulates Localization and Activity of Palmitoylated Ras Isoforms," Science, Mar. 2005, vol. 307 (5716), pp. 1746-1752.
Rocque et al., "A Comparative Analysis of the Kinetic Mechanism and Peptide Substrate Specificity of Human and *Saccharomyces cerevisiae* Myristoyl-CoAProtein N-Myristoyltransferase," The Journal of Biological Chemistry, May 1993, vol. 268 (14), pp. 9964-9971.
Roskoski, "Protein Prenylation: A Pivotal Posttranslational Process," Biochemical and Biophysical Research Communications, Mar. 2003, vol. 303 (1), pp. 1-7.
Rostovtsev et al., "A Stepwise Huisgen Cycloaddition Process: Copper(I)-Catalyzed Regioselective Ligation" of Azides and Terminal Alkynes, Angewandte Chemie (International ed. in English), Jul. 2002, vol. 41 (14), pp. 2596-2599.
Rouleau et al., "PARP Inhibition: PARP1 and Beyond," Nature Reviews Cancer, Apr. 2010, vol. 10(4), pp. 293-301.

(56) References Cited

OTHER PUBLICATIONS

Rudel et al., "Membrane and Morphological Changes in Apoptotic Cells Regulated by Caspase-mediated Activation of PAK2," Science, 1997, vol. 276 (5318), pp. 1571-1574.
Rudnick et al., "Analogs of Palmitoyl-CoA That Are Substrates for Myristoyl-coa:protein N-Myristoyltransferase," Proceedings of the National Academy of Sciences of the United States of America, Nov. 1992, vol. 89 (21), pp. 10507-10511.
Rudnick et al., "Kinetic and Structural Evidence for a Sequential Ordered Bi Bi Mechanism of Catalysis by *Saccharomyces cerevisiae* Myristoyl-CoA: Protein N-Myristoyltransferase," The Journal of Biological Chemistry, May 1991, vol. 266 (15), pp. 9732-9739.
Rudnick et al., "Studies of the Catalytic Activities and Substrate Specificities of *Saccharomyces cerevisiae* Myristoyl-menzyme A:Protein N-Myristoyltransferase Deletion Mutants and Human/Yeast Nmt Chimeras in *Escherichia coli* and *S. Cerevisiae*," The Journal of Biological Chemistry, Nov. 1992, vol. 267 (33), pp. 23852-23861.
Russian Patent Application No. 2014101787, Office Action dated Jun. 27, 2018.
Russian Patent Application No. 2015118294, Notice of Allowance dated Oct. 23, 2018.
Russian Patent Application No. 2014101787, Office Action dated Apr. 28, 2016.
Russian Patent Application No. 2014101787, Office Action dated Aug. 30, 2016.
Russian Patent Application No. 2014101787, Office Action dated Dec. 21, 2017.
Russian Patent Application No. RU2015118294, Office Action dated Jul. 7, 2017.
Ryan et al., "Hedgehog Secretion and Signal Transduction in Vertebrates," The Journal of Biological Chemistry, May 2012, vol. 287 (22), pp. 17905-17913.
Saini et al., "Rituximab in Hodgkin Lymphoma: Is the Target Always a Hit?," Cancer Treatment Reviews, Aug. 2011, vol. 37 (5), pp. 385-390.
Sakurai et al., "Posttranslational N-myristoylation Is Required for the Anti-apoptotic Activity of Human TGelsolin, the C-terminal Caspase Cleavage Product of Human Gelsolin," The Journal of Biological Chemistry, May 2006, vol. 281 (20), pp. 14288-14295.
Sato et al., "Differential Trafficking of Src, Lyn, Yes and Fyn Is Specified by the State of Palmitoylation in the SH4 Domain," Journal of cell science, Apr. 2009, vol. 122 (Pt 7), pp. 965-975.
Schey et al., "Novel Fatty Acid Acylation of Lens Integral Membrane Protein Aquaporin-0," Biochemistry, 2010, vol. 49 (45), pp. 9858-9865.
Schmidt-Supprian et al., "Excision of the Frt-flanked Neor Cassette From the CD19cre Knock-in Transgene Reduces 2, Re-Mediated Recombination," Transgenic Research, Oct. 2007, vol. 16(5), pp. 657-660.
Seaton et al., "N-Myristoyltransferase Isozymes Exhibit Differential Specificity for Human Immunodeficiency Virus Type 1 Gag and Nef," The Journal of General Virology, Jan. 2008, vol. 89 (Pt 1), pp. 288-296.
SEER Cancer Statistics Review 1975-2010, [online]. URL: http://seer.cancer.govicsr/1975_2010/results_single/sect_01_table.01_pdf, 86 pages.
Sehn et al., "Treatment of Aggressive Non-hodgkin's Lymphoma: A North American Perspective," Oncology, Apr. 2005, vol. 19 (4 Suppl 1), pp. 26-34.
Selvakumar et al., "Potential Role of N-Myristoyltransferase in Cancer," Progress in Lipid Research, Jan. 2007, vol. 46 (1), pp. 1-36. Retrieved from Internet:[https://www.sciencedirect.com/science/article/abs/pii/S0163782706000336?via%3Dihub] XP005776871, ISSN: 0163-7827, DOI: 10.1016/J.PLIPRES.
Shawgo et al., "Caspase-9 Activation by the Apoptosome Is Not Required for Fas-mediated Apoptosis in Type II Jurkat Cells," The Journal of Biological Chemistry, Nov. 2009, vol. 284 (48), pp. 33447-33455.
Sheng et al., "Homology Modeling and Molecular Dynamics Simulation of N-Myristoyltransferase From Protozoan Parasites: Active Site Characterization and Insights Into Rational Inhibitor Design," Journal of Computer-Aided Molecular Design, Jun. 2009, vol. 23 (6), pp. 375-389.
Shrivastav et al., "Overexpression of Akt/PKB Modulates N-myristoyltransferase Activity in Cancer Cells," The Journal of Pathology, Jul. 2009, vol. 218 (3), pp. 391-398.
Shrivastav et al., "Potent Inhibitor of N-myristoylation: a Novel Molecular Target for Cancer," Cancer Research, Nov. 2003, vol. 63 (22), pp. 7975-7978.
Shrivastav et al., "Regulation of N-Myristoyltransferase by Novel Inhibitor Proteins," Cell Biochemistry and Biophysics, Jan. 2005, vol. 43 (1), pp. 189-202. XP055143026. Retrieved from Internet:[http://dx.doi.org/10.1385/CBB:43:1:189].
Sigal et al., "Amino-terminal Basic Residues of Src Mediate Membrane Binding Through Electrostatic Interaction With Acidic Phospholipids," Proceedings of the National Academy of Sciences of the United States of America, Dec. 1994, vol. 91 (25), pp. 12253-12257.
Sikorski et al., "Selective Peptidic and Peptidomimetic Inhibitors of Candida albicans MyristoylCoA: Protein N- Mlyristoyltransferase: A New Approach to Antifungal Therapy," Biopolymers, 1997, vol. 43 (1), pp. 43-71.
Silverman et al., "Lysine Residues Form an Integral Component of a Novel NH2-Terminal Membrane Targeting Motif for Myristylated pp60v-src," The Journal of Cell Biology, Oct. 1992, vol. 119(2), pp. 415-425.
Singapore Patent Application No. SG10201703505V, Search Report and Written Opinion dated Mar. 22, 2021.
Singh et al., "Autophagy Regulates Lipid Metabolism," Nature, Apr. 2009, vol. 458 (7242), pp. 1131-1135.
Sjogren et al., "Inactivating GGTase-l Reduces Disease Phenotypes in a Mouse Model of K-RAS-lnduced Myeloproliferative Disease," Leukemia, Jan. 2011, vol. 25 (1), pp. 186-189.
Smotrys et al., "Palmitoylation of Intracellular Signaling Proteins: Regulation and Function," Annual Review of Biochemistry, 2004, vol. 73, pp. 559-587.
Solary et al., "Proteases, Proteolysis, and Apoptosis," Cell Biology and Toxicology, Mar. 1998, vol. 14(2), pp. 121-132.
Sperandio et al., "An Alternative, Nonapoptotic form of Programmed Cell Death," Proceedings of the National Academy of Sciences of the United States of America, Dec. 2000, vol. 97 (26), pp. 14376-14381.
Stevenson et al., "Myristyl Acylation of the Tumor Necrosis Factor alpha Precursor on Specific Lysine Residues," The Journal of Experimental Medicine, Oct. 1992, vol. 176 (4), pp. 1053-1062.
Stevenson et al., "The 31-Kda Precursor of Interleukin 1 Alpha is Myristoylated on Specific Lysines Within the 16-Kda 4-Terminal Propiece," Proceedings of the National Academy of Sciences of the United States of America, Aug. 1993, vol. 90 (15), pp. 7245-7249.
Sugii et al., "Performance Improvement in Protein N-Myristoyl Classification By BONSAI with Insignificant Indexing Symbol," Genome Informatics, 2007, vol. 18, pp. 277-286.
Suzuki et al., "Strategy for Comprehensive Identification of Human N-Myristoylated Proteins Using an Insect Cell-Free Protein Synthesis System," Proteomics, May 2010, vol. 10 (9), pp. 1780-1793.
Swerdlow, Who classification of tumours of haematopoietic and lymphoid tissues. Lyon: International Agency for Research on Cancer; GLOBOCAN 2012. Accessed Apr. 9, 2016 (5 pages) [online]. Retrieved from the Internet: URL: http://globocaniarch/old/FactSheets/cancers/all-new.asp.
Takada et al., "Monounsaturated Fatty Acid Modification of Wnt Protein: Its Role in Wnt Secretion," Development Cell, Dec. 2006, vol. 11 (6), pp. 791-801.
Takamune et al., "Suppression of Human Immunodeficiency Virus Type-1 Production by Coexpression of Catalytic-Region-Deleted N-Myristoyltransferase Mutants," Biological and Pharmaceutical Bulletin, 2010, vol. 33 (12), pp. 2018-2023.
Tate et al., "N-Myristoyltransferase as a Potential Drug Target in Malaria and Leishmaniasis," Parasitology, Jan. 2014, vol. 141 (1), pp. 37-49.
The Affordable Care Act. The Leukemia and Lymphoma Society, accessed on Oct. 30, 2013. The Affordable Care Act (2 pages) [online]. Retrieved from the Internet: URL: http://www.11s.org.search.

(56) References Cited

OTHER PUBLICATIONS

Thinon et al., "Global Profiling of Co- And Post-Translationally N-Myristoylated Proteomes in Human Cells," Nature Communications, Sep. 2014, vol. 5, 13 pages.
Tomatis et al., "Acyl-Protein Thioesterase 2 Catalizes the Deacylation of Peripheral Membrane-Associated GAP-43," PLoS One, Nov. 2010, vol. 5 (11), pp. e15045.
Toska et al., "Repression of Transcription by WT1-BASP1 Requires the Myristoylation of BASP1 and the PIP2- Dependent Recruitment of Histone Deacetylase," Cell Reports, Sep. 2012, vol. 2 (3), pp. 462-469.
Towler et al., "Amino-Terminal Processing of Proteins by N-myristoylation. Substrate Specificity of N-myristoyl transferase," The Journal of Biological Chemistry, Jan. 1987, vol. 262 (3), pp. 1030-1036.
Towler et al., "Protein Fatty Acid Acylation: Enzymatic Synthesis of an N-Myristoylglycyl Peptide," Proceedings of the National Academy of Sciences of the United States of America, May 1986, vol. 83 (9), pp. 2812-2816.
Towler et al., "Purification and Characterization of Yeast Myristoyl CoA:Protein N-Myristoyltransferase," Proceedings of the National Academy of Sciences of the United States of America, May 1987, vol. 84 (9), pp. 2708-2712.
Traverso et al., "High-Throughput Profiling of N-Myristoylation Substrate Specificity Across Species Including Pathogens," Proteomics, Jan. 2013, vol. 13 (1), pp. 25-36.
Tsai et al., "Chemical Biology of Glycosylphosphatidylinositol Anchors," Angewandte Chemie International Edition in English, Nov. 2012, vol. 51 (46), pp. 11438-11456.
Turnay et al., "Structure-function Relationship in Annexin A13, the Founder Member of the Vertebrate Family of Annexins," The Biochemical Journal, Aug. 2005, vol. 389 (Pt 3), pp. 899-911.
Uniprot, NMT2_HUMAN: Protein Glycylpeptide N-tetradecanoyltransferase 2; Gene NMT2. Accessed online at http://www.uniprot.org/uniprot/060551 on Mar. 10, 2017, 11 pages.
U.S. Appl. No. 16/025,835, Final Office Action dated Mar. 20, 2020.
U.S. Appl. No. 14/234,312, Final Office Action dated Aug. 24, 2016.
U.S. Appl. No. 14/234,312, Final Office Action dated Jan. 12, 2018.
U.S. Appl. No. 14/234,312, Non-Final Office Action dated Mar. 31, 2017.
U.S. Appl. No. 14/438,594, Final Office Action dated Oct. 2, 2017.
U.S. Appl. No. 14/438,594, Non-Final Office Action dated Mar. 22, 2017.
U.S. Appl. No. 15/943,068, Non-Final Office Action dated May 17, 2021.
U.S. Appl. No. 16/025,835, Non-Final Office Action dated May 31, 2019.
U.S. Appl. No. 16/025,835, Notice of Allowance dated Feb. 5, 2021.
U.S. Appl. No. 16/025,835, Notice of Allowance dated Jun. 9, 2021.
U.S. Appl. No. 15/943,068, Final Office Action dated Oct. 30, 2020.
U.S. Appl. No. 15/943,068, Non-Final Office Action dated Apr. 22, 2020.
Uno et al., "Myristoylation of the Fus1 Protein Is Required for Tumor Suppression in Human Lung Cancer Cells," Cancer Research, May 2004, vol. 64 (9), pp. 2969-2976.
Utsumi et al., "C-Terminal 15 kDa Fragment of Cytoskeletal Actin is Posttranslationally N-Myristoylated Upon Caspase- Mediated Cleavage and Targeted to Mitochondria," FEBS Letters, Mar. 2003, vol. 539 (1-3), pp. 37-44.
Utsumi et al., "Vertical-Scanning Mutagenesis of Amino Acids in a Model N-Myristoylation Motif Reveals the Major Amino-Terminal Sequence Requirements for Protein N-Myristoylation," European Journal of Biochemistry, Feb. 2004, vol. 271 (4), pp. 863-874.
Veer et al., "Enabling Personalized Cancer Medicine Through Analysis of Gene-Expression Patterns," Nature, Apr. 2008, vol. 452 (7187), pp. 564-570.
Vilas et al., "Posttranslational Myristoylation of Caspase'activated P21-Activated Protein Kinase 2 (PAK2) Potentiates Late Apoptotic Events," Proceedings of the National Academy of Sciences of the United States of America, Apr. 2006, vol. 103 (17), pp. 6542-6547.
Wahlstrom et al., "Reel Deficiency Accelerates the Development of K-RAS-induced Myeloproliferative Disease," Blood, Jan. 2007, vol. 109 (2), pp. 763-768.
Walsh et al., "Executioner Caspase-3 and Caspase-7 Are Functionally Distinct Proteases," Proceedings of the National Academy of Sciences of the United States of America, Sep. 2008, vol. 105 (35), pp. 12815-12819.
Wang et al., "Bioconjugation by Copper(I)-Catalyzed Azide-Alkyne [3 + 2] Cycloaddition," Journal of the American Chemical Society, Mar. 2003, vol. 125 (11), pp. 3192-3193.
Webb et al., "Inhibition of Protein Palmitoylation, Raft Localization, and T Cell Signaling by 2-bromopalmitate and Polyunsaturated Fatty Acids," The Journal of Biological Chemistry, Jan. 2000, vol. 275(1), pp. 261-270.
Weinberg et al., "Genetic Studies Reveal that MyristoylCoA:protein N-Myristoyltransferase is an Essential Enzyme in Candida Albicans," Molecular Microbiology, Apr. 1995, vol. 16 (2), pp. 241-250.
Weston et al., "Crystal Structure of the Anti-Fungal Target N-Myristoyl Transferase," Nature Structural Biology, Mar. 1998, vol. 5 (3), pp. 213-221.
Wikipedia, Definition: Small molecule. Accessed online at https://en.wikipedia.org/wiki/Small_molecule on Mar. 10, 2017, 4 pages.
Wilcox et al., "Acylation of Proteins With Myristic Acid Occurs Cotranslationally," Science, Nov. 1987, vol. 238 (4831), pp. 1275-1278.
Willert et al., "Wnt Proteins are Lipid-Modified and can Act as Stem Cell Growth Factors," Nature, May 2003, vol. 423 (6938), pp. 448-452.
Wright et al., "Protein Myristoylation in Health and Disease," Journal of Chemical Biology, Mar. 2010, vol. 3(1), pp. 19-35.
Written Opinion for Application No. PCT/CA2012/000696, dated Nov. 7, 2012, 7 pages.
Written Opinion for Application No. PCT/CA2013/050821, dated Feb. 5, 2014, 8 pages.
Wu et al., "Crystal Structures of *Saccharomyces cerevisiae* N-myristoyltransferase With Bound Myristoyl-CoA and Inhibitors Reveal the Functional Roles of the N-Terminal Region," The Journal of Biological Chemistry, Jul. 2007, vol. 282 (30), pp. 22185-22194.
Wu et al., "Necroptosis: An Emerging Form of Programmed Cell Death," Critical Reviews in Oncology/hematology, Jun. 2012, vol. 82 (3), pp. 249-258.
Yang et al., "Identification of the Acyltransferase that Octanoylates Ghrelin, an Appetite-Stimulating Peptide Hormone," Cell, Feb. 2008, vol. 132 (3), pp. 387-396.
Yang et al., "N-Myristoyltransferase 1 Is Essential in Early Mouse Development," The Journal of Biological Chemistry, May 2005, vol. 280 (19), pp. 18990-18995.
Yap et al., "Rapid and Selective Detection of Fatty Acylated Proteins Using Omega-Alkynyl-Fatty Acids and Click Chemistry," Clinical Cancer Research, Jun. 2010, vol. 51 (6), pp. 1566-1580.
Youle et al., "The BCL-2 Protein Family: Opposing Activities that Mediate Cell Death," Nature Reviews Molecular Cell Biology, Jan. 2008, vol. 9 (1), pp. 47-59.
Yustein et al., "Biology and Treatment of Burkitt's Lymphoma," Current Opinion in Hematology, Jul. 2007, vol. 14 (4), pp. 375-381.
Zha, "Posttranslational N-Myristoylation of BID as a Molecular Switch for Targeting Mitochondria and Apoptosis," Science, Dec. 2000, vol. 290 (5497), pp. 1761-1765.
Zhang et al., "Down-Regulation of NKD1 Increases the Invasive Potential of Non-Small-Cell Lung Cancer and Correlates with a Poor Prognosis," BMC Cancer, May 2011, vol. 11, pp. 186.
Zhang et al., "Protein Prenylation: Molecular Mechanisms and Functional Consequences," Annual Review of Biochemistry, 1996, vol. 65, pp. 241-269.
Zhao et al., "Palmitoylation of Apolipoprotein B Is Required for Proper Intracellular Sorting and Transport of Cholesteroyl Esters and Triglycerides," Molecular Biology of the Cell, Feb. 2000, vol. 11 (2), pp. 721-734.
Zverina et al., "Recent Advances in Protein Prenyltransferases: Substrate Identification, Regulation, and Disease -Interventions," Current Opinion in Chemical Biology, Dec. 2012, vol. 16(5-6), pp. 544-552.

(56) References Cited

OTHER PUBLICATIONS

French et al., "Cyclohexyl-Octahydro-Pyrrolo[1,2-a]Pyrazine-Based Inhibitors of Human N-Myristoyltransferase-1," Journal of Pharmacology and Experimental Therapeutics, Apr. 2004, vol. 309(1), pp. 340-347.
Fukata et al., "Protein Palmitoylation in Neuronal Development and Synaptic Plasticity," Nature Reviews Neuroscience, Mar. 2010, vol. 11 (3), pp. 161-175.
Greaves et al., "DHHC Palmitoyl Transferases: Substrate Interactions and (Patho) Physiology," Trends in Biochemical Sciences, May 2011, vol. 36 (5), pp. 245-253.
Hang et al., "Chemical probes for the rapid detection of Fatty-acylated proteins in Mammalian cells.," Journal of the American Chemical Society, Mar. 2007, vol. 129 (10), pp. 2744-2745.
Hannoush et al., "Imaging the Lipidome: omega-Alkynyl Fatty Acids for Detection and Cellular Visualization of Lipid-Modified Proteins," ACS Chemical Biology, Jul. 2009, vol. 4 (7), pp. 581-587.
Hannoush et al., "The Chemical Toolbox for Monitoring Protein Fatty Acylation and Prenylation," Nature Chemical Biology, Jul. 2010, vol. 6 (7), pp. 498-506.
Heal et al., "Bioorthogonal Chemical Tagging of Protein Cholesterylation in Living Cells," Chemical Communications, Apr. 2011, vol. 47 (14), pp. 4081-4083.
Hirsch et al., "Easily Reversible Desthiobiotin Binding to Streptavidin, Avidin, and Other Biotin-binding Proteins: Uses for Protein Labeling, Detection, and Isolation," Analytical Biochemistry, Sep. 2002, vol. 308 (2), pp. 343-357.
Hudson et al., "Sect 2.4: Viable Lymphocyte Count," found in Practical Immunology, Blackwell Scientific Publications, Oxford, England, 1976, 29-32.
International Patent Application No. PCT/CA2012/000696, International Preliminary Reporton Patentability dated Feb. 6, 2014.
International Patent Application No. PCT/CA2013/050821, International Preliminary Reporton Patentability dated May 14, 2015.
Japanese Patent Application No. 2014-520475, Office Action dated Apr. 10, 2017.
Office Action for Canadian Patent Application No. 2,890,113, dated Aug. 19, 2021 (3 pages).
Corrected Notice of Allowability for U.S. Appl. No. 16/025,835, dated Aug. 27, 2021 (2 pages).
Office Action for Brazilian Patent Application No. 112015009607-7, dated Nov. 8, 2021 (4 pages).
Office Action for Chinese Patent Application No. 201910130300.4, dated Nov. 10, 2021 (6 pages).
Gebhart et al., "Genomic Imbalances in T-cell Acute Lymphoblastic Leukemia Cell Lines," International Journal of Oncology. 21(4): 887-894 (2002).
Office Action for Korean Patent Application No. 10-2015-7014547, dated Dec. 20, 2021 (7 pages).
Kosciuk et al., "NMT as a Glycine and Lysine Myristoyltransferase in Cancer, Immunity, and Infections," available in PMC Jul. 17, 2021, published in final edited form as: ACS Chem Biol. 15(7): 1747-1758 (2020).
Final Office Action for U.S. Appl. No. 15/943,068, dated Dec. 20, 2021 (24 pages).
Beaver et al., "Response Rate After Administration of a Single Dose of Doxorubicin in Dogs With B-cell or T-cell Lymphoma: 41 Cases (2006-2008)" Journal of the American Veterinary Medical Association, vol. 237 (9), pp. 1052-1055 (Nov. 1, 2010).
Office Action for Brazilian Patent Application No. BR112015009607-7, dated May 19, 2022 (4 pages) (English language summary).
Office Action for Brazilian Patent Application No. BR112014001430-2, dated May 13, 2022 (6 pages) (English language summary).
Office Action for Brazilian Patent Application No. BR112014001430-2, dated Sep. 12, 2022 (5 pages) (English language summary).
Office Action for Chinese Patent Application No. 201910130300.4, dated May 7, 2022 (7 pages).
Office Action for Chinese Patent Application No. 201910841567.4, dated May 23, 2022 (16 pages).
Office Action for European Patent Application No. 12817041.2, dated Jun. 2, 2022 (5 pages).
Office Action for Japanese Patent Application No. 2021-176651, dated Nov. 7, 2022 (8 pages).
Office Action for Korean Patent Application No. 10-2015-7014547, dated Apr. 19, 2022 (15 pages).
Office Action for Korean Patent Application No. 10-2022-7009175, dated Jul. 7, 2022 (16 pages).
Examination Report for New Zealand Patent Application No. 737605, dated Jul. 28, 2022 (4 pages).
Notice of Acceptance for New Zealand Patent Application No. 737605, dated Nov. 15, 2022 (2 pages).
Office Action for Brazilian Patent Application No. BR112015009607-7, dated Nov. 28, 2022 (6 pages) (English language summary).
Office Action for Chinese Patent Application No. 201910841567.4, dated Dec. 21, 2022 (5 pages).
Notice of Grant for Korean Patent Application No. 10-2015-7014547, dated Jan. 20, 2023 (8 pages).
Examination Report for New Zealand Patent Application No. 794388, dated Nov. 15, 2022 (1 page).
Search Report and Written Opinion for Singapore Patent Application No. SG10201703505V, dated Jan. 6, 2023 (5 pages).
Notice of Eligibility of Grant for Singapore Patent Application No. SG10201610058140, dated Dec. 1, 2022 (4 pages).
Notice of Intention to Grant for European Application No. 16826961.1, dated Mar. 13, 2023 (69 pages).
Office Action for Japanese Patent Application No. 2018-502095, dated Apr. 24, 2023 (13 pages).
Decision to Grant for European Patent Application No. 16826961.1, dated Aug. 3, 2023 (2 pages).
Decision to Reject the Amendments for Japanese Patent Application No. 2021-176651, dated Jul. 24, 2023 (with English Translation, 8 pages).
Office Action for Japanese Patent Application No. 2021-176651, dated Jul. 24, 2023 (with English Translation, 4 pages).

\* cited by examiner (Black curve above grey curve at intersection of axis.)

(Black curve is top curve; grey curve is bottom curve.)

"Low NMT2 Expressiors" curve is bottom curve; "High NMT2 Expressiors" is top curve.

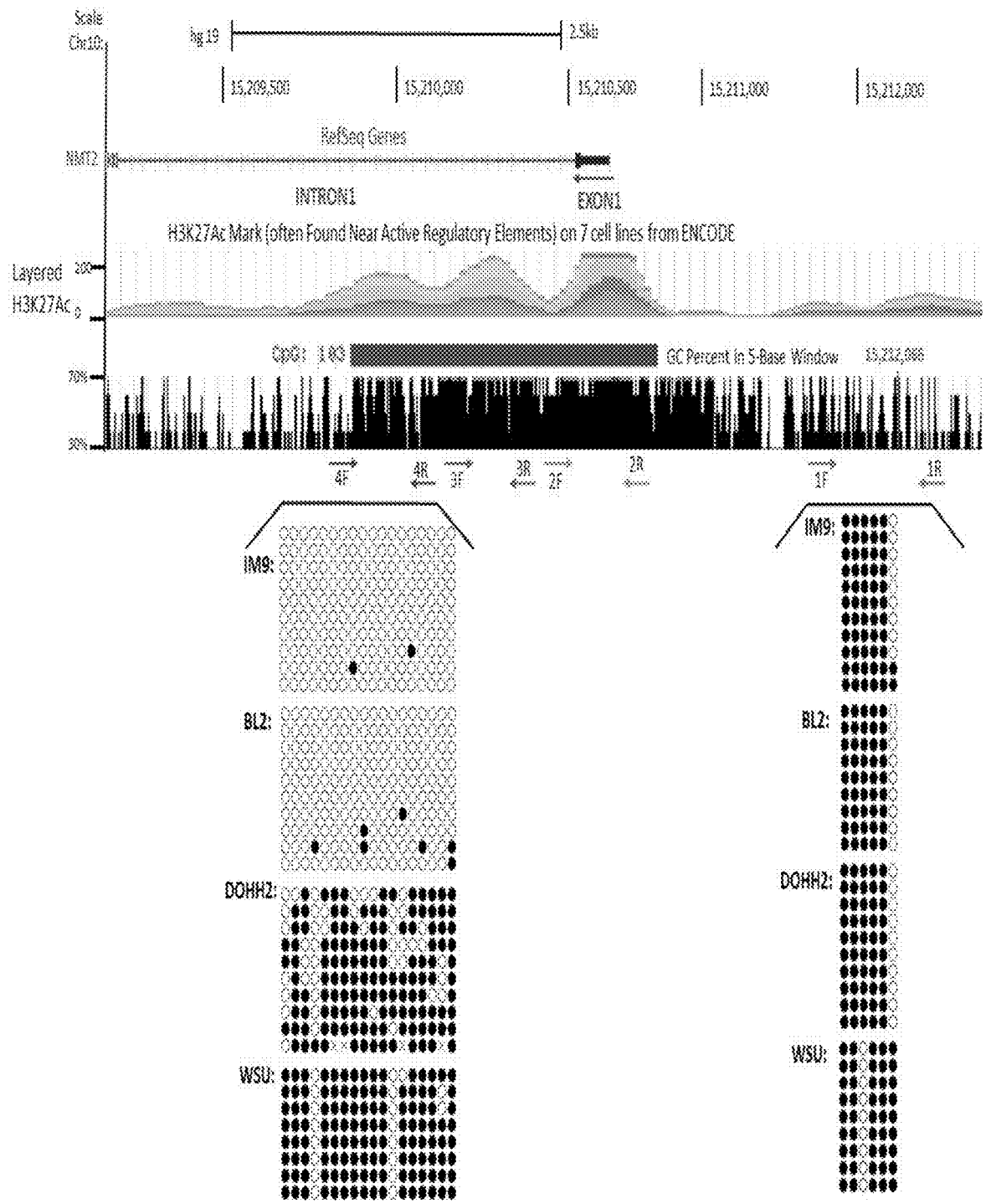
Figure 2 B -- Epigenetic regulation of NMT2 in lymphoma cell lines and tumours.

Bisulfite sequencing of *DAPK1* promoter region reveals a highly methylated CpG containing promoter region only in malignant B lymphocytes Statistical Significance for Kruskal-Wallis Dunn's test: ne = not evaluable; ns = not significant, * = P < 0.05,  = P < 0.01, * = P < 0.001, compared to Group 1
TGI ≥ 60% indicates potential therapeutic activity

EPIGENETIC SILENCING OF NMT2

CROSS REFERENCE TO RELATED APPLICATION

This application claims priority to U.S. provisional patent application No. U.S. 62/194,109, filed Jul. 17, 2015, the entire contents of which are hereby incorporated by reference.

FIELD

The present disclosure relates generally to epigenetic methods for cancer diagnosis and treatment.

BACKGROUND

Cancer is a leading cause of death in Canada. The Canadian Cancer Society estimate there will be approximately 170000 new cases of cancer in 2011, and approximately 75000 deaths as a result of cancer.

It has been estimated that in 2015, about 589430 Americans will die of cancer, or about 1,620 people per day. Cancer is the second most common cause of death in the US, and accounts for nearly 1 of every 4 deaths.

Hematological cancers account for approximately nine percent of new cancer cases and nine percent of cancer related deaths. One type of hematological cancer is lymphoma. Aggressive non Hodgkin Lymphomas such as Burkitt Lymphoma (BL) and Diffuse Large B Cell Lymphoma (DLBCL) are treatable, but current therapies are expensive, carry serious toxicities, and achieve widely varying responses, with the majority of patients ultimately experiencing disease relapse. In North America alone, there are 78,000 new NHL cases per year and 600,000 NHL survivors in remission but with ongoing risk of relapse. Improved treatments are required.

N-myristoylation of proteins is a modification in which myristate (a 14-carbon saturated fatty acid) is covalently attached to the NH2 terminal glycine of a variety of cellular, viral, and onco-proteins (e.g., oncogenic Src-related tyrosine kinases, heterotrimeric G alpha subunits, etc.).

Cellular myristoylated proteins have diverse biological functions in signal transduction and oncogenesis. Modification of proteins by myristoylation is required for the sub-cellular targeting, protein conformation and biological activity of many important proteins in eukaryotic cells, including those required for signal transduction and regulatory functions important in cell growth. Tyrosine kinases of the Src family (proto-oncogenes) are among the most extensively studied myristoylated proteins.

Myristoylation of proteins is catalyzed by N-myristoyltransferase (NMT). NMT is responsible for this activity in eukaryotic cells and works by modifying its polypeptide substrate after the removal of the initiator methionine residue by methionyl aminopeptidase. This modification occurs primarily as a cotranslational process, although myristoylation can also occur post-translationally after proteolytic cleavage of proteins, typically during apoptosis. Two isozymes of the mammalian NMT enzymes have been cloned and are designated NMT1 and NMT2. NMTs play a pro-survival role in cells. The two NMTs are present in all normal mammalian cells.

There remains a need for compounds, composition and method for the treatment of cancer.

This background information is provided for the purpose of making known information believed by the applicant to be of possible relevance to the present invention. No admission is necessarily intended, nor should it be construed, that any of the preceding information constitutes prior art against the present invention.

SUMMARY

In one aspect of the present disclosure there is provided a method of predicting the response in a cancer patient to treatment with an NMT inhibitor comprising, providing a biological sample of said cancer patient, and determining in said biological sample the methylation status of the NMT2 gene, and predicting a positive clinical response to said treatment with said NMT inhibitor, if hypermethylation is determined in the NMT2 gene.

In one aspect of the present disclosure there is provided a method for identifying and/or selecting a patient with a cancer, or treated for a cancer, suitable for treatment with an NMT inhibitor, comprising providing a biological sample of said cancer patient, and determining the methylation status of the NMT2 gene, and identifying and/or selecting the cancer patient for treatment with said NMT inhibitor if hypermethylation is determined in the NMT2 gene.

In one aspect of the present disclosure there is provided a method for selecting a suitable treatment regimen for a cancer in a cancer patient comprising providing a biological sample of said cancer patient, and determining in said biological sample the methylation status of the NMT2 gene, and selecting an NMT inhibitor for treatment if hypermethylation of NMT2 gene is determined and/or under expression is determined in the NMT2 gene.

In one aspect of the present disclosure there is provided a method of treating a patient with cancer with an NMT inhibitor comprising providing a biological sample of said cancer patient, and determining in said biological sample the methylation status of NMT2 gene, and selecting said NMT inhibitor for treatment if hypermethylation is determined in NMT2 gene.

In one aspect of the present disclosure there is provided a method comprising: a) obtaining a sample from a subject having cancer, or suspected as having cancer; b) contacting the sample with a reagent to form a product (in some cases a complex) indicative of methylation status of NMT2 gene present in the sample; c) measuring the product formed to determine a methylation status of NMT2 gene in the sample; and d) determining the benefit of NMT inhibitor treatment of said cancer in in said subject, wherein the determination of benefit of NMT inhibitor treatment is determined by hypermethylation of NMT2 gene in said sample.

In one aspect, wherein in step b) said regent comprises primers to detect hypermethylation in the NMT2 gene.

In one aspect said primers comprise SEQ ID NO:1 and/or SEQ ID NO: 2.

In one aspect of the present disclosure there is provided a method of treating a subject with cancer or suspect of having cancer, comprising administering an NMT inhibitor to said subject when the NMT2 gene is hypermethylated in said sample, optionally as compared to a control.

In one aspect of the present disclosure there is provided a method for treating cancer in a subject, comprising: a) obtaining nucleic acid from a sample from the subject; b) performing bisulfite modification to the nucleic acid in step a); c) performing a method selected from PCR, methylation-specific PCR, quantitative methylation specific PCR (QMSP), realtime methylation-specific PCR, PCR assay using a methylation DNA-specific binding protein, quantitative PCR, DNA chip-based assay, pyrosequencing, or bisulfite sequencing, on the bisulfite modified nucleic acid from step b) using PCR primers and/or probes specific for the promoter region of the NMT2 gene, e) determining a promoter methylation level of the promoter region of NMT2 in the sample, optionally compared to a control, g) treating said patient with an inhibitor to NMT when promoter methylation level of the promoter region of NMT2 gene in the sample is determined to be hypermethylated.

In one aspect said PCR primers comprise SEQ ID NO:1 and/or SEQ ID NO: 2.

In one aspect determining the methylation status comprises, a) performing bisulfite modification to the nucleic acid in said sample, b) determining methylation of the promoter of the NMT2 gene using PCR primers and/or probes specific for the promoter region of the NMT2 gene from step a).

In one aspect step b) is performed by a method selected from PCR, methylation-specific PCR, quantitative methylation specific PCR (QMSP), realtime methylation-specific PCR, PCR assay using a methylation DNA-specific binding protein, quantitative PCR, DNA chip-based assay, pyrosequencing, or bisulfite sequencing, the bisulfite modified nucleic acid from step a).

In one aspect detection of hypermethylation of the NMT2 gene is performed with primers comprising SEQ ID NO: 1 and/or SEQ ID NO: 2.

In one aspect said NMT inhibitor comprises a small molecule, an antibody, a peptide fragment, a nucleic acid, or combinations thereof.

In one aspect said small molecule comprises DDD85646, DDD86481, or a derivative thereof.

In one aspect said antibody is a monoclonal antibody or a polyclonal antibody.

In one aspect said nucleic acid comprises a dsRNA molecule, a RNAi molecule, a miRNA molecule, a ribozyme, a shRNA molecule, or a siRNA molecule.

In one aspect said cancer is lymphoma, B cell lymphoma, follicular lymphoma, diffuse large B-cell lymphoma, mantle cell lymphoma, B-CLL/SLL, immunocytoma/Waldenstrom's, MALT-type/monocytoid B 20 cell lymphoma, Burkitt's lymphoma, a pediatric lymphoma, anaplastic large cell lymphoma, acute myeloid leukemia, Blast Phase Chronic Myeloid Leukaemia, Burkitt's Lymphoma, Plasma Cell Myeloma, Intestinal Adenocarcinoma, Lung mixed Adenosquamous Carcinoma, Lung Small Cell Carcinoma, Lung, Oesophagus Squamous Cell Carcinoma, Bone, Breast Ductal Carcinoma, Stomach Diffuse Adenocarcinoma, Thyroid Medullary Carcinoma, urinary Tract Transitional Cell Carcinoma, myeloma, ovarian clear cell carcinoma, transition cell carcinoma (ureter and bladder cancer), chronic myelogenous leukemia (CML), lymphoma-CLL, breast carcinoma, colorectal adenocarcinoma, pancreas adenocarcinoma, ovarian carcinoma, non-small cell lung carcinoma, osteosarcoma, melanoma, gastric adenocarcinoma, endometrial adenocarcinoma, esophageal squamous carcinoma.

In one aspect said NMT inhibitor comprises DDD85646 or DDD86481.

In one aspect said treatment further comprises treatment with a histone acetyl transferase inhibitor, a DNA demethylase Inhibitor, and/or histone demethylase inhibitor.

In one aspect said histone acetyl transferase inhibitor is anacardic acid, CPTH2, MB-3, and/or Curcumin.

In one aspect said histone demethylase inhibitor is Daminozide, GSK J1, GSK J2, GSK J4, GSK J5, GSK LSD 1 dihydrochloride, IOX 1, JIB 04, RN 1 dihydrochloride, TC-E 5002, and/or Tranylcypromine hydrochloride.

In one aspect, when said cancer is a lymphoma, the method further comprising administering a treatment selected from CHOP (i.e., cyclophosphamide, doxorubicin, vincristine, and prednisone), GAP-BOP (i.e., cyclophosphamide, doxorubicin, procarbazine, bleomycin, vincristine, and prednisone), m-BACOD (i.e., methotrexate, bleomycin, doxorubicin, cyclophosphamide, vincristine, dexamethasone, and leucovorin), ProMACE-MOPP (i.e., prednisone, methotrexate, doxorubicin, cyclophosphamide, etoposide, leucovorin with standard MOPP), ProMACE-CytaBOM (prednisone, doxorubicin, cyclophosphamide, etoposide, cytarabine, bleomycin, vincristine, methotrexate, and leucovorin), and MACOP-B (methotrexate, doxorubicin, cyclophosphamide, vincristine, prednisone, bleomycin, and leucovorin). For relapsed aggressive non-Hodgkin's lymphoma the following chemotherapy drug combinations may be used with the compounds and compositions described herein: IMVP-16 (i.e., ifosfamide, methotrexate, and etoposide), MIME (i.e., methyl-gag, ifosfamide, methotrexate, and etoposide), DHAP (i.e., dexamethasone,—16 high dose cytarabine, and cisplatin), ESHAP (i.e., etoposide, methylprednisone, high dosage cytarabine, and cisplatin), CEFF(B) (i.e., cyclophosphamide, etoposide, procarbazine, prednisone, and bleomycin), or CAMP (i.e., lomustine, mitoxantrone, cytarabine, and prednisone).

In one aspect, when said cancer is Hodgkin's disease, the method further comprising administering a treatment selected from VABCD (i.e., vinbiastine, doxorubicin, dacarbazine, lomustine and bleomycin), ABDIC (i.e., doxorubicin, bleomycin, dacarbazine, lomustine, and prednisone), CBVD (i.e., lomustine, bleomycin, vinblastine, dexamethasone), PCVP (i.e., vinbiastine, procarbazine, cyclophosphamide, and prednisone), CEP (i.e., lomustine, etoposide, and prednimustine), EVA (i.e., etoposide, vinbiastine, and doxorubicin), MOPLACE (i.e., cyclophosphamide, etoposide, prednisone, methotrexate, cytaravine, and vincristine), MIME (i.e., methyl-gag, ifosfamide, methotrexate, and etoposide), MINE (i.e., mitoquazone, ifosfamide, vinorelbine, and etoposide), MTX-CHOP (i.e., methotrexate and CHOP), CEM (i.e., lomustine, etoposide, and methotrexate), CEVD (i.e., lomustine, etoposide, vindesine, and dexamethasone), CAVP (i.e., lomustine, melphalan, etoposide, and prednisone), EVAP (i.e., etoposide, vinblastine, cytarabine, and cisplatin), and EPOCH (i.e., etoposide, vincristine, doxorubicin, cyclophosphamide, and prednisone).

In one aspect, when said cancer is breast cancer, the method further comprising administering a treatment selected from paclitaxel, docetaxel, nanoparticle albumin bound paclitaxel, capecitabine, doxorubicin, eribulin, vinorelbine, trastuzumab, carboplatin, cisplatin; endocrine therapies including tamoxifen, anastrozole, letrozole, exemestane, fulvestrant, and cell cycle inhibitors including palbocilib, ribociclib, LEE001, and everolimus; immune checkpoint inhibiting drugs including nivolumab and pembrolizumab, either individually or in combination.

In one aspect, when said cancer is small cell lung cancer, the method further comprising administering a treatment selected from carboplatin, cisplatin, etoposide, irinotecan, either individually or in combination.

In one aspect, when said cancer is non-small cell lung cancer, the method further comprising administering a treatment selected from carboplatin, paclitaxel, docetaxel, gefitinib, erlotinib, afatinib, bevacizumab, ramucirumab, osimertinib, necitumumab, crizotinib, ceritinib, alectinib, and immune checkpoint inhibiting drugs including nivolumab, pembrolizumab, either individually or in combination.

In one aspect, when said cancer is bladder carcinoma, the method further comprising administering a treatment selected from methotrexate, vincblastine, doxorubicin, cisplatin; carboplatin and paclitaxel; docetaxel, gemcitabine and cisplatin, either individually or in combination.

In one aspect the determination of hypermethylation in the NMT2 gene is performed by a method selected from the group consisting of PCR, methylation-specific PCR, realtime methylation-specific PCR, PCR assay using a methylation DNA-specific binding protein, quantitative PCR, DNA chip-based assay, pyrosequencing, and bisulfite sequencing.

In one aspect said biological sample comprises, a tissue, a cell specimen or fluids includes detached tumor cells and/or free nucleic acids, a blood sample, a fractionated blood sample, a bone marrow sample, a biopsy sample, a frozen tissue sample, a fresh tissue specimen, a cell sample, and/or a paraffin embedded section.

In one aspect said subject is a human.

In one aspect of the present disclosure there is described an in vitro assay for selecting a treatment for a patient with cancer, comprising: a) obtaining nucleic acid from a sample from the subject; b) performing bisulfite modification to the nucleic acid in step a); c) performing a method selected from PCR, methylation-specific PCR, quantitative methylation specific PCR (QMSP), realtime methylation-specific PCR, PCR assay using a methylation DNA-specific binding protein, quantitative PCR, DNA chip-based assay, pyrosequencing, or bisulfite sequencing, on the bisulfite modified nucleic acid from step b) using PCR primers and/or probes specific for the promoter region of the NMT2 gene, e) determining a promoter methylation level of the promoter region of NMT2 in the sample, optionally compared to a control, wherein the selected treatment is an NMT inhibitor when promoter region of NMT2 gene in the sample is determined to be hypermethylated.

In one aspect said PCR primers comprise SEQ ID NO:1 and/or SEQ ID NO: 2.

In one aspect of the present disclosure there is described an in vitro assay of a sample from a patient for selecting a treatment for a patient with cancer, comprising: a) performing bisulfite modification to the nucleic acid in said sample, b) determining methylation of the promoter of the NMT2 gene using PCR primers and/or probes specific for the promoter region of the NMT2 gene from step a).

In one aspect step b) is performed by a method selected from PCR, methylation-specific PCR, quantitative methylation specific PCR (QMSP), realtime methylation-specific PCR, PCR assay using a methylation DNA-specific binding protein, quantitative PCR, DNA chip-based assay, pyrosequencing, or bisulfite sequencing, the bisulfite modified nucleic acid from step a).

In one aspect detection of hypermethylation of the NMT2 gene is performed with primers comprising SEQ ID NO: 1 and/or SEQ ID NO: 2.

In one aspect the selected treatment is an NMT inhibitor when promoter region of NMT2 gene in the sample is determined to be hypermethylated.

In one aspect said NMT inhibitor comprises a small molecule, an antibody, a peptide fragment, a nucleic acid, or combinations thereof.

In one aspect said small molecule comprises DDD85646, DDD86481, or a derivative thereof.

In one aspect said antibody is a monoclonal antibody or a polyclonal antibody.

In one aspect said nucleic acid comprises a dsRNA molecule, a RNAi molecule, a miRNA molecule, a ribozyme, a shRNA molecule, or a siRNA molecule.

In one aspect of the present disclosure there is described a kit for selecting a suitable treatment for a cancer in a cancer patient, comprising: a) one or more reagents for determining the methylation status of the NMT2 gene from a sample of said cancer patient, wherein the selected treatment is an NMT inhibitor when promoter region of NMT2 gene in the sample is determined to be hypermethylated, b) instructions for the use thereof.

In one aspect said reagents comprise PCR primers and/or probes specific for the promoter region of the NMT2 gene.

In one aspect said PCR primers comprise SEQ ID NO:1 and/or SEQ ID NO: 2.

In one aspect, further comprising and NMT inhibitor.

In one aspect said NMT inhibitor comprises a small molecule, an antibody, a peptide fragment, a nucleic acid, or combinations thereof.

In one aspect said small molecule comprises DDD85646, DDD86481, or a derivative thereof.

In one aspect said antibody is a monoclonal antibody or a polyclonal antibody.

In one aspect said nucleic acid comprises a dsRNA molecule, a RNAi molecule, a miRNA molecule, a ribozyme, a shRNA molecule, or a siRNA molecule.

In one aspect further comprising a histone acetyl transferase inhibitor, a DNA demethylase Inhibitor, and/or histone demethylase inhibitor.

In one aspect said histone acetyl transferase inhibitor is anacardic acid, CPTH2, MB-3, and/or Curcumin.

In one aspect said histone demethylase inhibitor is Daminozide, GSK J1, GSK J2, GSK J4, GSK J5, GSK LSD 1 dihydrochloride, IOX 1, JIB 04, RN 1 dihydrochloride, TC-E 5002, and/or Tranylcypromine hydrochloride.

In one aspect further comprising reagents for a treatment selected from CHOP (i.e., cyclophosphamide, doxorubicin, vincristine, and prednisone), GAP-BOP (i.e., cyclophosphamide, doxorubicin, procarbazine, bleomycin, vincristine, and prednisone), m-BACOD (i.e., methotrexate, bleomycin, doxorubicin, cyclophosphamide, vincristine, dexamethasone, and leucovorin), ProMACE-MOPP (i.e., prednisone, methotrexate, doxorubicin, cyclophosphamide, etoposide, leucovorin with standard MOPP), ProMACE-CytaBOM (prednisone, doxorubicin, cyclophosphamide, etoposide, cytarabine, bleomycin, vincristine, methotrexate, and leucovorin), and MACOP-B (methotrexate, doxorubicin, cyclophosphamide, vincristine, prednisone, bleomycin, and leucovorin). For relapsed aggressive non-Hodgkin's lymphoma the following chemotherapy drug combinations may be used with the compounds and compositions described herein: IMVP-16 (i.e., ifosfamide, methotrexate, and etoposide), MIME (i.e., methyl-gag, ifosfamide, methotrexate, and etoposide), DHAP (i.e., dexamethasone,—16 high dose cytarabine, and cisplatin), ESHAP (i.e., etoposide, methylprednisone, high dosage cytarabine, and cisplatin), CEFF(B) (i.e., cyclophosphamide, etoposide, procarbazine, prednisone, and bleomycin), or CAMP (i.e., lomustine, mitoxantrone, cytarabine, and prednisone).

In one aspect further comprising reagents for a treatment for Hodgkin's disease selected from VABCD (i.e., vinbiastine, doxorubicin, dacarbazine, lomustine and bleomycin), ABDIC (i.e., doxorubicin, bleomycin, dacarbazine, lomustine, and prednisone), CBVD (i.e., lomustine, bleomycin, vinbiastine, dexamethasone), PCVP (i.e., vinblastine, procarbazine, cyclophosphamide, and prednisone), CEP (i.e., lomustine, etoposide, and prednimustine), EVA (i.e., etoposide, vinbiastine, and doxorubicin), MOPLACE (i.e., cyclophosphamide, etoposide, prednisone, methotrexate, cytaravine, and vincristine), MIME (i.e., methyl-gag, ifosfamide, methotrexate, and etoposide), MINE (i.e., mitoquazone, ifosfamide, vinorelbine, and etoposide), MTX-CHOP (i.e., methotrexate and CHOP), CEM (i.e., lomustine, etoposide, and methotrexate), CEVD (i.e., lomustine, etoposide, vindesine, and dexamethasone), CAVP (i.e., lomustine, melphalan, etoposide, and prednisone), EVAP (i.e., etoposide, vinbiastine, cytarabine, and cisplatin), and EPOCH (i.e., etoposide, vincristine, doxorubicin, cyclophosphamide, and prednisone).

In one aspect further comprising reagents for a treatment for breast cancer selected from paclitaxel, docetaxel, nanoparticle albumin bound pacditaxel, capecitabine, doxorubicin, eribulin, vinorelbine, trastuzumab, carboplatin, cisplatin; endocrine therapies including tamoxifen, anastrozole, letrozole, exemestane, fulvestrant, and cell cycle inhibitors including palbociclib, ribociclib, LEE001, and everolimus; immune checkpoint inhibiting drugs including nivolumab and pembrolizumab, either individually or in combination.

In one aspect further comprising reagents for a treatment for small cell lung cancer selected from carboplatin, cisplatin, etoposide, irinotecan, either individually or in combination.

In one aspect further comprising reagents for a treatment for non-small cell lung cancer selected from carboplatin, paclitaxel, docetaxel, gefitinib, erlotinib, afatinib, bevacizumab, ramucirumab, osimertinib, necitumumab, crizotinib, ceritinib, alectinib, and immune checkpoint inhibiting drugs including nivolumab, pembrolizumab, either individually or in combination.

In one aspect further comprising reagents for a treatment for bladder carcinoma, the method further comprising administering a treatment selected from methotrexate, vincblastine, doxorubicin, cisplatin; carboplatin and paclitaxel; docetaxel, gemcitabine and cisplatin, either individually or in combination.

In one aspect of the present disclosure there is described use of an NMT inhibitor for treating a subject with a cancer wherein the NMT2 gene in a sample from said subject is determined to be hypermethylated.

In one aspect of the present disclosure there is described use of an NMT inhibitor for the manufacture of a medicament for treating a subject with a cancer wherein the NMT2 gene in a sample from said subject is determined to be hypermethylated.

In one aspect determining the methylation status comprises, a) performing bisulfite modification to the nucleic acid in said sample, b) determining methylation of the promoter of the NMT2 gene using PCR primers and/or probes specific for the promoter region of the NMT2 gene from step a).

In one aspect step b) is performed by a method selected from PCR, methylation-specific PCR, quantitative methylation specific PCR (QMSP), realtime methylation-specific PCR, PCR assay using a methylation DNA-specific binding protein, quantitative PCR, DNA chip-based assay, pyrosequencing, or bisulfite sequencing, the bisulfite modified nucleic acid from step a).

In one aspect detection of hypermethylation of the NMT2 gene is performed with primers comprising SEQ ID NO: 1 and/or SEQ ID NO: 2.

In one aspect said NMT inhibitor comprises a small molecule, an antibody, a peptide fragment, a nucleic acid, or combinations thereof.

In one aspect said small molecule comprises DDD85646, DDD86481, or a derivative thereof.

In one aspect said antibody is a monoclonal antibody or a polyclonal antibody.

In one aspect said nucleic acid comprises a dsRNA molecule, a RNAi molecule, a miRNA molecule, a ribozyme, a shRNA molecule, or a siRNA molecule.

In one aspect said cancer is lymphoma, B cell lymphoma, follicular lymphoma, diffuse large B-cell lymphoma, mantle cell lymphoma, B-CLL/SLL, immunocytoma/Waldenstrom's, MALT-type/monocytoid B 20 cell lymphoma, Burkitt's lymphoma, a pediatric lymphoma, anaplastic large cell lymphoma, acute myeloid leukemia, Blast Phase Chronic Myeloid Leukaemia, Burkitt's Lymphoma, Plasma Cell Myeloma, Intestinal Adenocarcinoma, Lung mixed Adenosquamous Carcinoma, Lung Small Cell Carcinoma, Lung, Oesophagus Squamous Cell Carcinoma, Bone, Breast Ductal Carcinoma, Stomach Diffuse Adenocarcinoma, Thyroid Medullary Carcinoma, urinary Tract Transitional Cell Carcinoma, myeloma, ovarian clear cell carcinoma, transition cell carcinoma (ureter and bladder cancer), chronic myelogenous leukemia (CML), lymphoma-CLL, breast carcinoma, colorectal adenocarcinoma, pancreas adenocarcinoma, ovarian carcinoma, non-small cell lung carcinoma, osteosarcoma, melanoma, gastric adenocarcinoma, endometrial adenocarcinoma, esophageal squamous carcinoma.

In one aspect said NMT inhibitor comprises DDD85646 or DDD86481.

In one aspect further comprising use of a histone acetyl transferase inhibitor, a DNA demethylase Inhibitor, and/or histone demethylase inhibitor.

In one aspect said histone acetyl transferase inhibitor is anacardic acid, CPTH2, MB-3, and/or Curcumin.

In one aspect said histone demethylase inhibitor is Daminozide, GSK J1, GSK J2, GSK J4, GSK J5, GSK LSD 1 dihydrochloride, IOX 1, JIB 04, RN 1 dihydrochloride, TC-E 5002, and/or Tranylcypromine hydrochloride.

In one aspect, wherein when said cancer is a lymphoma, the use further comprising use of a treatment selected from CHOP (i.e., cydophosphamide, doxorubicin, vincristine, and prednisone), GAP-BOP (i.e., cyclophosphamide, doxorubicin, procarbazine, bleomycin, vincristine, and prednisone), m-BACOD (i.e., methotrexate, bleomycin, doxorubicin, cydophosphamide, vincristine, dexamethasone, and leucovorin), ProMACE-MOPP (i.e., prednisone, methotrexate, doxorubicin, cyclophosphamide, etoposide, leucovorin with standard MOPP), ProMACE-CytaBOM (prednisone, doxorubicin, cyclophosphamide, etoposide, cytarabine, bleomycin, vincristine, methotrexate, and leucovorin), and MACOP-B (methotrexate, doxorubicin, cyclophosphamide, vincristine, prednisone, bleomycin, and leucovorin). For relapsed aggressive non-Hodgkin's lymphoma the following chemotherapy drug combinations may be used with the compounds and compositions described herein: IMVP-16 (i.e., ifosfamide, methotrexate, and etoposide), MIME (i.e., methyl-gag, ifosfamide, methotrexate, and etoposide), DHAP (i.e., dexamethasone,—16 high dose cytarabine, and cisplatin), ESHAP (i.e., etoposide, methylprednisone, high dosage cytarabine, and cisplatin), CEFF(B) (i.e., cydophosphamide, etoposide, procarbazine, prednisone, and bleomycin), or CAMP (i.e., lomustine, mitoxantrone, cytarabine, and prednisone).

In one aspect, wherein when said cancer is Hodgkin's disease, the use further comprising use of a treatment selected from VABCD (i.e., vinbiastine, doxorubicin, dacarbazine, lomustine and bleomycin), ABDIC (i.e., doxorubicin, bleomycin, dacarbazine, lomustine, and prednisone), CBVD (i.e., lomustine, bleomycin, vinbiastine, dexamethasone), PCVP (i.e., vinbiastine, procarbazine, cyclophosphamide, and prednisone), CEP (i.e., lomustine, etoposide, and prednimustine), EVA (i.e., etoposide, vinblastine, and doxorubicin), MOPLACE (i.e., cyclophosphamide, etoposide, prednisone, methotrexate, cytaravine, and vincristine), MIME (i.e., methyl-gag, ifosfamide, methotrexate, and etoposide), MINE (i.e., mitoquazone, ifosfamide, vinorelbine, and etoposide), MTX-CHOP (i.e., methotrexate and CHOP), CEM (i.e., lomustine, etoposide, and methotrexate), CEVD (i.e., lomustine, etoposide, vindesine, and dexamethasone), CAVP (i.e., lomustine, melphalan, etoposide, and prednisone), EVAP (i.e., etoposide, vinbiastine, cytarabine, and cisplatin), and EPOCH (i.e., etoposide, vincristine, doxorubicin, cyclophosphamide, and prednisone).

In one aspect, wherein when said cancer is breast cancer, the use further comprising use of a treatment selected from paclitaxel, docetaxel, nanoparticle albumin bound paclitaxel, capecitabine, doxorubicin, eribulin, vinorelbine, trastuzumab, carboplatin, cisplatin; endocrine therapies including tamoxifen, anastrozole, letrozole, exemestane, fulvestrant, and cell cycle inhibitors including palbocilib, ribociclib, LEE001, and everolimus; immune checkpoint inhibiting drugs including nivolumab and pembrolizumab, either individually or in combination.

In one aspect, wherein when said cancer is small cell lung cancer, the use further comprising a use of a treatment selected from carboplatin, cisplatin, etoposide, irinotecan, either individually or in combination.

In one aspect, wherein when said cancer is non-small cell lung cancer, the use further comprising use of a treatment selected from carboplatin, paclitaxel, docetaxel, gefitinib, erlotinib, afatinib, bevacizumab, ramucirumab, osimertinib, necitumumab, crizotinib, ceritinib, alectinib, and immune checkpoint inhibiting drugs including nivolumab, pembrolizumab, either individually or in combination.

In one aspect, wherein when said cancer is bladder carcinoma, the use further comprising a use of a treatment selected from methotrexate, vincblastine, doxorubicin, cisplatin; carboplatin and paclitaxel; docetaxel, gemcitabine and cisplatin, either individually or in combination.

In one aspect, wherein the determination of hypermethylation in the NMT2 gene is performed by a method selected from the group consisting of PCR, methylation-specific PCR, realtime methylation-specific PCR, PCR assay using a methylation DNA-specific binding protein, quantitative PCR, DNA chip-based assay, pyrosequencing, and bisulfite sequencing.

In one aspect, wherein said biological sample comprises, a tissue, a cell specimen or fluids includes detached tumor cells and/or free nucleic acids, a blood sample, a fractionated blood sample, a bone marrow sample, a biopsy sample, a frozen tissue sample, a fresh tissue specimen, a cell sample, and/or a paraffin embedded section.

In one aspect, wherein said subject is a human.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
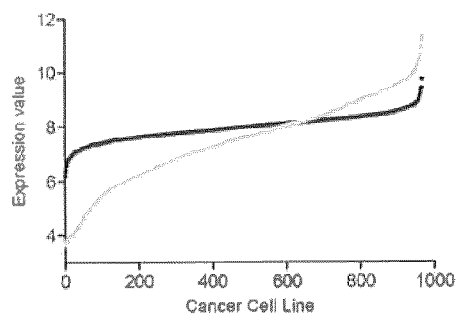
FIG. 1 depicts NMT2 expression is decreased in several cancer cell lines in the CCLE database and in tumours from TCGA database. NMT2 (grey) has a broader range of mRNA expression than NMT1 (black) in cancer cell lines (Panel A) and tumours (Panel B). Box plot of NMT2 mRNA expression in cancer-specific cell lines and tumour types. **, p<0.0001 vs. all tumours by t test, #, data not available (Panels C, D, E). NMT2 mRNA copies determined by droplet digital PCR in various lymphocytic cell lines (Panel F). Specific NMT activity in the cell lines in (Panel G) *, p<0.05. Kaplan-Meier plots show the progression-free survival (PFS) of 470 DLBCL patients (GSE31312) with high (red; top curve) versus low (blue; bottom curve) NMT2 expression (Panel H). P value was determined by log-rank test. All values are mean±s.e.m. of 3 independent experiments.
Figure 1:
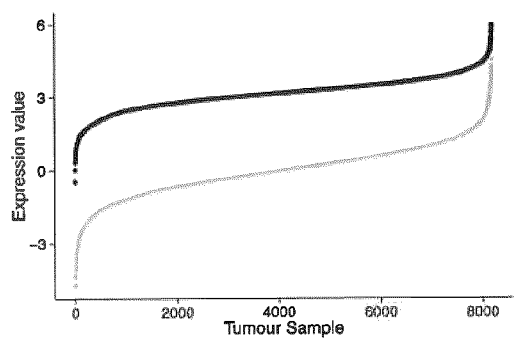
Figure 1:
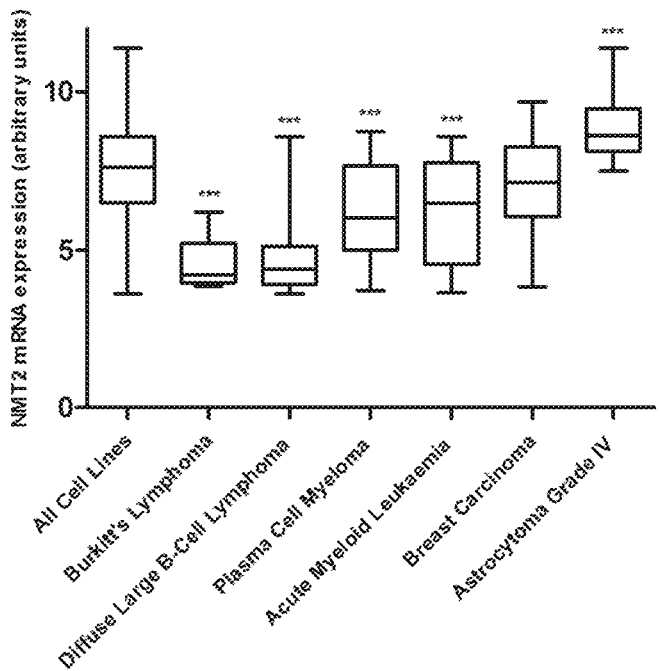
Figure 1:
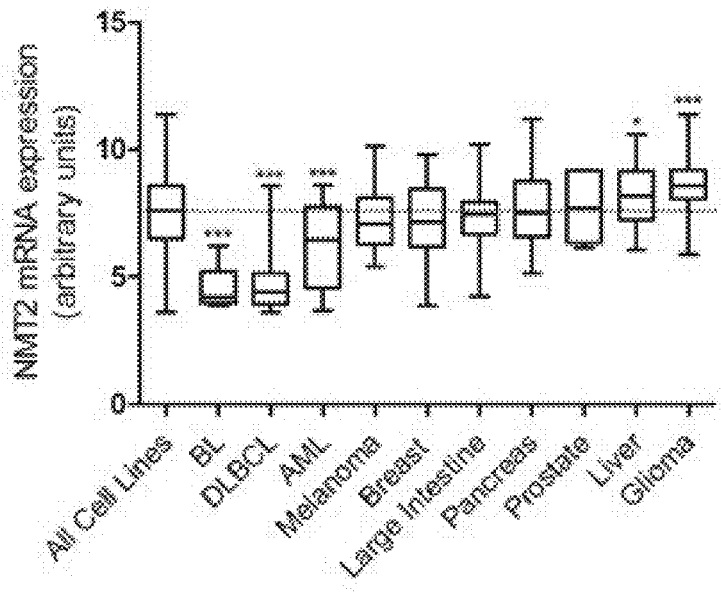
Figure 1:
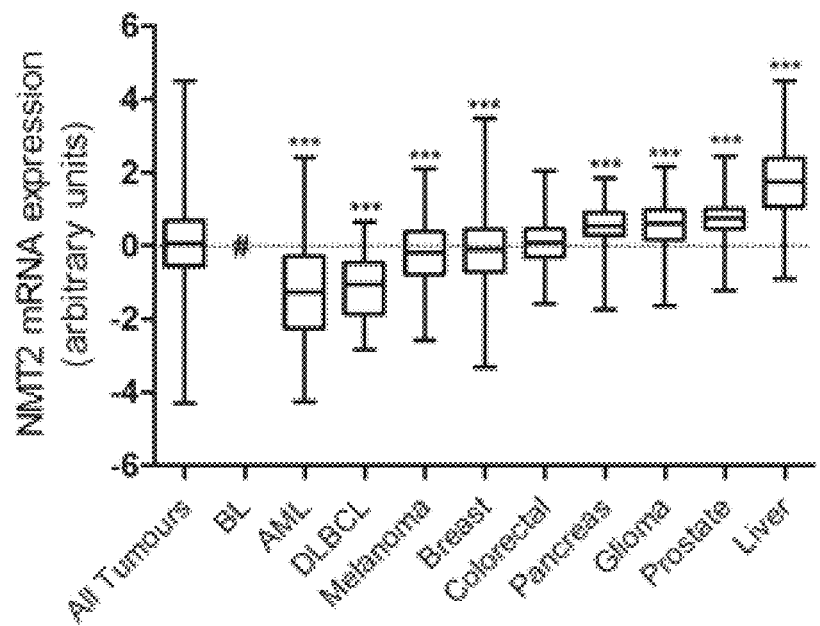
Figure 1:
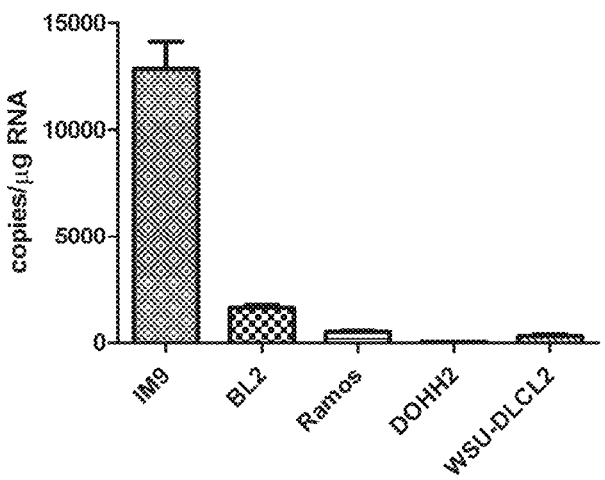
Figure 1:
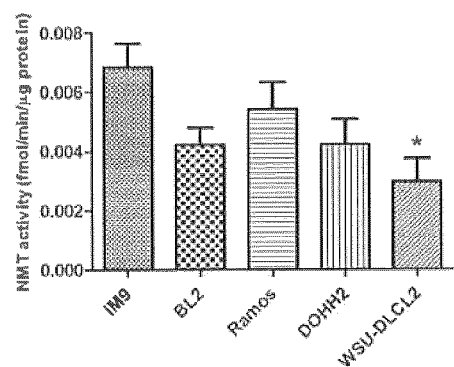
Figure 1:
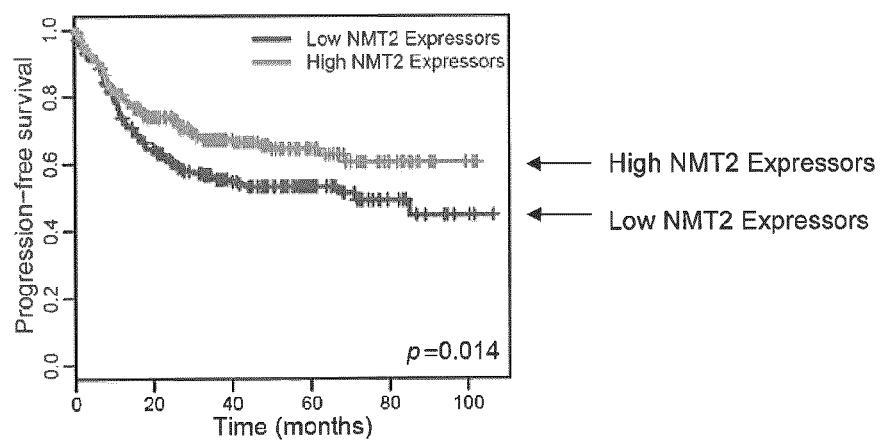

As will be described in more detail below, there is described herein compounds, composition and methods for the treatment of a subject with cancer. There are also described here methods for identifying subject with cancer that are suitable for treatment with the compounds, composition and methods are described herein.

Cells need at least one NMT to survive. The finding that multiple cancers lack one of two NMTs, while stromal and normal tissues do not, enables the treatment of NMT2-deficient cancer cells with an NMT inhibitor. See WO2013/013302 and WO2014/067002, the entire contents of which are hereby incorporated by reference in their entirety.

It is shown herein that NMT2 expression is reduced or eliminated in certain cancers, and in one example lymphomas, via an epigenetic mechanism(s). Reduction or elimination of NMT2 expression renders the cancer sensitive inhibitors of NMT.

In some examples, determination of the methylation status of NMT2 gene may be used to identify cancers which will respond to treatment with NMT inhibitors.

Cancers

The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. Cancer cells may be in the form of a tumour, but such cells may also exist alone within a subject, or may be a non-tumorigenic cancer cell. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

In a specific example of the present disclosure, the cancer is lymphoma.

The term "lymphoma" as used herein refers to a malignant growth of B or T cells in the lymphatic system. "Lymphoma" includes numerous types of malignant growths, including Hodgkin's Lymphoma and non-Hodgkin's lymphoma. The term "non-Hodgkin's Lymphoma" as used herein, refers to a malignant growth of B or T cells in the lymphatic system that is not a Hodgkin's Lymphoma (which is characterized, e.g., by the presence of Reed-Sternberg cells in the cancerous area). Non-Hodgkin's lymphomas encompass over 29 types of lymphoma, the distinctions between which are based on the type of cancer cells.

In a more specific example of the present disclosure, the cancer is a B-lymphoma.

Thus, in one embodiment, the compounds, compositions and methods of the disclosure are suitable for the treatment of a subject with B cell lymphoma.

Examples of B-cell lymphomas include, but are not limited to, for example, follicular lymphoma, diffuse large B-cell lymphoma, mantle cell lymphoma, B-CLL/SLL, immunocytoma/Waldenstrom's, and MALT-type/monocytoid B cell lymphoma. Also contemplated are the treatment of pediatric lymphomas such as Burkitts lymphoma, diffuse large B-cell lymphoma, follicular lymphoma, precursor B-LBL, precursor T-LBL, and anaplastic large cell lymphoma.

In other embodiments, the cancer is lymphoma, B cell lymphoma, follicular lymphoma, diffuse large B-cell lymphoma, mantle cell lymphoma, B-CLL/SLL, immunocytoma/Waldenstrom's, MALT-type/monocytoid B cell lymphoma, Burkitt's lymphoma, a pediatric lymphoma, anaplastic large cell lymphoma, acute myeloid leukemia, Blast Phase Chronic Myeloid Leukaemia, Burkitt's Lymphoma, Plasma Cell Myeloma, Intestinal Adenocarcinoma, Lung mixed Adenosquamous Carcinoma, Lung Small Cell Carcinoma, Lung, Oesophagus Squamous Cell Carcinoma, Bone, Breast Ductal Carcinoma, Stomach Diffuse Adenocarcinoma, Thyroid Medullary Carcinoma, urinary Tract Transitional Cell Carcinoma, myeloma, ovarian clear cell carcinoma, transition cell carcinoma (ureter and bladder cancer), chronic myelogenous leukemia (CML), lymphoma-CLL, breast carcinoma, colorectal adenocarcinoma, pancreas adenocarcinoma, ovarian carcinoma, non-small cell lunch carcinoma, osteosarcoma, melanoma, gastric adenocarcinoma, endometrial adenocarcinoma, or esophageal squamous carcinoma.

The term "subject" or "patient" as used herein, refers to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human.

The term "treatment" or "treat" as used herein, refers to obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early cancer, for example an early stage lymphoma, can be treated to prevent progression or alternatively a subject in remission can be treated with a compound or composition described herein to prevent recurrence.

The term "sample" or "biological sample" as used herein refers to any sample from a subject, including but not limited to a fluid, cell or tissue sample that comprises cancer cells, or which is suspected of containing cancer cells, which can be assayed for epigenetic modification, gene expression levels, protein levels, enzymatic activity levels, and the like. In a specific example, the sample it assayed for epigenetic modification. In another specific example, the epigenetic modification is methylation or acetylation. The sample may include, for example, a blood sample, a fractionated blood sample, a bone marrow sample, a biopsy sample, a frozen tissue sample, a fresh tissue specimen, a cell sample, and/or a paraffin embedded section, material from which DNA can be extracted in sufficient quantities and with adequate quality to permit measurement of epigenetic modification(s).

Inhibitors of NMT

In a specific aspect, said NMT inhibitor comprises a small molecule, an antibody, a peptide fragment, a nucleic acid, or combinations thereof.

In a specific aspect, said small molecule comprises DDD85646, the pyrazole sulphonamide inhibitor of *T. brucei* NMT [J. A. Frearson et al (2010) Nature. 464.728-723)], or a derivative thereof.

In a specific aspect, said small molecule comprises Trs-DBA.

In a specific aspect, said small molecule comprises DDD86481 (also referred to as PCLX-001 and CCI-002 herein), or a derivative thereof.

DDD85646 and DDD86481 are shown in Table 1.

TABLE 1

Structure

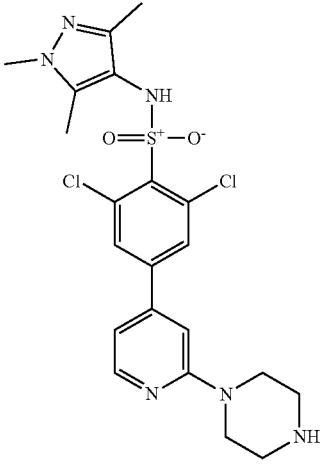 [SMILES: Cc1nn(C)c(C)c1N[S+](=O)([O-])c1c(Cl)cc(-c2ccnc(N3CCNCC3)c2)cc1Cl]

DDD00085646

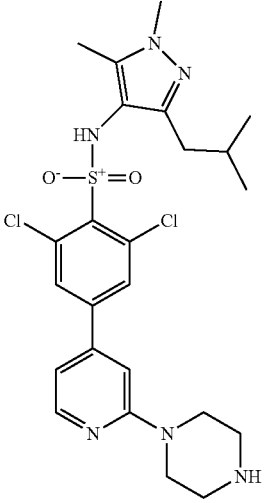 [SMILES: Cc1c(N[S+](=O)([O-])c2c(Cl)cc(-c3ccnc(N4CCNCC4)c3)cc2Cl)c(CC(C)C)nn1C]

DDD00086481

In a specific aspect, said antibody is a monoclonal antibody or a polyclonal antibody.

In a specific aspect, said nucleic acid comprises a dsRNA molecule, a RNAi molecule, a miRNA molecule, a ribozyme, a shRNA molecule, or a siRNA molecule.

Peptide fragments may be prepared wholly or partly by chemical synthesis that fit in the active site of NMT1. Peptide fragments can be prepared according to established, standard liquid or solid-phase peptide synthesis methods, which will be known to the skilled worker.

Nucleic acid inhibitors, or the complements thereof, inhibit activity or function by down-regulating production of active polypeptide. This can be monitored using conventional methods well known in the art, for example by screening using real time PCR as described in the examples.

Examples of nucleic acid inhibitors include anti-sense or RNAi technology, the use of which is to down-regulate gene expression is well established in the art. Anti-sense oligonucleotides may be designed to hybridize to the complementary sequence of nucleic acid, pre-mRNA or mature mRNA, interfering with the production of the base excision repair pathway component so that its expression is reduced or completely or substantially completely prevented. In addition to targeting coding sequence, anti-sense techniques may be used to target control sequences of a gene, e.g. in the 5' flanking sequence, whereby the anti-sense oligonucleotides can interfere with expression control sequences.

An alternative to anti-sense is to use a copy of all or part of the target gene inserted in sense, that is the same, orientation as the target gene, to achieve reduction in expression of the target gene by co-suppression.

Additionally, double stranded RNA (dsRNA) silencing may be used. dsRNA mediated silencing is gene specific and is often termed RNA interference (RNAi).

In another example, nucleic acid is used which on transcription produces a ribozyme, able to cut nucleic acid at a specific site and therefore also useful in influencing NMT.

In yet another example, small RNA molecules may be employed to regulate gene expression. These include targeted degradation of mRNAs by small interfering RNAs (siRNAs), post transcriptional gene silencing (PTGs), developmentally regulated sequence-specific translational repression of mRNA by micro-RNAs (miRNAs) and targeted transcriptional gene silencing.

In yet another example, the expression of a short hairpin RNA molecule (shRNA) in the cell may be used. A shRNA consists of short inverted repeats separated by a small loop sequence. One inverted repeat is complimentary to the gene target. In the cell the shRNA is processed by DICER into a siRNA which degrades the target NMT gene mRNA and suppresses expression. In a preferred embodiment the shRNA is produced endogenously (within a cell) by transcription from a vector.

The term "inhibit" or "inhibitor" as used herein, refers to any method or technique which inhibits protein synthesis, levels, activity, or function, as well as methods of inhibiting the induction or stimulation of synthesis, levels, activity, or function of the protein of interest, for example NMT1. The term also refers to any metabolic or regulatory pathway, which can regulate the synthesis, levels, activity, or function of the protein of interest. The term includes binding with other molecules and complex formation. Therefore, the term "inhibitor" refers to any agent or compound, the application of which results in the inhibition of protein function or protein pathway function. However, the term does not imply that each and every one of these functions must be inhibited at the same time.

Administration/Pharmaceutical Compositions

In other examples, the compounds and/or compositions are provided in a pharmaceutically effect amount suitable for administration to a subject.

The term "pharmaceutically effective amount" as used herein refers to the amount of a drug or pharmaceutical agent that will elicit the biological or medical response of a tissue, system, animal or human that is being sought by a researcher or clinician. This amount can be a therapeutically effective amount.

The compounds and compositions are provided in a pharmaceutically acceptable form.

The term "pharmaceutically acceptable" as used herein includes compounds, materials, compositions, and/or dosage forms (such as unit dosages) which are suitable for use in contact with the tissues of a subject without excessive toxicity, irritation, allergic response, or other problem or complication, commensurate with a reasonable benefit/risk ratio. Each carrier, excipient, etc. is also be "acceptable" in the sense of being compatible with the other ingredients of the formulation.

The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

A compound or composition may be administered alone or in combination with other treatments, either simultaneously or sequentially, dependent upon the condition to be treated.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

The compounds and compositions may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot/for example, subcutaneously or intramuscularly.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringers Solution, or Lactated Ringers Injection.

The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions comprising compounds disclosed herein may be used in the methods described herein in combination with standard chemotherapeutic regimes or in conjunction with radiotherapy.

Combination Therapy

In the case of cancer, and for example lymphoma, in a patient, known treatments are dependent upon the subject being treated, the type of disease, and its stage. Existing treatment modalities for various cancer, including for example for lymphoma, are known to the skilled worker. Accordingly, known treatments for cancer(s) may be used together with the NMT inhibitors disclosed herein.

Common drug combinations for use in treating lymphomas include, but are not limited, to CHOP (i.e., cyclophosphamide, doxorubicin, vincristine, and prednisone), GAP-BOP (i.e., cyclophosphamide, doxorubicin, procarbazine, bleomycin, vincristine, and prednisone), m-BACOD (i.e., methotrexate, bleomycin, doxorubicin, cyclophosphamide, vincristine, dexamethasone, and leucovorin), ProMACE-MOPP (i.e., prednisone, methotrexate, doxorubicin, cyclophosphamide, etoposide, leucovorin with standard MOPP), ProMACE-CytaBOM (prednisone, doxorubicin, cyclophosphamide, etoposide, cytarabine, bleomycin, vincristine, methotrexate, and leucovorin), and MACOP-B (methotrexate, doxorubicin, cyclophosphamide, vincristine, prednisone, bleomycin, and leucovorin). For relapsed aggressive non-Hodgkin's lymphoma the following chemotherapy drug combinations may be used with the compounds and compositions described herein: IMVP-16 (i.e., ifosfamide, methotrexate, and etoposide), MIME (i.e., methyl-gag, ifosfamide, methotrexate, and etoposide), DHAP (i.e., dexamethasone,—16 high dose cytarabine, and cisplatin), ESHAP (i.e., etoposide, methylprednisone, high dosage cytarabine, and cisplatin), CEFF(B) (i.e., cyclophosphamide, etoposide, procarbazine, prednisone, and bleomycin), and CAMP (i.e., lomustine, mitoxantrone, cytarabine, and prednisone).

Treatment for salvage chemotherapy used for certain lymphomas such as for relapsed, resistant Hodgkin's Disease include but are not limited to VABCD (i.e., vinbiastine, doxorubicin, dacarbazine, lomustine and bleomycin), ABDIC (i.e., doxorubicin, bleomycin, dacarbazine, lomustine, and prednisone), CBVD (i.e., lomustine, bleomycin, vinbiastine, dexamethasone), PCVP (i.e., vinblastine, procarbazine, cyclophosphamide, and prednisone), CEP (i.e., lomustine, etoposide, and prednimustine), EVA (i.e., etoposide, vinblastine, and doxorubicin), MOPLACE (i.e., cyclophosphamide, etoposide, prednisone, methotrexate, cytaravine, and vincristine), MIME (i.e., methyl-gag, ifosfamide, methotrexate, and etoposide), MINE (i.e., mitoquazone, ifosfamide, vinorelbine, and etoposide), MTX-CHOP (i.e., methotrexate and CHOP), CEM (i.e., lomustine, etoposide, and methotrexate), CEVD (i.e., lomustine, etoposide, vindesine, and dexamethasone), CAVP (i.e., lomustine, melphalan, etoposide, and prednisone), EVAP (i.e., etoposide, vinblastine, cytarabine, and cisplatin), and EPOCH (i.e., etoposide, vincristine, doxorubicin, cyclophosphamide, and prednisone).

Treatment for breast cancer includes treatment with paclitaxel, docetaxel, nanoparticle albumin bound paclitaxel, capecitabine, doxorubicin, eribulin, vinorelbine, trastuzumab, carboplatin, cisplatin; endocrine therapies including tamoxifen, anastrozole, letrozole, exemestane, fulvestrant, and cell cycle inhibitors including palbociclib, ribocidib, LEE001, and everolimus; immune checkpoint inhibiting drugs including nivolumab and pembrolizumab, either individually or in combination.

Treatment for small cell lung cancer includes treatment with carboplatin, cisplatin, etoposide, irinotecan, either individually or in combination.

Treatment for non-small cell lung cancer includes treatment with carboplatin, paclitaxel, docetaxel, gefitinib, erlotinib, afatinib, bevacizumab, ramucirumab, osimertinib, necitumumab, crizotinib, ceritinib, alectinib, and immune checkpoint inhibiting drugs including nivolumab, pembrolizumab, either individually or in combination.

Treatment for bladder carcinoma includes treatment with methotrexate, vincblastine, doxorubicin, cisplatin; carboplatin and paclitaxel; docetaxel, gemcitabine and cisplatin, either individually or in combination.

Epigenetic Mechanisms

As mentioned above, it is shown herein that NMT2 expression (i.e., NMT2 gene expression) is reduced or eliminated in certain cancers, and in one example lymphomas, via an epigenetic mechanism(s). Reduction or elimination of NMT2 expression renders the cancer sensitive inhibitors of NMT.

The term "epigenetic" as used herein refers to modification(s) in gene expression that is independent of DNA sequence.

Epigenetic factors include modifications in gene expression that are controlled by changes in DNA methylation (hypermethylation or hypomethylation), and chromatin structure.

For example, DNA methylation patterns are known to correlate with gene expression. DNA methylation occurs at the 5-position of cytosines at CpG sites.

In other example, epigenetic changes are altered acetylation patterns or levels.

Epigenetic Mechanisms—Methylation

In some examples herein, determination of the methylation status of NMT2 gene may be used to identify cancers, which will respond to treatment with NMT inhibitors.

The term "methylation status" as used herein, refers to the level of methylation of cytosine residues in CpG sites in a gene, for example NMT2. CpG sites include CpG pairs, CpG islands, and CpG island shores.

The term "CpG island" refers to a genomic DNA region that contains a high percentage of CpG sites relative to the average genomic CpG incidence In the example of CpG pairs, the methylation status may be methylated or unmethylated. In the example of CpG islands or CpG island shores, or to any stretch of residues, the methylation status refers to the level of methylation, which is the relative or absolute concentration of methylated C at the particular CpG island or CpG island shore or stretch of residues in a biological sample.

Methylation of a CpG sites or CpG island at a promoter typically reduces or eliminates expression of the gene.

CpG sites or CpG islands may surround the 5' region of the coding region of the gene as well as the 3' region of the coding region. Accordingly, CpG sites or CpG islands can be found in multiple regions of a nucleic acid sequence including upstream of coding sequences in a regulatory region including a promoter region, in the coding regions (e.g., exons), downstream of coding regions in, for example, enhancer regions, and in introns. All of these regions can be assessed to determine their methylation status, as appropriate.

The levels of methylation of the NMT2 gene, for example hypermethylation of NMT2 or hypomethylation of NMT2, may be determined by any suitable means in order to reflect the expression level of NMT2.

The term "expression level" as used herein refers to the level of gene expression.

The term "gene" as used herein refers to a nucleic acid (for example DNA) sequence that comprises coding sequences necessary for the production of a polypeptide such as NMT2, RNA (e.g., including but not limited to, mRNA, tRNA and rRNA) or precursor. The polypeptide, RNA, or precursor may be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb, and in some example greater than 1 kb, on either end such that the gene corresponds to the length of the full-length mRNA.

The term "hypermethylation" as used herein refers to the average methylation status corresponding to an increased presence of 5-methyl cytidine at one or a more of CpG CpG site or CpG island within a DNA sequence, for example the NMT2 gene, of a test DNA sample, relative to the amount of 5-methyl cytidine at corresponding CpG site or CpG island within a "normal" and/or control DNA sample.

In some example, hypermethylation refers to an of about 1%, about 5%, about 10%, about 20%, about 25%, about 30%, about 35%, about 40%, about 45%, about 50%, about 60%, about 65%, about 70%, about 75%, about 80%, about 85%, about 90%, about 95%, or more than about 95% greater than the extent of methylation of cytosines typically expected or observed for the CpG site or sites being evaluated. It will be appreciated that methylation varies under different metabolic conditions, stress, etc, as would be know to a skilled worker. In some example, hypermethylation refers to methylation at a single cytidine.

The term "hypomethylation" as used herein refers to the average methylation status corresponding to a decreased presence of 5-methyl cytidine at one or a more of CpG CpG site or CpG island within a DNA sequence, for example the NMT2 gene, of a test DNA sample, relative to the amount of 5-methyl cytidine at corresponding CpG site or CpG island within a "normal" and/or control DNA sample.

Typically CpG motifs reside near the transcription start site, for example, within about 3 kbp, within about 2.5 kbp, within about 2 kbp, within about 1.5 kbp, within about 1 kbp, within about 750 bp, or within about 500 bp In some examples, CpG islands are less than 100 base pairs, between 100 and 200 base pairs, between 200 and 300 base pairs, between 300 and 500 base pairs, between 500 and 750 base pairs; between 750 and 1000 base pair; 100 or more base pairs in length.

In some examples, the methylation status of the NMT2 gene is determined to be hypermethylation. In some examples, the methylation status of NMT2 is determined to be hypomethylation.

In the example in which the methylation of the NMT2 gene in a sample is determined to be hypermethylation, NMT2 expression is reduced or eliminated.

In the example in which the methylation of the NMT2 gene in a sample is determined to be hypomethylation, NMT2 expression is not reduced or eliminated.

The term "reduced expression" as used herein refers to a lesser expression level of a gene in a biological sample, compared to expression in a control or reference sample.

The methylation status of the NMT2 gene in a sample may be determined using a wide range of suitable devices and methods of methylation quantitation or detection, as would be known to the skilled worker.

Suitable devices include, but are not limited to lab-on-chip technology, microfluidic technologies, biomonitor technology, proton recognition technologies (e.g., Ion Torrent), and/or other highly parallel and/or deep sequencing methods.

Suitable methods of DNA methylation analysis include, but are not limited to, MALDI-TOFF, MassARRAY, Methy Light, Quantitative analysis of ethylated alleles (QAMA), enzymatic regional methylation assay (ERMA), HeavyMethyl, QBSUPT, MS-SNuPE, MethylQuant, Quantitative PCR sequencing, and Oligonucleotide-based microarray systems.

Further suitable method of DNA methylation analysis include, but are not limited to, methylation-specific PCR (MSP), bisulfite sequencing (also referred to as a sequencing of DNA treated with bisulfite to convert Methylated Cytosine to Uracil), pyrosequencing, methylation-sensitive DNA restriction enzyme analysis, quantitative bisulfite pyrosequencing, bisulfite genomic sequencing PCR and AQAMA.

In some examples, determining of the methylation status of the NMT2 gene comprises determining the methylation frequency of the CpG island or CpG island shore. Determining of the level of a nucleic acid polymer with altered methylation is carried out in a variety of ways, and as noted above, including but not limited to, methylation-specific PCR, quantitative methylation-specific PCR, methylation-sensitive DNA restriction enzyme analysis, quantitative bisulfite pyrosequencing, next generation sequencing and bisulfite genomic sequencing PCR.

In some examples, methylation-sensitive restriction endonucleases may be used to detect methylated CpG dinucleotidemotifs. Such endonucleases may either preferentially cleave methylated recognition sites relative to non-methylated recognition sites Non limiting examples include are Aat II, Ace III, Ad I, Acl I, Age I, Alu I, Asc I, Ase1, AsiS I, Ban I, Bbe I, BsaA I, BsaH I, BsiE I, BsiWI, BsrVI, BssK 1, BstB I, BstN I, Bs I, Cla I, Eae I, Eag I, Fau I, FseI, Hha I, mPI I, HinC II, Hpa 11, Npy99 I, HpyCAIV, Kas I, Mbo I, Mlu I, MapA 11. Msp I, Nae I, Nar I, Not 1, Pml I, PstI, Pvu I, Rsr II, Sac II, Sap I, Sau3A I, SflI, Sfo I, SgrA I, Sma I SnaB I, Tsc I, Xma I, and Zra I. In some example, endonucleases preferentially cleave non-methylated relative to methylated recognition sites. Non limiting examples include Ace II, Ava I, BssH II, BstU I, Hpa II, Not I, and Mho I.

In some examples, chemical reagents can be used that selectively modify either the methylated or non-methylated form of CpG dinucleotide motifs. Modified products can be detected directly, or after a further reaction which creates products that are easily distinguishable. Means which detect altered size and/or charge can be used to detect modified products, including but not limited to electrophoresis, chromatography, and mass spectrometry. Examples of such chemical reagents for selective modification include hydrazine and bisulfite ions. Hydrazine-modified DNA can be treated with piperidine to cleave it. Bisulfite ion-treated DNA can be treated with alkali. Other means for detection that are reliant on specific sequences can be used, including but not limited to hybridization, amplification, sequencing, and ligase chain reaction. Combinations of such techniques can be used as is desired.

NMT2 Epigenetic Modification—a Marker for One or More of Diagnosis, Prognosis, Classifying, Stratifying, or Monitoring, of a Cancer in a Subject.

Determination of the methylation status of NMT2 may be used to monitor efficacy of a therapeutic regimen, for example, a chemotherapeutic agent or a biological agent, such as an inhibitor of NMT.

Determination of the methylation status of NMT2 may also be used to determine what therapeutic or preventive regimen to employ on a patient.

Determination of the methylation status of NMT2 may also be used to stratify patients into groups for testing agents and determining their efficacy on various groups of patients. Such uses characterize the cancer into categories based on the genes, which are epigenetically silenced and/or the amount of silencing of the genes. In the case of a diagnosis or characterization, information comprising data or conclusions can be written or communicated electronically or orally. The identification may be assisted by a machine. Communication of the data or conclusions may be from a clinical laboratory to a clinical Office, from a clinician to a patient, or from a specialist to a generalist, as examples. The form of communication of data or conclusions typically may involve a tangible medium or physical human acts.

In one example, a test sample obtainable from tissue or cell specimens or fluids includes detached tumor cells and/or free nucleic acids that are released from dead or damaged tumor cells.

Nucleic acids include RNA, genomic DNA, mitochondrial DNA, single or double stranded. Any nucleic acid specimen in purified or non-purified form obtained from such sample may be utilized. The test samples may contain cancer cells or pre-cancer cells or nucleic acids from them. In s specific example, genomic DNA is isolated.

Demethylating agents can be contacted with cells in vitro or in vivo for the purpose of restoring normal gene expression to the cell or for validation of methylation. Suitable demethylating agents include, but are not limited to 5-aza-2'-deoxycytidine, 5-azacytidine, Zebularine, procaine, and L-ethionine. This reaction may be used for diagnosis, for determining predisposition, and for determining suitable therapeutic regimes.

In one example, determination of the methylation status of NMT2 is for determining the condition(s) for the risk of developing cancer, metastasis, tumour relapse, prediction of the response to a treatment, the identification and/or selection of a cancer, such as lymphoma, the selection of a suitable treatment regimen, stratification of a patient, and the treatment of a patient.

In certain embodiments of the invention, the methylation status is determined in part or wholly on the basis of a comparison with a control. The control can be a value or set of values related to the extent and/or pattern of methylation in a control sample. In certain embodiments of the invention, such a value or values may be determined, for example, by calculations, using algorithms, and/or from previously acquired and/or archived data. In certain embodiments of the invention, the value or set of values for the control is derived from experiments performed on samples or using a subject. For example, control data can be derived from experiments on samples derived from comparable tissues or cells, such as normal tissue adjacent to tumors.

In certain embodiments of the invention, a control comprising DNA that is mostly or entirely demethylated, at one or more of the CpG sites being analyzed, is used. Such a control may be obtained, for example, from mutant tissues or cells lacking methyltransferase activity and/or from tissues or cells that have been chemically demethylated. For example, controls may be obtained from tissues or cells lacking activity of methyltransferases. Agents such as 5-aza-2'-deoxycytidine may be used to chemically demethylate DNA.

In certain embodiments of the invention, a control comprising DNA that is mostly or entirely methylated, at one or more of the CpG sites being analyzed, is used. Such a control may be obtained, for example, from cells or tissues that are known or expected to be mostly or entirely methylated at the CpG site or sites of interest. Such a control could also be obtained by cells or tissues in which methylation levels have been altered and/or manipulated.

In one example, described herein is a method of predicting the response in a cancer patient, for example a lymphoma patient, to treatment of cancer. The drug for the treatment is an NMT inhibitor. In some examples, the NMT inhibitor is used in combination with at least one additional chemotherapy.

The presence of hypermethylation of NMT2 indicates that the NMT2 gene is methylated to a higher extent, which enables intervention with an NMT inhibitor. Therefore, the presence of hypermethylation of NMT2 indicates a more positive clinical response to said treatment, whereas the absence of methylation or a lower level of methylation compared to a control sample indicates an unsuccessful clinical response to the treatment with an NMT inhibitor. If a positive clinical response to treatment with an NMT inhibitor is determined, the patient is identified or selected for a treatment with said NMT inhibitor. In other cases, the patient is not selected for treatment with an NMT inhibitor, and one or more alternative drug or medical interventions may be more beneficial for the treatment of the cancer patient.

Accordingly, there is provided the use of NMT2 epigenetic modification, for example methylation of NMT2, as a marker for one or more of diagnosis, prognosis, classifying, or monitoring of cancer in a subject.

The term "prognosis" as used herein refers to the prediction of the likelihood of cancer-attributable death or progression, including recurrence, metastatic spread, and drug resistance, of a neoplastic disease, such as breast cancer.

The term "prognostic marker" as used herein refers to a marker that informs about the outcome of a patient in the absence of systemic therapy or portends an outcome different from that of the patients without the marker, despite empiric (not targeted to the marker) systemic therapy.

The term "predictive marker" as used herein refers to a marker that predicts that differential efficacy (benefit) of a particular therapy based on marker status.

The term "diagnosis" as used herein, refers to the identification of a molecular and/or pathological state, disease or condition, such as the identification of breast cancer, or other type of cancer.

Testing can be performed diagnostically or in conjunction with a therapeutic regimen.

Therefore, in one aspect, there is provided a method of predicting the response in a cancer patient (for example a lymphoma patient) to treatment with an NMT inhibitor comprising providing a biological sample of said cancer patient (for example the lymphoma patient), and determining in said biological sample the methylation status of the NMT2 gene, and predicting a positive clinical response to said treatment, if hypermethylation is determined in the NMT2 gene.

In another aspect, there is provided a method for identifying and/or selecting a patient with a cancer (for example a lymphoma), or treated for a cancer (for example a lymphoma), suitable for treatment with an NMT inhibitor, comprising providing a biological sample of cancer patient, and determining in the methylation status of the NMT2 gene, and identifying and/or selecting the cancer patient for treatment with said NMT inhibitor if hypermethylation is determined in the NMT2 gene.

Further provided is a method for selecting a suitable treatment regimen for a cancer (for example a lymphoma) in a cancer patient comprising providing a biological sample of said cancer patient, and determining in said biological sample the methylation status of the NMT2 gene, and selecting an NMT inhibitor for treatment if hypermethylation and/or under expression is determined in the NMT2 gene.

Further provided is a method of treating a patient with cancer (for example lymphoma) with an NMT inhibitor comprising providing a biological sample of said cancer patient, and determining in said biological sample the methylation status of NMT2, and selecting said NMT inhibitor for treatment if hypermethylation is determined in NMT2.

It will be appreciated that in some circumstances, a patient who initially responds to NMT inhibitor treatment may relapse. Such a relapse can manifest is several ways, including but not limited to, reoccurrence of the primary tumour and development of metastasis. In addition to, or alternatively, an additional distinct tumour can arise.

In accordance with one aspect of the present invention, there is provided a method comprising: a) obtaining a sample from a subject with, or suspected as having, cancer; b) contacting the sample a reagent to form a product (in some cases a complex) indicative of methylation status of NMT2 present in the sample; c) measuring the product formed to determine an amount or a concentration of methylated NMT2 in the sample; and d) determining the benefit of NMT inhibitor treatment of said cancer in in said subject, wherein the determination of benefit of NMT inhibitor treatment is determined by hypermethylation of NMT2 in said sample.

In a specific aspect, administering an NMT inhibitor to said subject is indicated when NMT2 is hypermethylated in said sample, optionally as compared to a control.

In accordance with one aspect, there is provided a method for treating cancer in a subject, comprising: a) obtaining nucleic acid from a sample from the subject; b) performing bisulfite modification to the nucleic acid in step a); c) performing a method selected from PCR, methylation-specific PCR, quantitative methylation specific PCR (QMSP), realtime methylation-specific PCR, PCR assay using a methylation DNA-specific binding protein, quantitative PCR, DNA chip-based assay, pyrosequencing, or bisulfite sequencing, on the bisulfite modified nucleic acid from step b) using PCR primers and/or probes specific for the promoter region of the NMT2 gene, e) determining a promoter methylation level of the promoter region of NMT2 in the sample, optionally compared to a control, g) treating said patient with an inhibitor to NMT when promoter methylation level of the promoter region of NMT2 gene in the sample is determined to be hypermethylated.

In accordance with one aspect, there is provided an in vitro assay for selecting a treatment for a patient with cancer, comprising: a) obtaining nucleic acid from a sample from the subject; b) performing bisulfite modification to the nucleic acid in step a); c) performing a method selected from PCR, methylation-specific PCR, quantitative methylation specific PCR (QMSP), realtime methylation-specific PCR, PCR assay using a methylation DNA-specific binding protein, quantitative PCR, DNA chip-based assay, pyrosequencing, or bisulfite sequencing, on the bisulfite modified nucleic acid from step b) using PCR primers and/or probes specific for the promoter region of the NMT2 gene, e) determining a promoter methylation level of the promoter region of NMT2 in the sample, optionally compared to a control, wherein the selected treatment is an NMT inhibitor when promoter region of NMT2 gene in the sample is determined to be hypermethylated.

In accordance with one aspect, there is provided an in vitro assay of a sample from a patient for selecting a treatment for a patient with cancer, comprising: a) performing bisulfite modification to the nucleic acid in said sample, b) determining methylation of the promoter of the NMT2 gene using PCR primers and/or probes specific for the promoter region of the NMT2 gene from step a).

In one aspect of the assay step b) is performed by a method selected from PCR, methylation-specific PCR, quantitative methylation specific PCR (QMSP), realtime methylation-specific PCR, PCR assay using a methylation DNA-specific binding protein, quantitative PCR, DNA chip-based assay, pyrosequencing, or bisulfite sequencing, the bisulfite modified nucleic acid from step a).

In one aspect, detection of hypermethylation of the NMT2 gene is performed with primers comprising SEQ ID NO: 1 and/or SEQ ID NO: 2.

In once aspect of the, there is proved a kit for selecting a suitable treatment for a cancer in a cancer patient, comprising: a) one or more reagents for determining the methylation status of the NMT2 gene from a sample of said cancer patient, wherein the selected treatment is an NMT inhibitor when promoter region of NMT2 gene in the sample is determined to be hypermethylated, b) instructions for the use thereof.

In one aspect, said reagents comprise PCR primers and/or probes specific for the promoter region of the NMT2 gene.

In one aspect, there is provided a use of an NMT inhibitor for treating a subject with a cancer wherein the NMT2 gene in a sample from said subject is determined to be hypermethylated.

In one aspect, there is provided a use of an NMT inhibitor for the manufacture of a medicament for treating a subject with a cancer wherein the NMT2 gene in a sample from said subject is determined to be hypermethylated.

Epigenetic Mechanisms—Acetylation

As noted above, in some example, the epigenetic modification is histone acetylation.

An additional mechanism underlying gene silencing involves histone acetylation. Histone acetylation is mediated by histone acetyl transferases, while acetyl groups are removed by histone deacetylase(s) (HDAC).

It is shown herein that that lymphoma cells aberrantly increase methylation (hypermethylation) and decrease acetylation (hypoacetylation) to silence NMT2.

There are several structurally distinct classes of HDAC inhibitors including, but not limited to, valproic acid, valproates, VPA; butyrates, NaB; vorinostat, SAHA; romidepsin, depsipeptide; belinostat, PXD101; trichostatin A, TSA; apicidin; etinostat, MS275; mocetinostat, MGCD0103; panobinostat, LBH589; givinostat, ITF2357; pracinostat, SB939; CHR-39961; chidamide, CS055, HBI-8000; AR-42; quisinostat, JNJ-26481585; abexinostat, PCI-24782; resminostat, 4SC-201, RAS2410; CG200745; M344, ME-344; WJ25591; A248; NK-HDAC-1; MHY219; Ky-2; HDACi 4b; OBP-801, YM753; DWP0016; BRD8430; largazole; adamantine; trifluoromethyloxadiazole (TFMO) series, eg TMP195; YK-4-272, compound 2 (see Katrina J. Falkenbergl and Ricky W. Johnstone (2014) NATURE REVIEWS | DRUG DISCOVERY. Vol 13. 673-691; and Andrew A. Lane and Bruce A. Chabner (2009) J Clin Oncol 27:5459-5468.) the contents all of which are hereby incorporated by reference, in their entirety.

Histone Acetyl Transferase Inhibitors, DNA Demethylase Inhibitors, and/or Histone Demethylase Inhibitors.

Histone acetyltransferases (HAT) are enzymes that acetylate conserved lysine amino acids on histone proteins by transferring an acetyl group from acetyl CoA to form e-N-acetyl lysine. Histone acetylation is generally linked to transcriptional activation. These are generally associated with euchromatin. Histone acetyltransferases (HATs) act as transcriptional coactivators. Histone acetylation plays an important role in regulating the chromatin structure and is tightly regulated by two classes of enzyme, histone acetyltransferases (HAT) and histone deacetylases (HDAC).

Non-limiting examples of HAT inhibitors include anacardic acid, CPTH2, MB-3, and Curcumin (Sigma-Aldrich).

DNA methyltransferases are a family of enzymes that catalyze the transfer of methyl group to DNA. There are five related DNA cytosine-5-methyltransferases (DNMTs) that transfer a methyl group from S-adenosylmethionine (AdoMet, SAM) to the C-5 position of cytosine. Inhibitors have been shown to have anti-proliferative activity.

Non-limiting examples of DNA Methyltransferase Inhibitors include 5-Azacytidine, Zebularine, Caffeic acid purum, Chlorogenic acid, (−)-Epigallocatechin gallate, Hydralazine, Procainamide hydrochloride, Procaine hydrochloride, Psammaplin A, and RG108 (Sigma-Aldrich).

DNA demethylation can be achieved either passively or actively, by a replication-independent process.

While methylations are performed by Histone Methyl Transferases (HMTs) using the ubiquitous methyl donor S-adenosyl-methionine, two different oxidation mechanisms for Histone DeMethylases (HDMs) have been shown to lead to demethylation. Lysine Specific Demethylase 1 (LSD1/KDM1) was the first HDM to be discovered. LSD1 oxidises the lysine methyl ammonium group by catalysing the overall transfer of hydrogen from the methyl amino group to FAD generating a methyliminium ion. Other known HDMs are from the Jumonji protein family, characterized by containing the JmjC domain Non-limiting examples of histone demethylase inhibitors include Daminozide, GSK J1, GSK J2, GSK J4, GSK J5, GSK LSD 1 dihydrochloride, IOX 1, JIB 04, RN 1 dihydrochloride, TC-E 5002, Tranylcypromine hydrochloride (Tocris—A Bio-Techne Brand).

In some examples herein, a subject with a subject with cancer or suspected of having cancer is treated with an NMT inhibitor, such as PCLX-001, as well as a histone acetyl transferase inhibitor, a DNA demethylase Inhibitor, and/or a histone demethylase inhibitor.

In some examples herein, a subject with a subject with a methylation status, which is hypermethylated, is treated with an NMT inhibitor, such as PCLX-001, as well as a histone acetyl transferase inhibitor, a DNA demethylase Inhibitor, and/or a histone demethylase inhibitor.

While not wishing to be bound by theory, it is believed that the histone acetyl transferase inhibitor, DNA demethylase Inhibitor, and/or histone demethylase inhibitor maintain the chromatin in a condensed form.

Methods of the invention are conveniently practiced by providing the reagents, compounds and/or compositions used in such method in the form of a kit. Such a kit preferably contains the composition. Such a kit preferably contains instructions for the use thereof.

To gain a better understanding of the invention described herein, the following examples are set forth. It should be understood that these example are for illustrative purposes only. Therefore, they should not limit the scope of this invention in any way.

EXAMPLES

In the following examples, standard methodologies were employed, as would be appreciated by the skilled worker.

Example 1

NMT expression levels in the 967 cancer cell lines encyclopedia (CCLE) database and 8178 primary tumours from The Cancer Genome Atlas (TCGA).

In FIG. 1, NMT2 shows a very large range of mRNA expression (log 2 normalized microarray fluorescence-3-11) compared to NMT1 (log 2 microarray fluorescence ~6-9) (FIG. 1A). NMT1 (black) and NMT2 (grey) expression values are log transformed RSEM normalized counts relative to TBP (TATA Binding Protein) (FIG. 1B). NMT2 mRNA expression of cancer cell lines from several cancer subtypes are plotted and compared to the plot of all 967 cancer cell lines (FIGS. 1C-E). Student T-tests were performed comparing each group to all tumours. "denotes P values <0.001. Absolute quantification NMT2 (Panel F) mRNA copies was measured by digital droplet PCR in Burkitt's lymphoma cell lines Ramos, and BL-2 and Diffuse Large B Cell lymphomas DOHH-2, WSU-DLCL2 compared to "immortalized" normal" B lymphocytic cell line IM-9 (n=3). Myristoylation activity in various Burkitt's lymphoma cell lines Ramos, and BL-2 and Diffuse Large B Cell lymphomas DOHH-2, WSU-DLCL2 compared to immortalized "normal" B lymphocytic cell line IM-9 (n=3) (FIG. 1G). NMT2 expression in relation to progression-free survival in adult DLBCL patients (FIG. 1H). Kaplan-Meier plots show the PFS of DLBC patients (GSE31312, n=470) with high (upper curve) versus low (lower curve) NMT2 expression (FIG. 1I). P values were determined by log-rank test.

Figure 2:
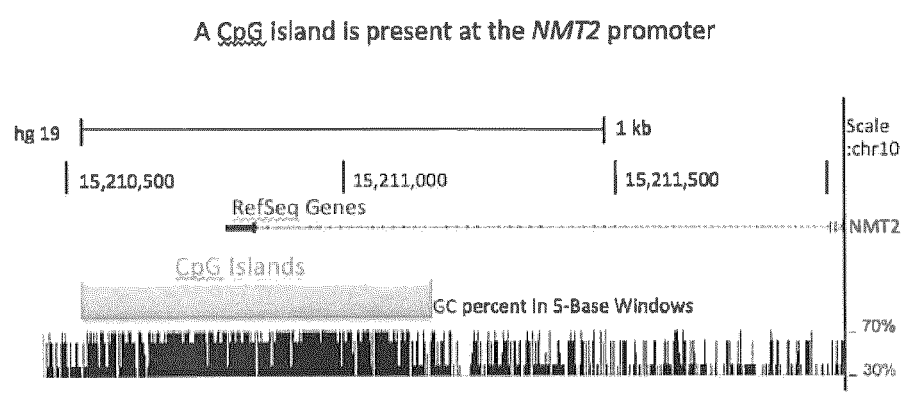
FIG. 2 depicts a CpG island at the NMT2 promoter (Panel A). Epigenetic regulation of NMT2 in lymphoma cell lines and tumours (Panel B) NMT2 expression (RSEM normalized counts) in TCGA tumours correlates negatively with NMT2 methylation values (cg02268561 beta values) at position 15,212,006 in WSU-DLCL2 (highlighted in red in Panel B). p=0.0082, Spearman correlation analysis, n=43 from the TCGA cohort). Bisulfite sequencing of DAPK1 promoter region reveals a highly methylated CpG containing promoter region only in malignant B lymphocytes (Panel C)
Figure 2:
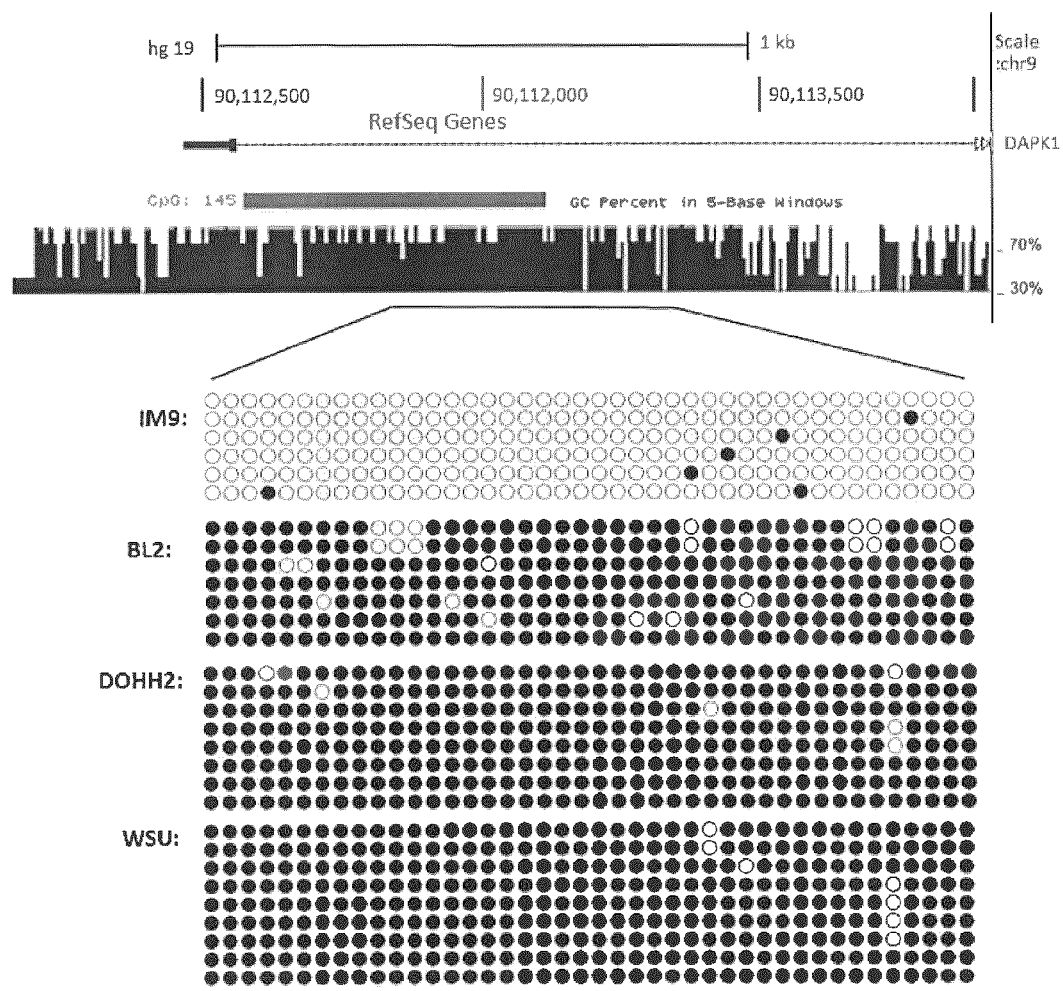
Figure 3:
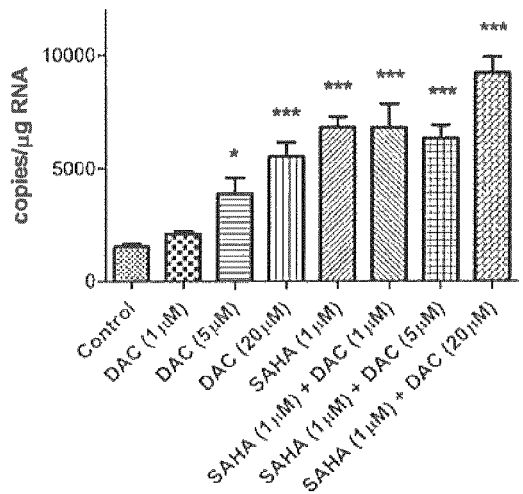
FIG. 3 depicts the number of NMT2 mRNA copies measured by digital PCR in various lymphocytic cell lines after a 24-h treatments with DAC in the presence or absence of SAHA (Panels A-D). NMT2 protein levels assessed by western blotting in BL2 (Panel E) and IM9 (Panel F) (normalized to GAPDH level) after 24-h treatments as above. Values are mean±s.e.m. of 3 independent experiments. (Panel G) NMT2 expression (RSEM normalized counts) in TCGA tumours correlates negatively with NMT2 methylation values (cg02268561 beta values) at position 15,212,006 in WSU-DLCL2 (highlighted in red in FIG. 2B). p=0.0082, Spearman correlation analysis, n=43 from the TCGA cohort depicts graphs and immunoblots.
Figure 3:
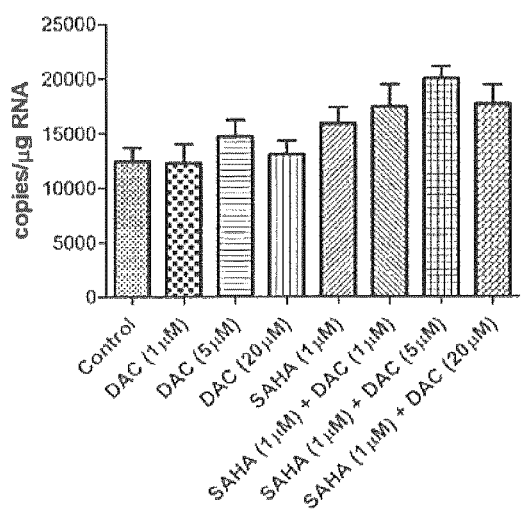
Figure 3:
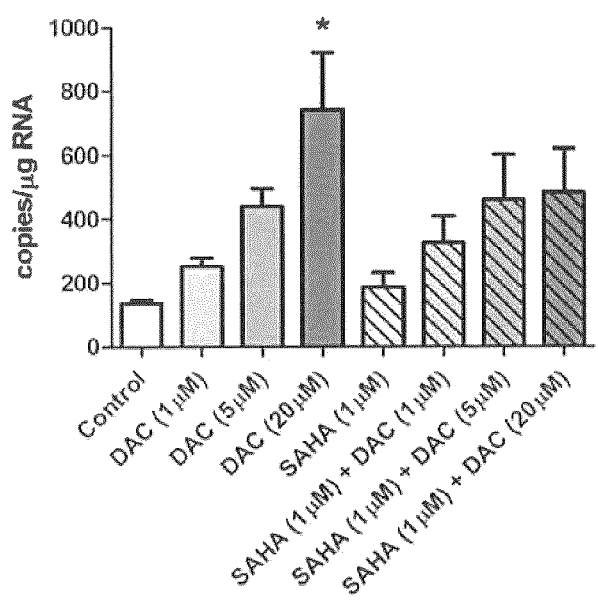
Figure 3:
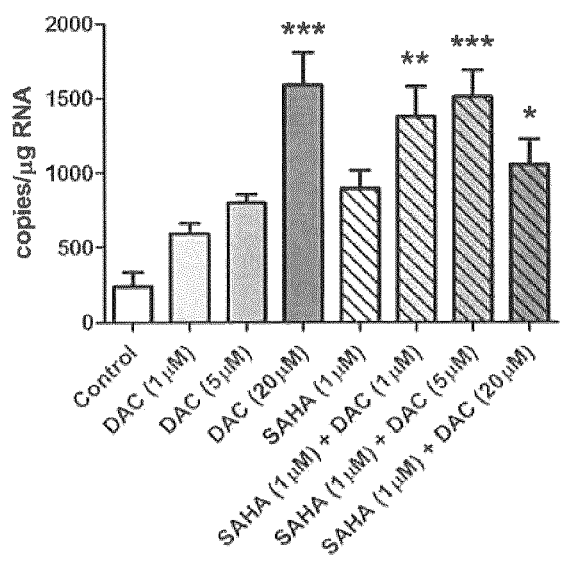
Figure 3:
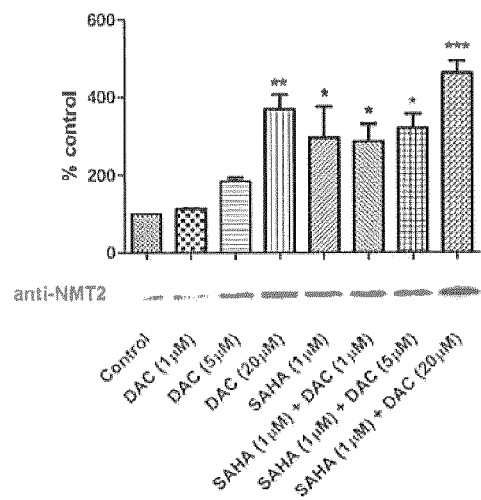
Figure 3:
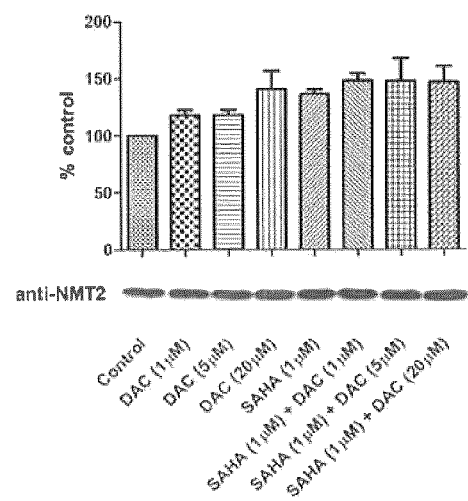
Figure 3:
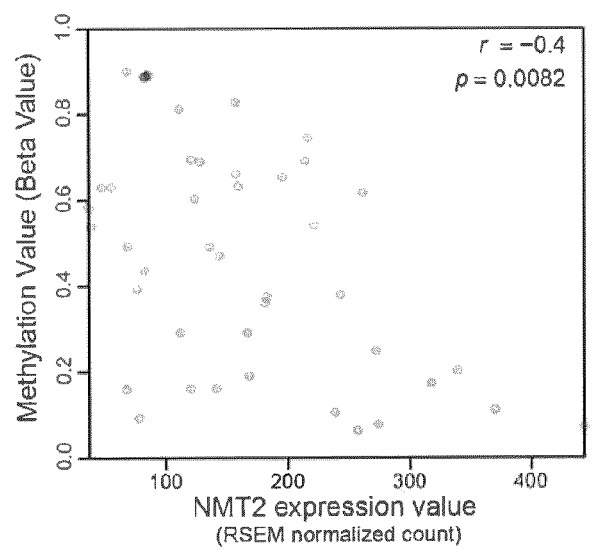

A prominent mechanism underlying gene silencing involves histone acetylation together with DNA methylation, most prominently at CpG islands. In silico analyses revealed a CpG island in the NMT2 5' regulatory region, shown in FIG. 2A. Bisulphite sequencing of DNA from lymphoma cell lines and immortalized IM9 B cells confirmed that the NMT2 locus was methylated in DOHH2 and WSU-DLCL2 lymphoma cells, but not in BL2 and benign IM9 cells (FIG. 2B). To validate the methylation status of the cell lines, we used DAPK1 as a control and found it to be highly methylated only in malignant B lymphocytes (FIG. 2C)

Thus, it is shown herein that NMT2 expression is commonly lost in lymphomas, and that this phenomenon is associated with more aggressive disease.

The loss of NMT2 expression in lymphomas was almost complete, suggesting epigenetically silencing of NMT2 in this cancer.

In order to establish a direct link between epigenetic modifications and the regulation of NMT2 expression in human lymphoma cell lines and tumours, we next treated cells with inhibitors of DNA methylation and histone deacetylation, deoxyazacytidine (DAC) and suberoylanilide hydroxamic acid (SAHA), respectively. Each produced time- and concentration-dependent recovery of NMT2 mRNA levels in lymphoma cells, and combined treatment with DAC and SAHA restored transcript levels in Ramos, BL2, DOHH2 and WSU-DLCL2 cells to those in untransformed IM9 cells (FIG. 3A-D). These inhibitors acted synergistically when added together. Treating BL2 cells with combination of DAC and SAHA increased NMT2 expression 6 fold resulting in NMT2 levels approximating those seen in IM-9 cells.

Absolute quantification of NMT2 mRNA copies were measured in BL2 (FIG. 3, panel A) and IM9 (FIG. 3, panel B) after 24h treatment with increasing concentration of demethylation agent (DAC) in the presence of histone deacetylase inhibitor (SAHA) (n=3). WSU-DLCL2 is shown FIGS. 3C and 3D.

NMT2 protein level quantification in BL2 (FIG. 3E) and IM9 (FIG. 3F) (normalized to GAPDH level) after 24h treatment with increasing concentration of demethylation agent (DAC) in the presence of histone deacetylase inhibitor (SAHA). Graphic representation of 3 independent experiments with 1 representative western blot.

Using data extracted from patient samples, we found an inverse correlation between NMT2 expression (RSEM normalized counts) and NMT2 methylation (beta value) status (spearman coefficient −0.4; p=0.0082) (FIG. 3G).

In BL2 cells, the increase in NMT2 mRNA after combined treatment was associated with increased protein levels (FIG. 3E-F). However, in DOHH2, and WSU-DLCL2 cells, NMT2 was not detected by western blotting despite significant increases in NMT2 mRNA levels upon treatment with DAC and/or SAHA. In patient samples, NMT2 expression correlated inversely with NMT2 methylation status (FIG. 3G).

Together, these results suggested that lymphoma cells aberrantly increase methylation and decrease acetylation to silence NMT2, and that this loss of expression is associated with a more aggressive disease.

Example 2

We next investigated the therapeutic potential of DDD86481 in vivo to determine if it could mitigate tumour progression.

We tested the potential tumoricidal effects of DDD86481 monotherapy in two lymphoma cell line-derived mouse xenograft (CDX) models developed by injecting $1 \times 10^7$ BL-2 (BL) or DOHH-2 (DLBCL) cells subcutaneously in the flank of immuno-compromised NODscid mice. DOHH-2 tumour (125-200 mm$^3$) bearing mice (n=10 per group) were injected subcutaneously with PCLX-001 into the opposite flank at doses of 10, 20, 50 daily (QD) or 50 (every other day, QOD)) mg per kg (mpk) or daily saline control.

We observed a dose-dependent tumoricidal effect, which gained statistical significance (p<0.05) when PCLX-001 was given at 20 mpk or 50 mpk QOD.

Figure 4:
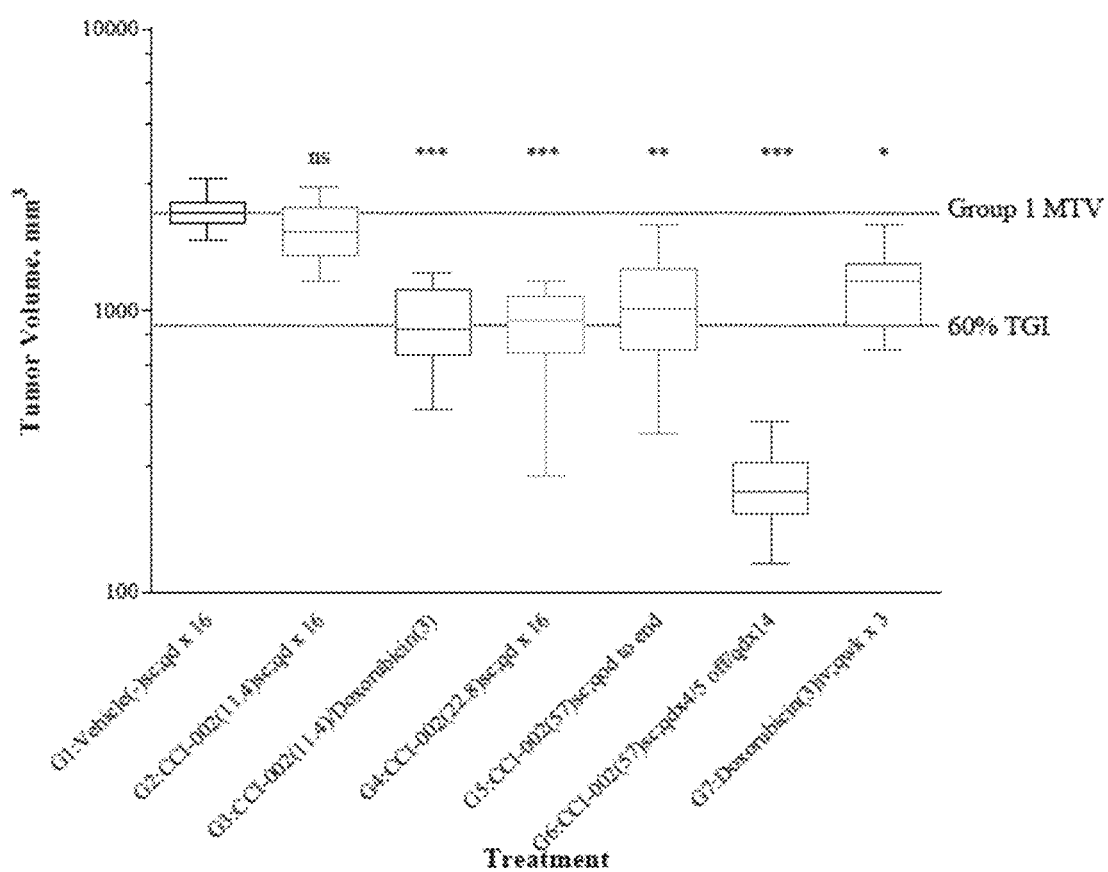
FIG. 4 shows a box and whiskers plot showing the distribution of individual mice tumor volumes in each group graphs (Panel A). PCLX-001 dose-response curves for xenografts derived from cell lines DOHH2 (Panel B); Combination therapy PCLX-001 and DOX dose-response curves for xenografts derived from cell lines DOHH2 (Panel C)
Figure 4B:
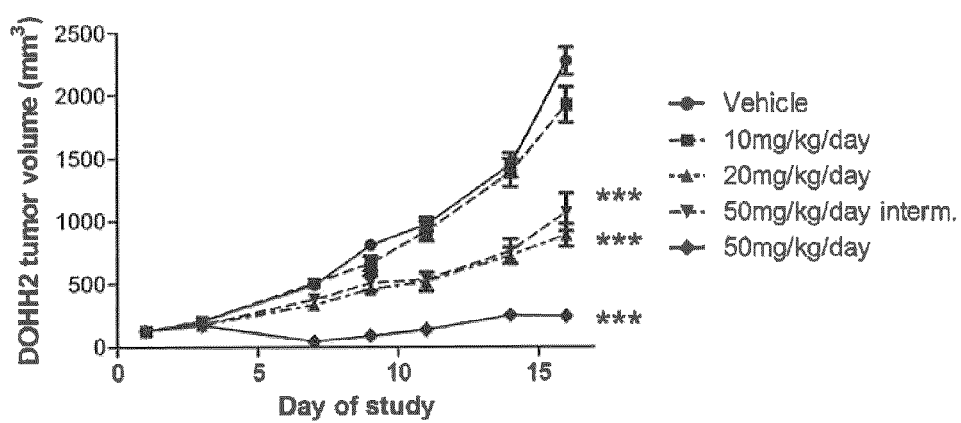
Figure 4:
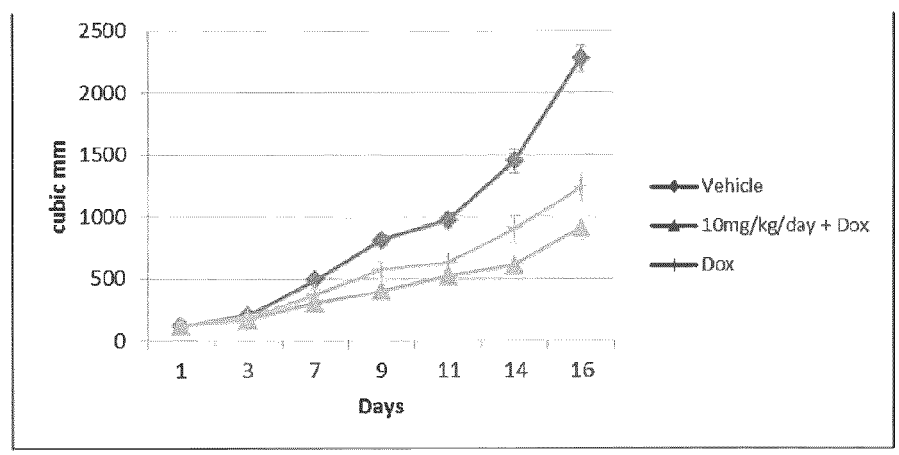

In mice bearing DOHH2 tumours (125-200 mm$^3$) (n=10 mice per group), PCLX-001 injected subcutaneously into the opposite flank had a significant, tumoricidal effect at 20 mg/kg daily or 50 mg/kg every other day (p<0.001) (FIG. 4B). When injected daily at 50 mg/kg, PCLX-001 shrank tumours by 70% (average tumour size, 44.0±8.1 mm3 at day 7). However, this was accompanied by some weight loss, necessitating a 5-day interruption in treatment (not shown). However, upon treatment resumption, a mean tumour growth inhibition (TGI) of 95% was observed by day 16. Importantly, tumour volume shrank in 6 of 10 mice between days 14 and 16, indicating that a longer treatment period might have proven beneficial.

Similarly, in mice bearing BL2 CDXs, PCLX-001 at 20 mg/kg led to 40% TGI by day 9 (p<0.05) (FIG. 5A).

PCLX-001 given at 50 or 60 mg/kg for 13 consecutive days caused tumours to disappear in 9 of 9 and 7 of 7 mice, respectively. It is not know whether the four mice that did not survive the higher daily doses died from drug toxicity or tumour lysis syndrome. Nonetheless, some of the mice died, and dosing at 60 mg/kg daily had no apparent benefit. Therefore, the maximal tolerated dose seems to be 50 mg/kg.

These results suggest that DDD86481 can reduce or eliminate NMT2-deficient B cell lymphoma tumours in vivo.

PCLX-001 also reduced total NMT specific activity in BL2 tumours (p<0.05) in a concentration-dependent manner (FIG. 5C). These results in two independent lymphoma CDX models confirm that PCLX-001 can eradicate NMT2-deficient B-cell lymphomas in vivo.

Since CDXs lack the complexity of human tumours, a strategy was developed to identify patients with NMT2-deficient DLBCLs by immunohistochemistry or RNA in situ hybridization (FIGS. 5D and 5E). We then dissected and propagated one such tumour from patient "DLCL3" to establish a DLBCL patient-derived xenograft (PDX) model in NODscid mice. The mean initial tumour volume was 240 mm$^3$ (FIG. 5F).

Treatment regimens were assessed in groups of 8 mice each. At 20 mg/kg daily for 21 days, PCLX-001 caused a TGI of 60% (p<0.001). At 50 mg/kg daily for two 9-day periods separated by a 3-day treatment suspension (to allow the mice to recover from the nearly 15% body weight loss), PCLX-001 caused the tumours to disappear in 6 of 7 surviving mice at day 13; one mouse with no detectable tumour died at day 7 (FIG. 5F). In surgically removed control and PCLX-001-treated PDX tumours, we confirmed the concentration-dependent reduction of tumour size (FIG. 5G). In the only remaining tumour from the 50-mg/kg treatment, PCLX-001 effectively induced apoptosis (FIG. 5H) and reduced cell proliferation (FIG. 5I). Thus, NMT2-deficient lymphomas can be identified and treated in a mouse PDX model. Moreover, the eradication of DLBCL PDX tumours in 7 of 8 mice suggests that the loss of NMT2 expression is an essential driver event in some DLBCL cases.

Example 3—DLBCL Xenograft Results

Seven groups of female SCID mice (n=10/group) were dosed s.c. to completion in accordance with the DOHH-2-e225 protocol in Table 2.

TABLE 2

Mouse protocol - DLBCL

| Group | Treatment |
|---|---|
| 1 | Control |
| 2 | CCI-002 at 10 mpk SC daily |
| 3 | CCI-002 at 10 mpk SC daily with doxorubicin 3 mpk once a week IV starting on day 0 |
| 4 | CCI-002 at 20 mpk SC daily |
| 5 | CCI-002 at 50 mpk SC every other day (QOD) |
| 6 | CCI-002 at 50 mpk SC daily (QD) × 4, rest 5 days, then resume 50 mpk SC daily (QD) |
| 7 | Doxorubicin 4 mpk once a week IV starting on day 0 |

FIG. 4A shows a box and whiskers plot showing the distribution of individual mice tumor volumes in each group.
FIG. 4B shows median tumor growth in monotherapy.
FIG. 4C shows median tumor growth in combination therapy.

Efficacy

Tumor Growth in Control Mice (Group 1)

Group 1 mice received vehicle on a qdx16 schedule starting on Day 1 and served as the control group for calculation of percent TGI and statistical comparisons. On Day 16, the median tumor volume (MTV) for Group 1 was 2213 mm$^3$, with a range of 1764 to 2944 mm$^3$ (FIG. 4A). Tumors engrafted in all ten control mice. Median tumor growth for Group 1 controls was progressive from the original tumor size 123.4+/−6.1 mm$^3$.

Response to Treatment with CCI-002 as a Daily Monotherapy (Groups 2 and 4)

Groups 2 and 4 were treated with CCI-002 at active dosages of 10 mg/kg and 20 mg/kg, respectively, s.c. qdx16 resulting in Day 16 MTVs of 1895 and 922 mm$^3$. These median tumor volumes (MTVs) corresponded to a non-significant TGI of 14% for Group 2 (P >0.05) and a significant TGI of 58% for Group 4 (P<0.001), which left both groups below the potential therapeutic activity threshold. Tumors engrafted in all treated mice.

Response to Treatment with CCI-002 & Doxorubicin Combination Therapy (Group 3)

Group 3 was treated with a combination of CCI-002 at an active dosages of 10 mg/kg s.c. qdx16 and doxorubicin i.v. qwkx3, resulting in a Day 16 MTVs of 864 mm$^3$. Group 3 had one animal that was euthanized on Day 11 due to excessive weight loss. That animal was sampled according to the protocol and classified as a NTR death and removed from all analyses. Group 3 had a MTV of 864 mm$^3$ corresponding to a significant TGI of 61% (P<0.001) which exceeded the potential therapeutic activity threshold (FIG. 4A). The Group 3 combination was significantly more effective than the corresponding CCI-002 monotherapy (Group 3 vs. 2, P<0.001) but not the corresponding doxorubicin treated group (Group 3 vs. 7, P >0.05). Tumors engrafted in all treated mice.

Response to Treatment with HIGH Dose CCI-002 Monotherapy (Groups 5 and 6)

Groups 5 and 6 were treated with CCI-002 at and active dosage of 50 mg/kg s.c. every other day qodx8 or qdx4/5 days off/qdx14, respectively, resulting in Day 16 MTVs of 1018 and 226 mm$^3$. These MTVs corresponded to significant TGIs of 54% for Group 5 (P<0.01) and 90% for Group 6 (P<0.001) with Group 6 above the potential therapeutic activity threshold (FIG. 4A). Tumors engrafted in all treated mice.

Response to Treatment with Doxorubicin Monotherapy (Group 7)

Group 7 was treated with doxorubicin at 3 mg/kg i.v. qwkx3 resulting in a Day 16 MTV of 1268 mm$^3$ corresponding to a significant TGI of 43% (P<0.05). Tumors engrafted in all treated mice.

SUMMARY

This study evaluated CCI-002 activity when dosed as a monotherapy and in combination with doxorubicin. Tumors were measured three times per week through the final day of the study (Day 23). The TGI analysis was performed on Day 16.

All therapy except Group 2 were significantly superior to the vehicle-treated control group (P<0.05). The CCI-002 at 50 mg/kg s.c. qdx4/5 days off/qdx14 treated group (Group 6) was the most effective regimen in this study with a MTV of 226 mm$^3$ which corresponded to a 90% TGI. The next most effective therapies included the CCI-002/doxorubicin combination group (Group 3), the CCI-002 monotherapy groups at 20 mg/kg and 50 mg/kg treated groups (Groups 4 and 5) which had respective TGI values of 61, 58 and 54% compared to control treated animals. There were no regressions recorded during the study.

All of the therapies tested in this DOHH-2 study were acceptably tolerated.

Example 4—Burkitt Lymphoma

Figure 5:
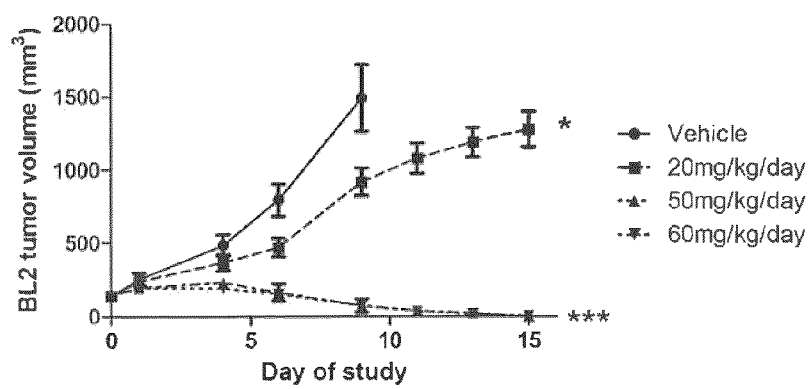
FIG. 5 PCLX-001 dose-response curves for xenografts derived from cell line BL2 (Panel A). Combination therapy PCLX-001 and DOX dose-response curves for xenografts derived from cell line BL2 (Panel B). Total NMT specific activity in BL2 tumour sample in Panels A (Panel C). Patient selection strategy for precision medicine (Panel D). Identification of NMT2-deficiency in DLBCLs from three patients by immunohistochemistry (IHC) and RNA in situ hybridization (ISH). Tumour from patient DLBCL3 is also shown after engraftment in mice (Panel E). PCLX-001 dose-response curves for the xenograft derived from patient 3 (Panel F). Representative tumours from mice with patient-derived xenografts (PDX) (Panel G). PCLX-001 treatment of mice with NMT2-deficient DLBCL3 PDX induces apoptosis (increase in cleaved caspase-3 staining) (Panel G) and reduces cell proliferation (reduction of Ki-67 staining) (Panel H). Shown are representative stained tumour slices for each treatment (Panel I).
Figure 5B:
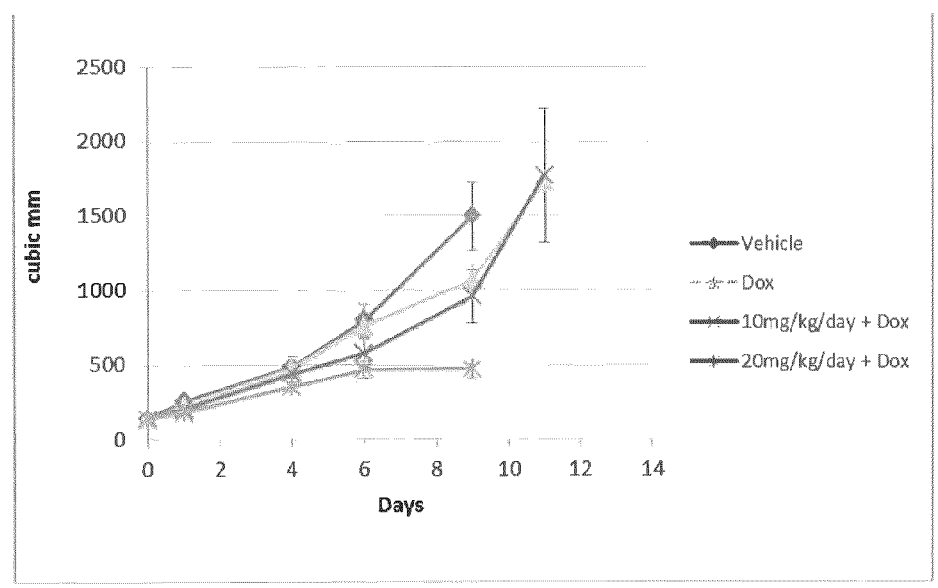
Figure 5:
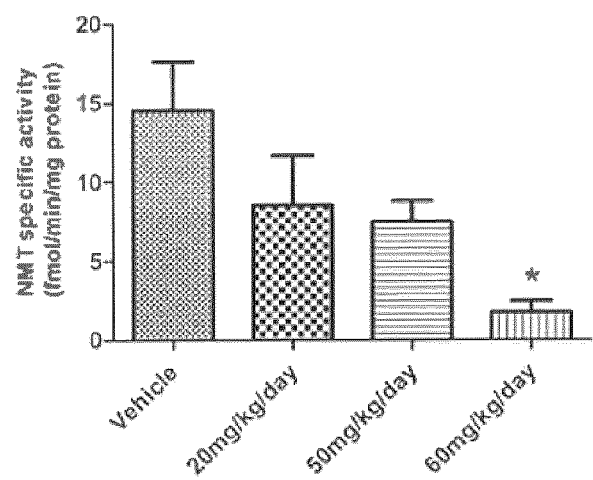
Figure 5:
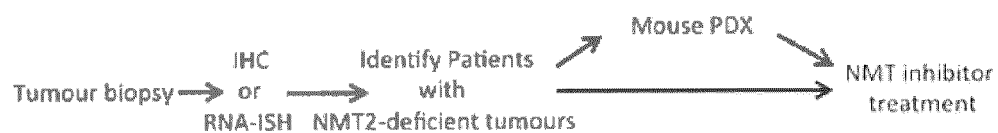
Figure 5:
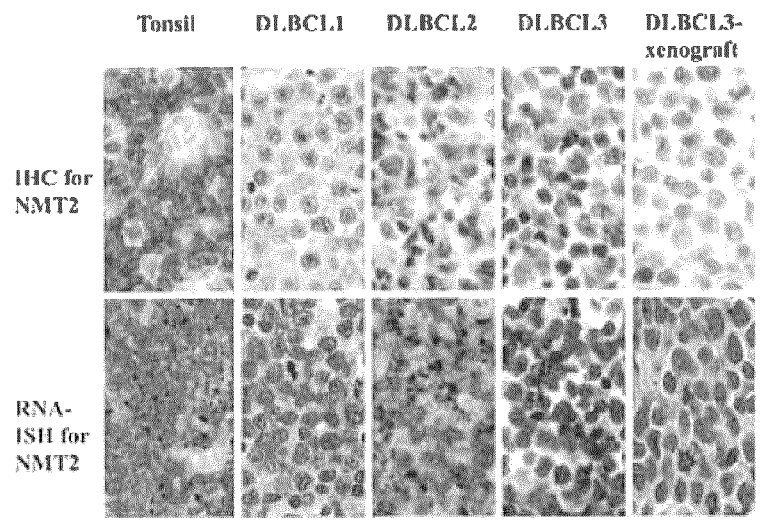
Figure 5:
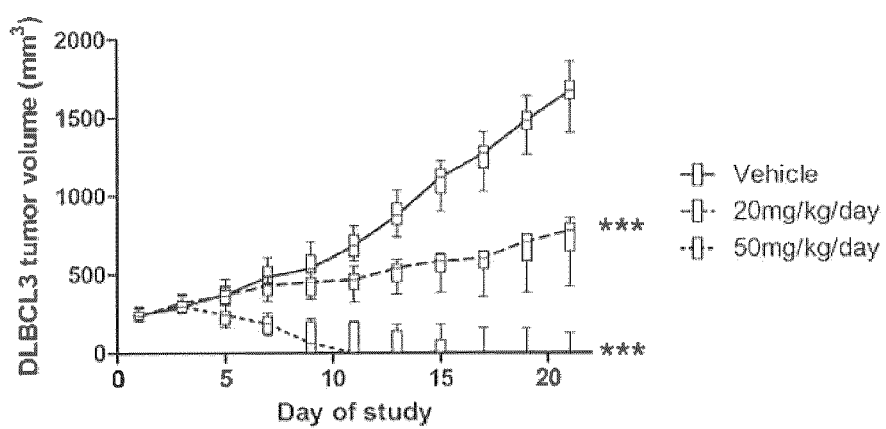
Figure 5:
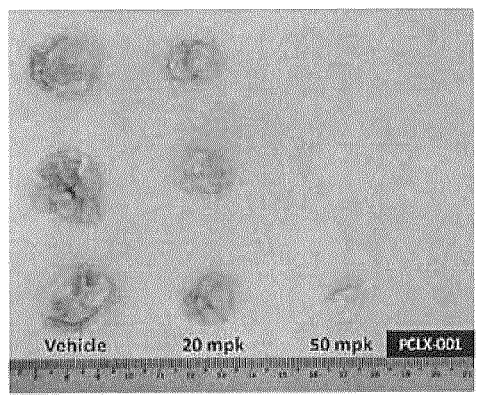
Figure 5:
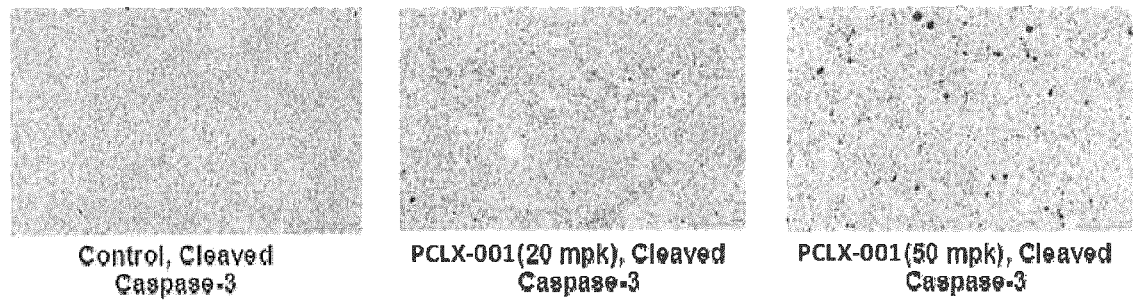
Figure 5:
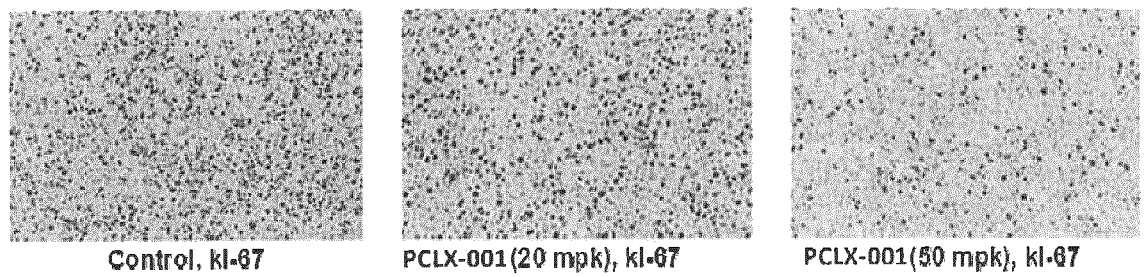

Seven groups of female NOD SCID mice (n=10/group) were dosed s.c. to completion in accordance with the DOHH-2-e225 protocol in Table 3 (below). The original treatment plan for this study can be found in Table 3. FIG. 5 shows average (n=10 per group) tumor volume, from Day 0 (A. monotherapy and B combination therapy with doxorubicin).

TABLE 3

Mouse protocol -BL-2

| Group | Treatment |
|---|---|
| 1 | Control |
| 2 | CCI-002 at 20 mpk SC daily |
| 3 | Doxorubicin 3 mpk once a week IV starting on day 0 |
| 4 | CCI-002 at 10 mpk SC daily and Doxorubicin once a week at 4 mpk IV |
| 5 | CCI-002 at 20 mpk SC daily and Doxorubicin once a week at 4 mpk IV |
| 6 | CCI-002 at 50 mpk SC daily |
| 7 | CCI-002 at 60 mpk SC daily |

Also, to reduce dehydration, on the first day of injection water bottles were removed and mice were provided with a rehydration solution made of NaCl: 4.5 g/L (0.45% final), Glucose (Dextrose): 25 g/L (2.5% final) and KCl: 0.75 g/L (0.075% final).

Results:

Tumor Growth in Control Mice (Group 1)

Group 1 mice received vehicle on a qdx9 schedule starting on Day 1 and served as the control group for calculation of percent TGI and statistical comparisons. On Day 9, the average tumor volume (ATV) for Group 1 was 1492 mm$^3$, with a range of 685 to 2742 mm$^3$. Tumors engrafted in all ten control mice. Median tumor growth for Group 1 controls was progressive from initial tumor volume of 255 mm$^3$.

Response to Treatment with CCI-002 as a Daily Monotherapy (Groups 26 and 7)

Groups 2, 6 and 7 were treated with CCI-002 at active dosages of 20 mg/kg, 50 mg/kg and 60 mg/kg, respectively, s.c. qdx16 resulting in Day 9 MTVs of 918, 74 and 72 mm$^3$. These average tumor volumes (ATVs) corresponded to a significant relative tumor growth inhibition of 38% for Group 2 (P<###) and highly a significant relative tumor growth inhibition of 95% for Group 6 and 7 (P<0.001), which left both groups 6 and 7 in the potential therapeutic activity threshold (TGI >60%) (FIG. 4A). Tumors engrafted in all treated mice. Average tumor growth in these groups is illustrated in FIG. 4A Median tumor volume reached 0 mm$^3$ by day 13 of the study therefore groups 6 and 7 treatments shows that CCI-002 causes 100% tumor regression.

Response to Treatment with Doxorubicin Monotherapy (Group 3)

Group 3 was treated with doxorubicin at 4 mg/kg i.v. qwkx3 resulting in a Day 9 MTV of 1061 mm$^3$ corresponding to a significant TGI of 29% (P<0.05). Tumors engrafted in all treated mice. Median tumor growth in these groups is illustrated in FIG. 4A.

Response to Treatment with CCI-002 & Doxorubicin Combination Therapy (Groups 4 and 5)

Group 4 was treated with a combination of CCI-002 at an active dosage of 10 mg/kg s.c. qdx16 and doxorubicin i.v. qwkx3, resulting in a Day 9 average tumor volume (ATV) of 952 mm$^3$ corresponding to a significant TGI of 36% (P<0.001). The Group 4 combination was not significantly more effective than the corresponding doxorubicin monotherapy (Group 4 vs. 3, P< >0.05##). Group 5 was treated with a combination of CCI-002 at an active dosage of 20 mg/kg s.c. qdx16 and doxorubicin i.v. qwkx3, resulting in a Day 9 average tumor volume (ATV) of 471 mm$^3$ corresponding to a significant TGI of 68% (P<0.001). The Group 5 combination was significantly more effective than the corresponding doxorubicin monotherapy (Group 5 vs. 3, P<0.05##).

Tumors engrafted in all treated mice. Average tumor growth in these groups (n=10 mice/group) is illustrated in FIG. 5.

FIG. 5A. Average group (n=10/group) tumor volume for the duration of the treatment of NOD SCID mice injected with BL-2 cells (Initial average tumor size 125 mm$^3$). A. CCI-002 monotherapy and B combination therapy of CCI-002 with doxorubicin.

Summary of Results (BL)

Overall, the test article CCI-002 at 20 mg/kg, 50 mg/kg and 60 mg/kg treatment groups produced significant antitumor activities in treatment of the subcutaneous BL-2 Burkitt lymphoma subcutaneous xenograft model.

The test article CCI-002 showed an obvious dose response effect as monotherapy. When in combination with doxorubicin, the synergetic effect of antitumor activities was observed at 10 and 20 mg/kg CCI-002.

At the high doses of CCI-002 (50 and 60 mpk), treatment was suspended for various period of times to allow for recovery from body weight loss and "normal" body weight was recovered.

Regarding the safety profile, the test article CCI-002 at 20 mg/kg showed good safety profile. However, a severe body weight loss (10-30%) was observed in the animals treated with CCI-002 at 50 and 60 mg/kg, doxorubicin 4 mg/kg or in combination treatment. Diarrhea in some mice of groups in Groups 4, 5, 6, and 7 was observed. Importantly, after suspended for dosing and rehydration treatment (final concentration: NaCl: 2.5 g/L, Glucose: 30 g/L) for two days under the animal conditions, including diarrhea and body weight loss exceeding 15%, were improved above the 15% threshold.

Materials and Methods

Cell Culture

L0, IM9, Ramos, BL2, Daudi, KMH2, Jurkat and CEM cells were purchased from the American Type Culture Collection (ATCC; Manassas, VA, U.S.A) and were maintained in RPMI medium supplemented with 10% FBS, 100 U/ml penicillin, 0.1 mg/ml streptomycin, 1 mM sodium pyruvate and 2 mM L-Glutamine. All cells used were maintained at 37° C. and 5% CO2 in a humidified incubator.

Cell Lysis

Cells were washed in cold PBS, harvested, lysed in 0.1% SDS-RIPA buffer [50 mM Tris pH 8.0, 150 mM NaCl, 1% Igepal CA-630, 0.5% NaDC, 2 mM MgCl2, 2 mM EDTA with 1× complete protease inhibitor (Roche Diagnostics)] by rocking for 15 min at 4° C. Cell lysates were then centrifuged at 16,000 g for 10 min at 4° C. and the post-nuclear supernatant was collected.

Viability of Cells Treated with NMT Inhibitors $2\times10^e$ cells CEM (T cell leukemia), L0 ("normal" B cell), BL2 and Ramos] were grown in 6 well plates and incubated with increasing amounts (0, 1, 2 and 5 μg/ml) of Tris-DBA (25) for 24 hours. Tris-DBA was a kind gift from Dr. Jack Arbiser (Emory University, GA, USA). $1\times10^5$ cells [KMH2 (Hodgkins lymphoma), IM9 ("normal" B cell), BL2, Ramos] were plated in 96-well plates and treated with increasing amounts of DDD85646, DDD73228 and DDD86481 for 24, 48 and 72 hours. DDD85646, DDD73228 and DDD86481 were kind gifts from Drs. David Gray and Paul Wyatt at the University of Dundee, Scotland, UK.

Measurement of Cell Viability

The viability of cells treated with Tris-DBA, DDD73228, and DDD85646 was measured by incubating cells treated with Tris-DBA using TC10TM Trypan Blue Dye (Biorad, Hercules, CA, USA) according to manufacturer's instructions. Cell viability was then quantified using the TC10TM automated cell counter (Biorad). The viability of cells treated with DDD86481 was measured using the CellTiter 96 AQueous Non-Radioactive cell proliferation assay (MTS) from Promega (Madison, WI, USA) according to manufacturers instructions.

qRT-PCR of B Cell Lymphoma Cell Lines

RNA was isolated from IM9, KMH2, Ramos and BL2 cells using TRIzol® reagent according to manufacturers protocols. Next, the High Capacity cDNA Reverse Transcription kit with a random primer scheme from Applied Biosciences was used to synthesize cDNA from the isolated RNA according to manufacturers instructions. Quantitative real time PCR (qRT PCR) reactions were set-up using the TaqMan® Universal Master Mix II and NMT1, NMT2 and 18 Taqman® probes purchased from Life Technologies (Carlsbad, CA) and three replicates of each reaction were set up according to suppliers guidelines. qRT PCR was performed using a Mastercyclere ep realplex thermocycler (Eppendorf) and results were analyzed using the Realplex software (Eppendorf).

Treatment of Cells with SAHA

IM9, BL2 and Ramos cells were plated at 3×106 cells per well in a 6-well dish and treated with 1_M suberoylanilide hydroxamic acid (SAHA) for 24 hours. Equal amount of DMSO was added to the control samples. Cells were lysed and subjected to SDS-PAGE. Western blotting was performed with antibodies against NMT1, NMT2, p21/WAF-1 and GAPDH.

Bisulphite Sequencing

Chromatin DNA was isolated from the cells using the QIAamp DNA and Blood Mini kit from Qiagen. DNA (20 μl; concentration, 1 ng to 2 μg/μl) was converted with the EpiTech Bisulfite kit (Qiagen) and amplified with bisulphite-specific primers (Table 4).

TABLE 4

Primers used for bisulphite sequencing.

| Primers | Primer Sequence | SEQ ID NO: | Tm (°C.) | Product size (bp) |
|---|---|---|---|---|
| 1F | GTTTTGTTTTTGTTTTGTTGAGAT | 1 | 52.2 | 344 |
| 1R | TCCTTTTATATTTTAACCCCATTTAC | 2 | | |
| 2F | TTTAATAAGGATGGTAGGGAGTAGAG | 3 | 53 | 519 |
| 2R | ACCAACCAACAAAACCTAAAACTAA | 4 | | |
| 3F | GATTTAATAAGGATGGTAGGGAGTAG | 5 | 51 | 360 |
| 3R | ACTCCCAAAACTAAAAATTCTTC | 6 | | |
| 4F | GGTTTTGTTTTGAAGAGTTTTAGG | 7 | 53 | 232 |
| 4R | ACTCCCTACCATCCTTATTAAATCC | 8 | | |

The amplified PCR products were cleaned with QIAquick PCR Purification kit (Qiagen) and cloned with the TA Cloning Kit (Life Technologies) and pC 2.1 Vector. The sequences were analyzed with QUMA.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A method comprising determining hypermethylation of a promoter region of an NMT2 gene in a tumor sample from a human subject with lymphoma, optionally compared to a control, and administering an NMT inhibitor to said subject, wherein said NMT inhibitor is DDD85646 or DDD86481, wherein determining hypermethylation of the promoter region of the NMT2 gene comprises:
   i) performing bisulfite modification to a nucleic acid obtained from the sample of the subject,
   ii) determining methylation of the promoter region of the NMT2 gene in the bisulfite-modified nucleic acid of the sample using PCR primers and/or probes specific for the promoter region of the NMT2 gene, optionally wherein the methylation of the promoter region is compared to a control.

2. A method comprising:
   a) obtaining nucleic acid from a tumor sample from a human subject with lymphoma;
   b) determining hypermethylation of a promoter region of an NMT2 gene in the sample, optionally compared to a control, and
   c) administering an NMT inhibitor to said subject, wherein said NMT inhibitor is DDD85646 or DDD86481,
   wherein determining hypermethylation of the promoter region of the NMT2 gene comprises:
   i) performing bisulfite modification to the nucleic acid in said sample, and
   ii) determining methylation of the promoter region of the NMT2 gene in the bisulfite-modified nucleic acid of the sample using PCR primers and/or probes specific for the promoter region of the NMT2 gene from step i), wherein step ii) is performed on the bisulfite modified nucleic acid from step i) by a method selected from the group consisting of PCR, methylation-specific PCR, quantitative methylation specific PCR (QMSP), realtime methylation-specific PCR, a PCR assay using a methylation DNA-specific binding protein, quantitative PCR, DNA chip-based assay, pyrosequencing, and bisulfite sequencing.

3. The method of claim 2, wherein said PCR primers comprise SEQ ID NO:1 and/or SEQ ID NO: 2.

4. The method of claim 2, wherein said method further comprises administering a histone acetyl transferase inhibitor, a DNA demethylase Inhibitor, and/or a histone demethylase inhibitor to said subject.

5. The method of claim 4, wherein said histone acetyl transferase inhibitor is anacardic acid, CPTH2, MB-3, and/or Curcumin.

6. The method of claim 4, wherein said histone demethylase inhibitor is Daminozide, GSK J1, GSK J2, GSK J4, GSK J5, GSK LSD 1 dihydrochloride, IOX 1, JIB 04, RN 1 dihydrochloride, TC-E 5002, and/or Tranylcypromine hydrochloride.

7. The method of claim 2, wherein said method further comprises administering CHOP (cyclophosphamide, doxorubicin, vincristine, and prednisone), GAP-BOP (cyclophosphamide, doxorubicin, procarbazine, bleomycin, vincristine, and prednisone), m-BACOD (methotrexate, bleomycin, doxorubicin, cyclophosphamide, vincristine, dexamethasone, and leucovorin), ProMACE-MOPP (prednisone, methotrexate, doxorubicin, cyclophosphamide, etoposide, leucovorin with standard MOPP), ProMACE-CytaBOM (prednisone, doxorubicin, cyclophosphamide, etoposide, cytarabine, bleomycin, vincristine, methotrexate, and leucovorin), or MACOP-B (methotrexate, doxorubicin, cyclophosphamide, vincristine, prednisone, bleomycin, and leucovorin) to said subject.

8. The method of claim 1, wherein the determination of hypermethylation in the promoter region of the NMT2 gene is performed by a method selected from the group consisting of PCR, methylation-specific PCR, realtime methylation-specific PCR, a PCR assay using a methylation DNA-specific binding protein, quantitative PCR, DNA chip-based assay, pyrosequencing, and bisulfite sequencing.

* * * * *

SEQUENCE LISTING

```
<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
gttttgtttt ttgttttgtt gagat                                         25

<210> SEQ ID NO 2
```

```
<211> LENGTH: 26
<212> TYPE: DNA
<213> ORGANISM: Artificial Sequence
<220> FEATURE:
<223> OTHER INFORMATION: Primer

<400> SEQUENCE: 2 tcctttata ttttaacccc atttac                                       26

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
tttaataagg atggtaggga gtagag                                      26

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
accaaccaac aaaacctaaa actaa                                       25

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
gatttaataa ggatggtagg gagtag                                      26

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
actcccaaaa ctaaaaattc ttc                                         23

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
ggttttgttt tgaagagttt tagg                                        24

<210> SEQ ID NO 8
<211> LENGTH: 25
<212> TYPE: DNA
<213> ORGANISM: Artificial Sequence
```

```
<220> FEATURE:
<223> OTHER INFORMATION: Primer

<400> SEQUENCE: 8
actccctacc atccttatta aatcc                                           25
```